United States Patent
Greger et al.

(10) Patent No.: US 12,186,747 B1
(45) Date of Patent: Jan. 7, 2025

(54) ASSAY CARTRIDGE

(71) Applicant: Amazon Technologies, Inc., Seattle, WA (US)

(72) Inventors: William Brian Greger, San Francisco, CA (US); Aida Martin Galan, Millbrae, CA (US); Manuela Alanis, Buenos Aires (AR); Emanuel Elizalde, Santa Fe (AR); Luciano Braggio, Santa Fe (AR)

(73) Assignee: Amazon Technologies, Inc., Seattle, WA (US)

( * ) Notice: Subject to any disclaimer, the term of this patent is extended or adjusted under 35 U.S.C. 154(b) by 303 days.

(21) Appl. No.: 17/546,350

(22) Filed: Dec. 9, 2021

(51) Int. Cl.
| | | |
|---|---|---|
| *B01L 3/00* | (2006.01) | |
| *B01L 7/00* | (2006.01) | |
| *C12N 9/22* | (2006.01) | |
| *C12Q 1/6844* | (2018.01) | |
| *G01N 1/20* | (2006.01) | |

(52) U.S. Cl.
CPC ......... *B01L 3/502715* (2013.01); *B01L 7/52* (2013.01); *C12Q 1/6844* (2013.01); *G01N 1/2035* (2013.01); *B01L 2200/04* (2013.01); *B01L 2200/16* (2013.01); *B01L 2300/0663* (2013.01); *B01L 2300/1827* (2013.01); *C12N 9/22* (2013.01); *C12N 2310/20* (2017.05); *G01N 2001/205* (2013.01)

(58) Field of Classification Search
CPC .. B01L 3/502715; B01L 7/52; B01L 2200/04; B01L 2200/16; B01L 2300/0663; B01L 2300/1827; C12Q 1/6844; G01N 1/2035; G01N 2001/205; C12N 9/22; C12N 2310/20

See application file for complete search history.

(56) References Cited

U.S. PATENT DOCUMENTS

| | | | |
|---|---|---|---|
| 2014/0080717 A1* | 3/2014 | Li | C12Q 1/6853 506/26 |
| 2018/0066223 A1* | 3/2018 | Lim | C12M 41/48 |
| 2018/0164221 A1* | 6/2018 | Singh | C12N 1/20 |
| 2019/0212233 A1* | 7/2019 | Jovanovich | C12N 1/06 |
| 2021/0078002 A1* | 3/2021 | Chen | B01L 3/502715 |
| 2021/0292824 A1* | 9/2021 | Zhang | C12N 9/78 |
| 2022/0002789 A1* | 1/2022 | Freije | C12Q 1/6827 |

OTHER PUBLICATIONS

Venting with Hydrophobic vs. Oleophobic Membranes, 2011, www.gore.com/sites/default/files/2016-04/PTV-TechInfo-Hydrophobic-Oleophobic-US.pdf (Year: 2011).*
U.S. Appl. No. 17/547,096, filed Dec. 9, 2021, Titled: Microfluidic Systems and Methods.

* cited by examiner

*Primary Examiner* — Jennifer Wecker
*Assistant Examiner* — Ali Husain Faraz
(74) *Attorney, Agent, or Firm* — Kilpatrick Townsend & Stockton LLP

(57) ABSTRACT

Single use cartridges for testing biological samples are provided that include multiple processing channels. A single use cartridge includes an aliquot staging well, a first amplification well, a second amplification well, an actuation port, and a fluid channel control valve assembly. The fluid channel control valve assembly is reconfigurable between a first fluid channel configuration and a second fluid channel configuration.

16 Claims, 57 Drawing Sheets

ASSAY CARTRIDGE

BACKGROUND

Diagnostic testing of biological samples for the presence of pathogens is an important tool for identifying infected individuals. Where diagnostic testing indicates that an individual is infected by a pathogen, the individual can receive suitable treatment for the infection and can limit contact with other people to limit and hopefully avoid spreading the pathogen to others.

Diagnostic testing for the presence of some pathogens, however, often involves fairly complex processing of a biological sample. Complex processing of the biological sample is typically performed using expensive specialized equipment, often in a laboratory setting, which limits the availability of the diagnostic testing for the pathogen. The limited availability of the diagnostic testing inhibits timely treatment of infected individuals and inhibits limiting spreading of the pathogen.

BRIEF DESCRIPTION OF THE DRAWINGS

Various embodiments in accordance with the present disclosure will be described with reference to the drawings, in which.

DETAILED DESCRIPTION

Figure 1:
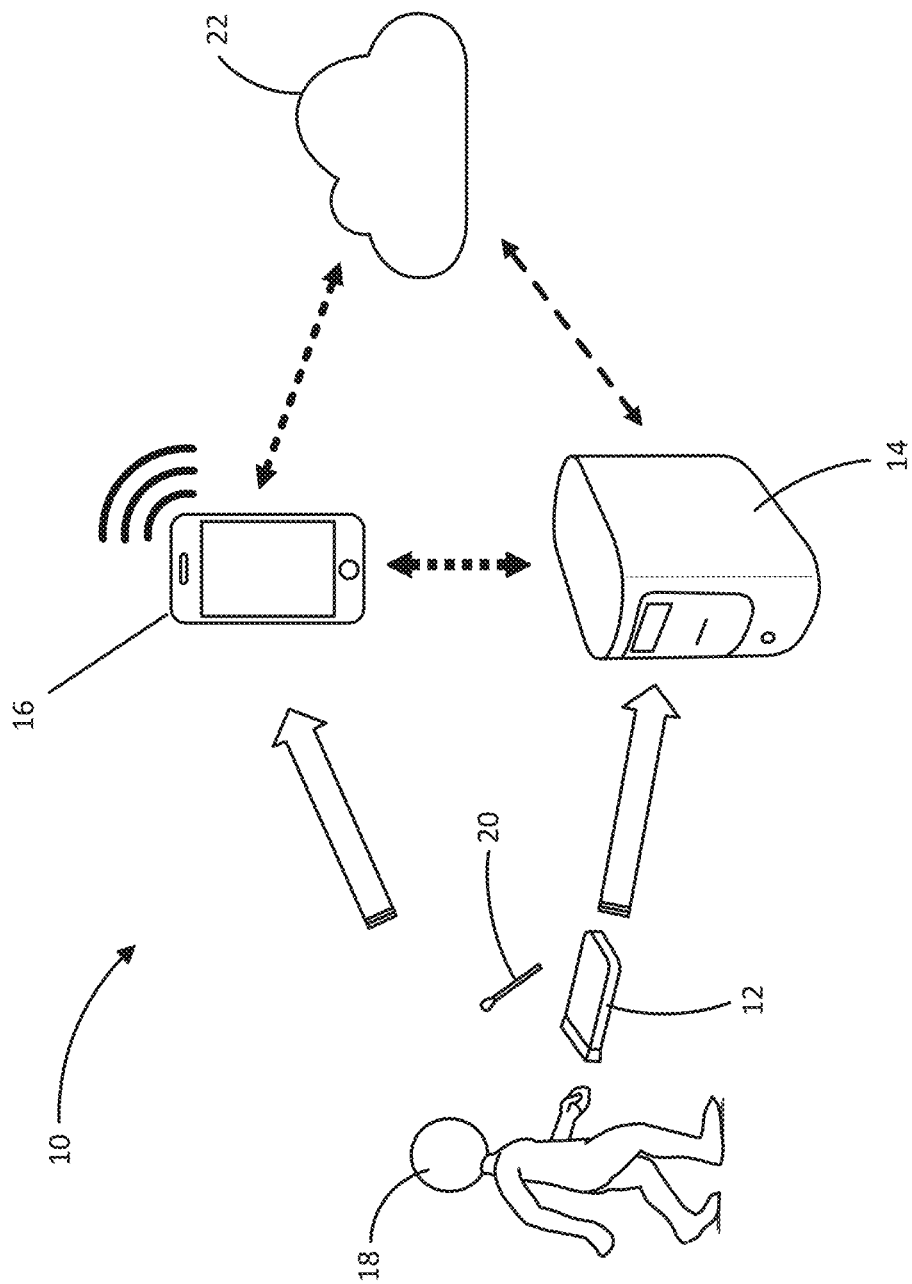
FIG. 1 is a simplified schematic diagram of a diagnostic testing system, in accordance with embodiments, that can be used at home to test whether a person is infected with a pathogen.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

The systems, devices, and approaches described herein are directed to diagnostic testing of biological samples for the presence of one or more pathogens. More specifically, a portable diagnostic testing system is described that can be used at home or any other suitable setting. In many embodiments, the portable diagnostic system processes a biological sample using amplification (e.g., reverse transcriptase loop-mediated amplification (RT-LAMP)) followed by fluorescence emission triggered by a Clustered Regularly Interspaced Short Palindromic Repeats (CRISPR)-CRISPR associated proteins (CAS) enzyme to detect whether the biological sample contains one or more target pathogens.

In many embodiments, an analysis device is used in conjunction with a single-use cartridge to test a biological sample for each of one or more target pathogens. The system can be adapted for detecting any suitable one or more pathogens including, but not limited to, any suitable combination of one or more of SARS-CoV-2, Adenovirus, Coronavirus HKU1, Coronavirus NL63, Coronavirus 229E, Coronavirus OC43, Human Metapneumovirus, Human Rhinovirus, Human Enterovirus, Influenza A, Influenza A/H1, Influenza A/H1-2009, Influenza A/H3, Influenza B, Parainfluenza 1, Parainfluenza 2, Parainfluenza 3, Parainfluenza 4, Respiratory Syncytial Virus, Adenovirus F40/41, Astrovirus, Norovirus GI, Norovirus GII, Rotavirus A, Sapovirus I, Sapovirus II, Sapovirus IV, and Sapovirus V. The systems and methods described herein can be used at the point of care, including in very low complexity medical environments. The system and methods described herein can also be used in any other suitable location, such as in a house.

The systems and methods described herein can be used to test for the presence of the one or more target pathogens in a biological sample collected with a swab, nasal or nasopharyngeal. In many embodiments, an analyzer device generates and transmits raw fluorescence results to a mobile device application, through a suitable communication connection (e.g., USB cable, WiFi, Bluetooth, etc.).

In many embodiments, a single-use microfluidic cartridge includes an actuation port that is coupled with a pump assembly of the analyzer device. In many embodiments, the pump assembly is configured to withdraw air from the cartridge through the actuation port to induce movement of fluid within the cartridge and/or to inject air into the cartridge through the actuation port to induce movement of fluid within the cartridge.

For example, in many embodiments, the pump assembly withdraws air from the cartridge through the actuation port to draw an aliquot of a sample solution into contact with a staging port configured to resist movement of the aliquot of the sample solution past the staging port. The staging port can include a hydrophobic vent that is configured to accommodate passage of air to the actuation port and resist passage of the aliquot of the sample solution through the hydrophobic vent. As a result of the resistance of the staging port hydrophobic vent to passage of the aliquot of the sample solution, when the sample solution comes into contact with the staging port hydrophobic vent the flow of the sample solution is stopped thereby resulting in increased vacuum pressure generated by a pump assembly of the analyzer. The analyzer device is configured to detect when the aliquot comes into contact with the staging port hydrophobic vent by detecting the resulting increased resistance of the cartridge to further withdrawal of air from the actuation port by the analyzer device. In many embodiments, the analyzer device detects the resulting increased resistance of the cartridge to further withdrawal of air from the actuation port by monitoring the vacuum pressure generated by the pump assembly. In many embodiments, the analyzer device stops operation of the pump assembly in response to detecting an increase in the vacuum pressure indicative of contact of the sample solution with the staging port hydrophobic vent. In some embodiments, the analyzer detects the resulting increase resistance of the cartridge to further withdrawal of air from the cartridge through the actuation port by monitoring one or more power supply parameters for a motor of the pump assembly (e.g., current, motor rotational speed). In such embodiments, the analyzer device stops operation of the pump assembly in response to detecting a change in the one or more power supply parameters indicative of contact of the sample solution with the staging port hydrophobic vent.

In many embodiments, the analyzer device operates the pump assembly to inject air into the cartridge through the actuation port to move fluid within the cartridge. For example, the analyzer can operate the pump assembly to inject air into the cartridge through the actuation port to move the aliquot to a reaction well (e.g., an RT-LAMP well). In many embodiments, the reaction well includes a reaction well hydrophobic vent that is configured to accommodate passage of air and resist passage of aliquot of the sample solution through the reaction well hydrophobic vent. As a result of the resistance of the reaction well hydrophobic vent to passage of the sample solution, when the sample solution comes into contact with the reaction hydrophobic vent the flow of the sample solution is stopped thereby resulting in increased positive pressure generated by the pump assembly of the analyzer. The analyzer device is configured to detect when the aliquot comes into contact with the reaction well hydrophobic vent by detecting the resulting increased resistance of the cartridge to further injection of air into the actuation port by the pump assembly. In many embodiments, the analyzer device detects the resulting increased resistance of the cartridge to further injection of air into the cartridge through the actuation port by monitoring the pressure generated by the pump assembly. In many embodiments, the analyzer device stops operation of the pump assembly in response to detecting an increase in positive pressure generated by the pump assembly indicative of contact of the sample solution with the reaction well hydrophobic vent. In some embodiments, the analyzer detects the resulting increased resistance of the cartridge to further injection of air into the cartridge through the actuation port by monitoring one or more power supply parameters (e.g., drive current, rotation speed, output torque) for a motor of the pump assembly. In such embodiments, the analyzer device stops operation of the pump assembly in response to detecting an increase in the one or more power supply parameters indicative of contact of the sample solution with the reaction well hydrophobic vent.

In many embodiments, the analyzer device includes a selection valve that is configurable by the analyzer device to block flow of the aliquot of the sample solution when the aliquot is being transferred to the reaction well and can be reconfigured by the analyzer device to accommodate transfer of fluid from the reaction well to a second reaction well via further injection of air into the actuation port by the pump assembly. In some embodiments, the selection valve includes the reaction well hydrophobic vent.

In many embodiments, the cartridge includes a buffer solution chamber assembly that stores a buffer solution (e.g., nuclease-free water) for eluting a sample from a sample swab inserted into the cartridge. In many embodiments, the analyzer device included a plunger and the analyzer device produces relative movement between the plunger and the buffer solution chamber assembly so that the plunger displaces a piston of the buffer solution chamber assembly to transfer buffer solution out of the buffer solution chamber assembly and through the cartridge to form the sample solution via eluting the sample from the sample swab.

Turning now to the drawing figures, in which similar reference identifiers refer to similar elements, FIG. 1 shows a diagnostic testing system 10, in accordance with embodiments. The diagnostic testing system 10 includes a single-use cartridge 12, an analyzer 14, and a user device 16. A person 18 can use the system 10 to test a biological sample for the presence of one or more pathogens. A biological sample can be collected with a swab 20 using any suitable approach with respect to the one or more target pathogens. For example, for many viruses, the swab 20 can be used to swab a nasal passage to collect the biological sample onto the swab. The swab 20 is then inserted into the cartridge 12. The cartridge 12 is then inserted into the analyzer 14, which operates the cartridge 12 as described herein to accomplish the testing. The user device 16 can transmits the result to the cloud 22. Any suitable user device 16 can be employed in the diagnostic system 10 including, but not limited to, a smart phone, a personal computer, a physician's computer system, a tablet computer, and the like. In many embodiments, the cloud 22 includes the network 4204, the Web server 4206, the at least one application server 4208, and the data store 4210 of the example environment 4200 (shown in FIG. 57).

Figure 2:
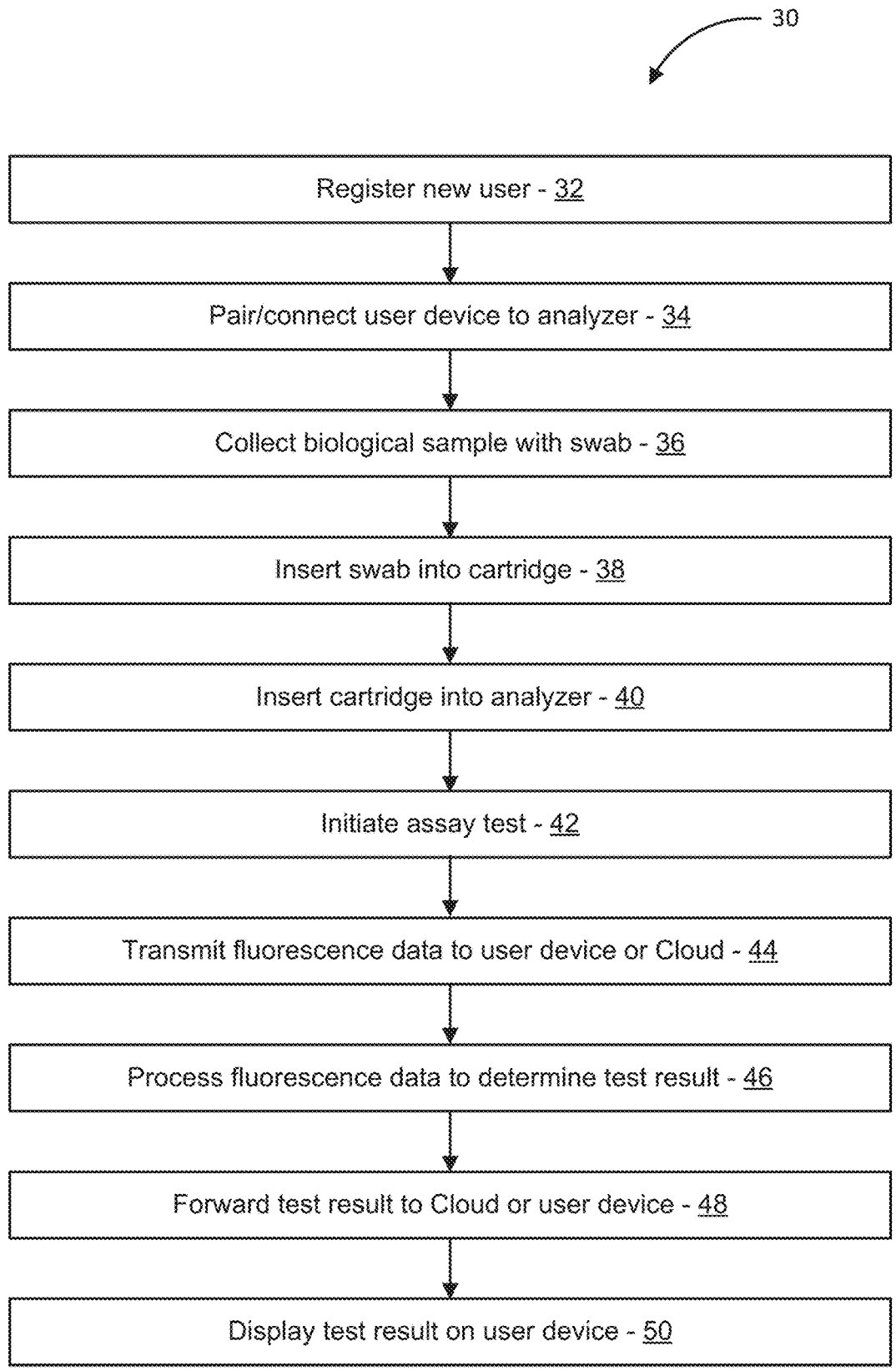
FIG. 2 is a simplified flow chart of a diagnostic test approach that can be accomplished using the diagnostic testing system of FIG. 1.

FIG. 2 is a simplified flow chart of acts of a diagnostic test process 30 that can be accomplished using the diagnostic testing system 10. In the process 30, a person 18 interacts with the system 10 by way of a software application executed by the user device 16. For example, the user device 16 can be a smartphone and the software application can be a smartphone application that runs on the smartphone. In act 32, the person 18 interacts with the smartphone application to register a new user profile. In act 34, the user device 16 and the analyzer are communicatively coupled using any suitable approach (e.g., Bluetooth, WiFi, USB cable). In many embodiments, the smartphone application displays instructions for use (IFU) of the system 10. In act 36, a biological sample is collected with the swab 20. For example, the IFU can instruct the person 18 to swab both nostrils of a subject in the anterior nares region to collect the biological sample. In act 38, the swab 20 is inserted into the cartridge 12. In act 40, the user 18 inserts the cartridge 12 into the analyzer 14. In act 42, testing of the biological sample is initiated, which can occur via the smartphone application transmitting an initiation command to the analyzer 14 to commence the testing. Alternatively, testing of the biological sample can be initiated by pressing a button on the analyzer 14 or the testing of the biological sample can start automatically in response to insertion of the cartridge 12 into the analyzer 14. During the testing, the analyzer 14 can interact the cartridge as described herein to process the biological sample and generate raw fluorescence data for processing to determine a test result. In act 44, the analyzer 14 transmits the generated raw fluorescence data to the user device 16 for processing via the smartphone application. In act 46, the user device 16 processes the raw fluorescence data under the control of the smartphone application to determine a test result. In many embodiments, the test result is one of a positive result indicating that the biological sample contains the target pathogen, a negative result indicting that the biological sample does not contain the target pathogen, or an invalid test result indicating that the test did not produce a valid result. For example, an invalid test result may occur where an insufficient biological sample was used, pressure feedback from the cartridge is inadequate to detect when liquid reaches a hydrophobic vent(s) resulting in invalid staging of liquid in the cartridge, and/or the sample tested is not from a human. In act 48, the user device 16 transmits the result to the cloud 22. In act 50, the test result is displayed on the user device 16. Suitable variations in the process 30 can be employed. For example, suitable variations in the order in which the acts of process 30 are accomplished can be employed. Additionally, one or more of the acts of the process 30 need not be accomplished each time a biological sample is analyzed. For example, act 32 can be omitted where a user profile associated with the biological sample has already been registered. As another example, act 48 can be omitted where no forwarding of the test result is employed.

Some or all of the process 30 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Figure 3:
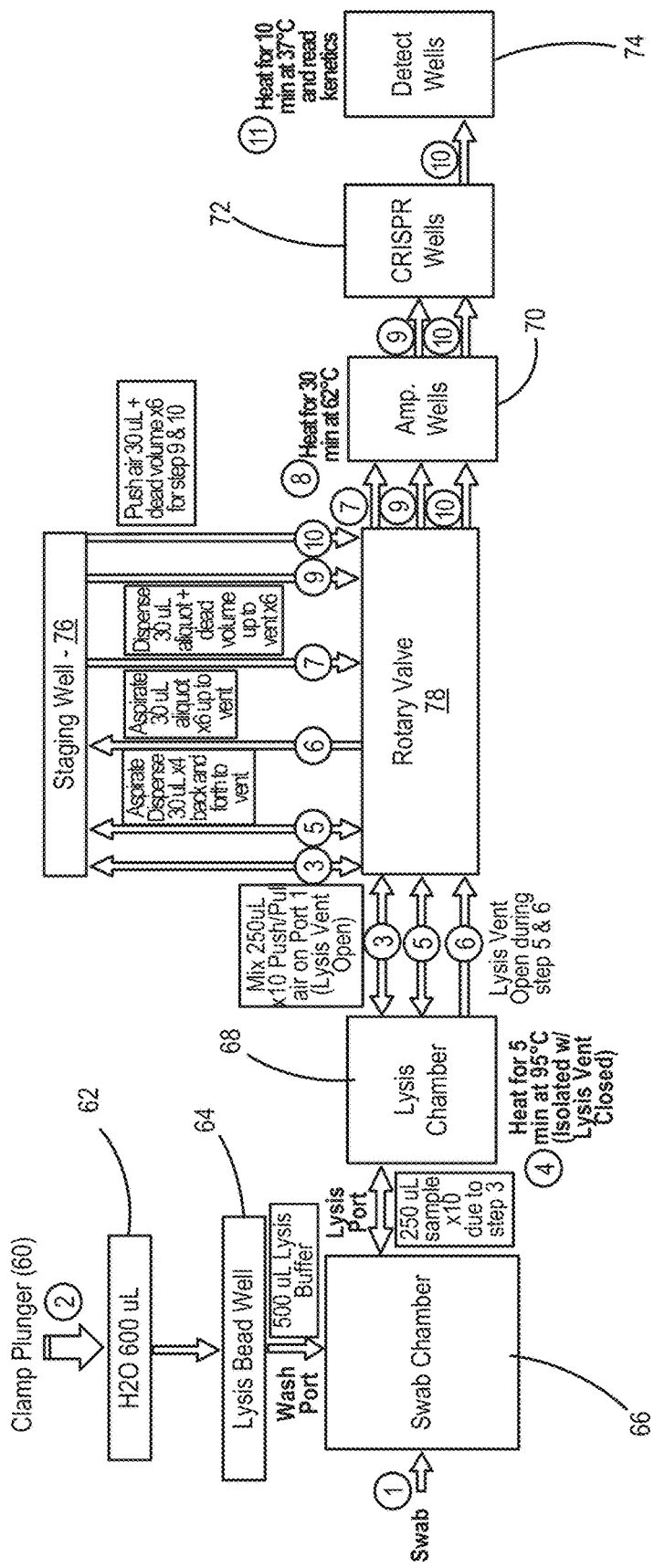
FIG. 3 is a schematic diagram illustrating process steps employed in an example of the diagnostic testing system of FIG. 1.

FIG. 3 is a simplified schematic diagram of elements of the cartridge 12 via which the biological sample is processed (via operation of the cartridge 12 by the analyzer 14) to generate the raw fluorescence results that are processed by the user device 16. Upon initiation of the testing (act 42 of FIG. 2), the analyzer 14 operatively couples interfacing elements of the analyzer 14 with the cartridge 12. The analyzer 14 can use any suitable approach to couple the interfacing elements of the analyzer 14 with the cartridge 12. For example, in embodiments described herein the analyzer 14 includes a clamping mechanism that supports the cartridge 12 and moves the cartridge 12 laterally into engagement with the interfacing elements of the analyzer 14. One of the interfacing elements of the analyzer 14 is a clamp plunger 60 that displaces a piston of a buffer solution chamber assembly 62 of the cartridge 12. The buffer solution chamber assembly 62 includes a buffer solution chamber that contains a suitable quantity of a buffer solution (e.g., 600 uL of nuclease-free water). The engagement of the clamp plunger 60 with the piston of the buffer solution chamber assembly 62 displaces the piston into a buffer solution chamber of the buffer solution chamber assembly 62, thereby pushing a flow of the buffer solution from the buffer solution chamber to a lysis bead chamber 64 of the cartridge 12. The lysis bead chamber 64 contains one or more lyophilized lysis beads. The buffer solution hydrates the lyophilized lysis bead to form a suitable quantity of a lysis buffer (e.g., 500 uL). Continued displacement of the piston into the buffer solution chamber by the clamp plunger 60 pushes a flow of the lysis buffer from the lysis bead chamber 64 into a swab chamber 66 of the cartridge 12 so as to interface the lysis buffer with the swab 20 to elute the biological sample out of the swab head to form a lysis buffer sample solution. Continued displacement of the piston into the buffer solution chamber by the clamp plunger 60 pushes a suitable quantity of the lysis buffer sample solution (e.g., 250 uL) from the swab chamber 66 to a lysis chamber 68 of the cartridge 12. In many embodiments, the lysis chamber 68 is connected to a lysis chamber hydrophobic vent 84 (shown in FIG. 4) for venting of the lysis chamber 68 during transfer of the buffer solution from the buffer solution chamber via the displacement of the piston into the buffer solution chamber. Following the transfer of the lysis buffer sample solution to the lysis chamber 68, a lysis chamber heating element of the analyzer 14 heats the lysis buffer sample solution to a suitable temperature (e.g., 95 degrees C.) for a suitable time period (e.g., 5 minutes) to break down cell membranes of the biological sample to form a lysed sample solution. During the lysis of the biological sample, a hydrophobic lysis vent of the cartridge is kept closed (using a rotary valve system) to fluidically isolate the lysis chamber 68.

The resulting lysed sample solution is then processed via one or more processing channels of the cartridge 12, which can have any suitable number of the processing channels. For example, in an embodiment of the cartridge 12 described herein, the cartridge 12 has 6 processing channels. Each of the six processing channels of the cartridge 12 includes a reaction well 70 (e.g., an amplification well such as an RT-LAMP well), a CRISPR well 72, and a detection well 74. Six aliquots of the lysed sample solution are sequentially extracted from the lysis chamber 68. Each of the six aliquots of the lysed sample solution is processed via one of the processing channels. The cartridge 12 includes a staging well 76 and a rotary valve 78. The rotary valve 78 has a lysis sample solution transfer configuration (shown in FIG. 6), a lysis chamber venting configuration (shown in FIG. 7), an aliquot staging configuration (shown in FIG. 8), a first processing channel configuration (shown in FIG. 9 and FIG. 10), a second processing channel configuration (shown in FIG. 11 and FIG. 12), a third processing channel configuration (shown in FIG. 13 and FIG. 14), a fourth processing channel configuration (shown in FIG. 15 and FIG. 16), a fifth processing channel configuration (shown in FIG. 17 and FIG. 18), and a sixth processing channel configuration (shown in FIG. 19 and FIG. 20). In the lysis sample solution transfer configuration of the rotary valve 78, the lysis chamber 68 and the swab chamber 124 are in fluid communication through the rotary valve 78. In the lysis chamber venting configuration of the rotary valve 78, the lysis chamber 68 and the lysis chamber hydrophobic vent 84 are in fluid communication through the rotary valve 78. In the aliquot stating configuration of the rotary valve 78, the lysis chamber 68 and the staging well 76 are in fluid communication through the rotary valve 78. In the first processing channel configuration of the rotary valve 78, the staging well 76 and the reaction well 70 of the first processing channel of the cartridge 12 are in fluid communication through the rotary valve 78. In the second processing channel configuration of the rotary valve 78, the staging well 76 and the reaction well 70 of the second processing channel of the cartridge 12 are in fluid communication through the rotary valve 78. In the third processing channel configuration of the rotary valve 78, the staging well 76 and the reaction well 70 of the third processing channel of the cartridge 12 are in fluid communication through the rotary valve 78. In the fourth processing channel configuration of the rotary valve 78, the staging well 76 and the reaction well 70 of the fourth processing channel of the cartridge 12 are in fluid communication through the rotary valve 78. In the fifth processing channel configuration of the rotary valve 78, the staging well 76 and the reaction well 70 of the fifth processing channel of the cartridge 12 are in fluid communication through the rotary valve 78. In the sixth processing channel configuration of the rotary valve 78, the staging well 76 and the reaction well 70 of the sixth processing channel of the cartridge 12 are in fluid communication through the rotary valve 78. The analyzer 14 includes a rotary valve actuation assembly 80 (shown in FIG. 32 and FIG. 33) that is drivingly coupled with the rotary valve 78 and operable to reconfigure the rotary valve 78 to each of the configurations of the rotary valve 78.

The cartridge 12 is operable to sequentially transfer separate aliquots of the lysed sample solution from the lysis chamber 68 to the staging well 76, and to transfer each of the aliquots of the lysed sample solution from the staging well 76 to a respective one of the amplification wells 70. The cartridge 12 includes an actuation port 83 (shown in FIG. 4) and an aliquot staging well hydrophobic passage 82 through which the staging well 76 is connected to the actuation port 83 for withdrawing air from the staging well 76 via withdrawing air from the actuation port 83 and for injecting air into the staging well 76 via injecting air into the actuation port 83. The analyzer 14 includes a pump assembly 86 (shown in FIG. 27) that is operatively coupled with the actuation port 83. The pump assembly 86 is operable to suction air from the cartridge 12 through the actuation port 83 and to inject air into the cartridge 12 through the actuation port 83.

In the sequence illustrated in FIG. 3, the analyzer 14 operates the pump assembly 86 to alternately withdraw air from the cartridge 12 through the actuation port 83 and inject air into the cartridge 12 through the actuation port 83 to move a quantity of the lysed sample solution back and forth between the staging well 76 and the lysis chamber 68 to cool and vent the lysed sample solution before distributing respective aliquots of the lysed sample solution to each of the six processing channels of the cartridge 12. With the rotary valve 78 in the aliquot staging configuration, the pump assembly 86 is operated to suction air from the cartridge 12 through the actuation port 83 so as to pull a quantity of the lysed sample solution from the lysis chamber 68 into the staging well 76 and into contact with the aliquot staging well hydrophobic passage 82. As described herein, the aliquot staging well hydrophobic passage 82 is configured to accommodate passage of air and resist passage of the lysed sample solution. As a result of the resistance of the aliquot staging well hydrophobic passage 82 to passage of the lysed sample solution, when the lysed sample solution comes into contact with the aliquot staging well hydrophobic passage 82 the flow of the lysed sample solution towards the actuation port 83 is stopped thereby resulting in increased suction pressure generated by the pump assembly 86. In many embodiments, the analyzer 14 monitors the pressure generated by the pump assembly 86 and stops operation of the pump assembly 86 in response to detecting an increase in the suction pressure indicative of contact of the lysed sample solution with the aliquot staging well hydrophobic passage 82. The pump assembly 86 is then operated to inject air into the cartridge 12 through the actuation port 83 so as to push the quantity of the lysed sample solution back into the lysis chamber 68 from the staging sell 76. The above described processes in which a quantity of the lysed sample solution is transferred from the lysis chamber 68 to the staging well 76 and then transferred back to the lysis chamber 68 can be repeated any suitable number of times (e.g., four times) to sufficiently cool and vent the lysed sample solution prior to distribution of respective aliquots of the lysed sample solution to the respective amplification wells 70 (e.g., RT-LAMP wells).

Following cooling and venting of the lysed sample solution, a respective aliquot of the lysed sample solution is staged from the lysis chamber 68 to the staging well 76 and then transferred to a respective one of the six amplification wells 70. For each of the aliquots, with the rotary valve 78 in the aliquot staging configuration, the pump assembly 86 extracts air from the cartridge 12 through the actuation port 83 to pull the aliquot from the lysis chamber 68 to the staging well 76 and into contact with the aliquot staging well hydrophobic passage 82. The analyzer 14 then operates the rotary valve actuation assembly 80 to reconfigure the rotary valve 78 from the aliquot staging configuration to the respective processing channel configuration. With the rotary valve 78 in the respective processing channel configuration, the pump assembly 86 injects air into the cartridge 12 through the actuation port 83 to push the aliquot from the staging well 76 into the respective amplification wells 70 and into contact with an amplification well hydrophobic vent 88 (shown in FIG. 4) associated with the respective amplification well 70. As described herein, each of the amplification well hydrophobic vents 88 is configured to accommodate passage of air and resist passage of the respective aliquot of the lysed sample solution. As a result of the resistance of the amplification well hydrophobic vent 88 to passage of the lysed sample solution, when the lysed sample solution comes into contact with the amplification well hydrophobic vent 88, the flow of the aliquot of the lysed sample solution away from the actuation port 83 is stopped thereby resulting in increased positive pressure generated by the pump assembly 86. In many embodiments, the analyzer 14 monitors the positive pressure generated by the pump assembly 86 and stops operation of the pump assembly 86 in response to detecting an increase in the positive pressure indicative of contact of the lysed sample solution with the amplification well hydrophobic vent 88. The rotary valve 78 is reconfigured back to the aliquot staging configuration prior to operating the pump assembly 86 to pull the next aliquot from lysis chamber 68 to the staging well 76.

Each of the amplification wells 70 contains a lyophilized amplification compound bead containing amplification compounds for accomplishing amplification (e.g., RT-LAMP). Each respective aliquot of the lysed sample solution hydrates the respective amplification compound bead to form a respective amplification sample solution aliquot.

Following the formation of the amplification sample solution aliquots in the amplification wells 70, the amplification sample solution aliquots in the amplification wells 70 are heated by a respective amplification well heating element 190, 192 (shown in FIG. 38) of the analyzer 14 to a suitable temperature (e.g., 62 degrees C. for RT-LAMP amplification) for a suitable time period (e.g., 30 minutes minimum) to accomplish amplification on the amplification sample solution aliquot to form respective amplified sample solution aliquots.

Following the formation of the amplified sample solution aliquots in the amplification wells 70, the analyzer 14 operates the cartridge 12 to stage each of the amplified sample solution aliquots to a respective CRISPR well 72. As described herein, the cartridge 12 includes a sliding valve 94 (shown in FIG. 4 and FIG. 5) that includes the six amplification well hydrophobic vents 88. The sliding valve 94 has a shipping configuration, a blocking configuration, and a transfer configuration. In the shipping configuration (shown in FIG. 21), the sliding valve 94 blocks fluid communication from each of the amplification wells 70 to both the associated CRISPR well 72 and the associated amplification well hydrophobic vent 88. In the blocking configuration (shown in FIG. 22), the sliding valve 94 blocks flow from each of the amplification wells 70 to the associated CRISPR well 72 along each of the six processing channels and connects each of the amplification wells with the associated amplification well hydrophobic vent 88. In the transfer configuration, the sliding valve 94 accommodates flow from the first processing channel amplification well 70 to the first processing channel CRISPR well 72, flow from the second processing channel amplification well 70 to the second processing channel CRISPR well 72, flow from the third processing channel amplification well 70 to the third processing channel CRISPR well 72, flow from the fourth processing channel amplification well 70 to the fourth processing channel CRISPR well 72, flow from the fifth processing channel amplification well 70 to the fifth processing channel CRISPR well 72, and flow from the sixth processing channel amplification well 70 to the sixth processing channel CRISPR well 72. The analyzer 14 includes a sliding valve actuation assembly 96 (shown in FIG. 27) that is drivingly coupled with the sliding valve 94 when the cartridge 12 is coupled to the analyzer 14. The sliding valve actuation assembly 96 is configured and operable to reconfigure the sliding valve 94 between the shipping configuration, the blocking configuration, and transfer configuration. To transfer each of the amplified sample solution aliquots from the respective amplification well 70 to the corresponding CRISPR well 72, the analyzer 14 reconfigures the rotary valve 78 to the corresponding processing channel configuration and then operates the pump assembly 86 to inject a predetermined amount of air into the cartridge 12 through the actuation port 83 to push the aliquot from the amplification well 70 to the corresponding CRISPR well 72.

Each of the CRISPR wells 72 contains a lyophilized CRISPR compound bead containing CRISPR compounds for accomplishing CRISPR. Each respective aliquot of the amplified sample solution hydrates the respective CRISPR compound bead to form a respective detection solution aliquot.

Following the formation of the detection solution aliquots in the CRISPR wells 72, the analyzer 14 operates the cartridge 12 to stage each of the detection solution aliquots to the respective detection well 74. To transfer each of the detection solution aliquots from the respective CRISPR well 72 to the corresponding detection well 74, the analyzer 14 reconfigures the rotary valve 78 to the corresponding processing channel configuration and then operates the pump assembly 86 to inject air into the cartridge 12 through the actuation port 83 to push the detection solution aliquot from the CRISPR well 72 to the corresponding detection well 74 and into contact with a detection well hydrophobic vent 98 (shown in FIG. 4) associated with the respective detection well 74. Each of the detection well hydrophobic vents 98 is configured to accommodate passage of air and resist passage of the respective aliquot of the detection sample solution. As a result of the resistance of the detection well hydrophobic vent 98 to passage of the detection sample solution, when the detection sample solution comes into contact with the detection well hydrophobic vent 98, the flow of the aliquot of the detection sample solution away from the actuation port 83 is stopped thereby resulting in increased positive pressure generated by the pump assembly 86. In many embodiments, the analyzer 14 monitors the positive pressure generated by the pump assembly 86 and stops operation of the pump assembly 86 in response to detecting an increase in the positive pressure indicative of contact of the detection sample solution with the detection well hydrophobic vent 98.

Following the transfer of the detection sample solution aliquots from the CRISPR wells 72 to the detection wells 74, the detection sample solution in each of the detection wells 74 is heated by a respective detection well heating element 100 (shown in FIG. 41) of the analyzer 14 to a suitable temperature (e.g., 37 degrees C.) for a suitable time period (e.g., 10 minutes). The CRISPR reaction causes a CRISPR complex to come into contact with the aliquot. If the target is present, the CAS effector cleaves a fluorescent probe.

Following the heating of the detection sample solutions in the detection wells 74, the analyzer 14 operates a fluorescence excitation assembly 102 and a fluorescence detection assembly 104 to generate raw fluorescence data as described herein. The raw fluorescence data is then transmitted to the user device 16 for processing as described herein.

Figure 4:
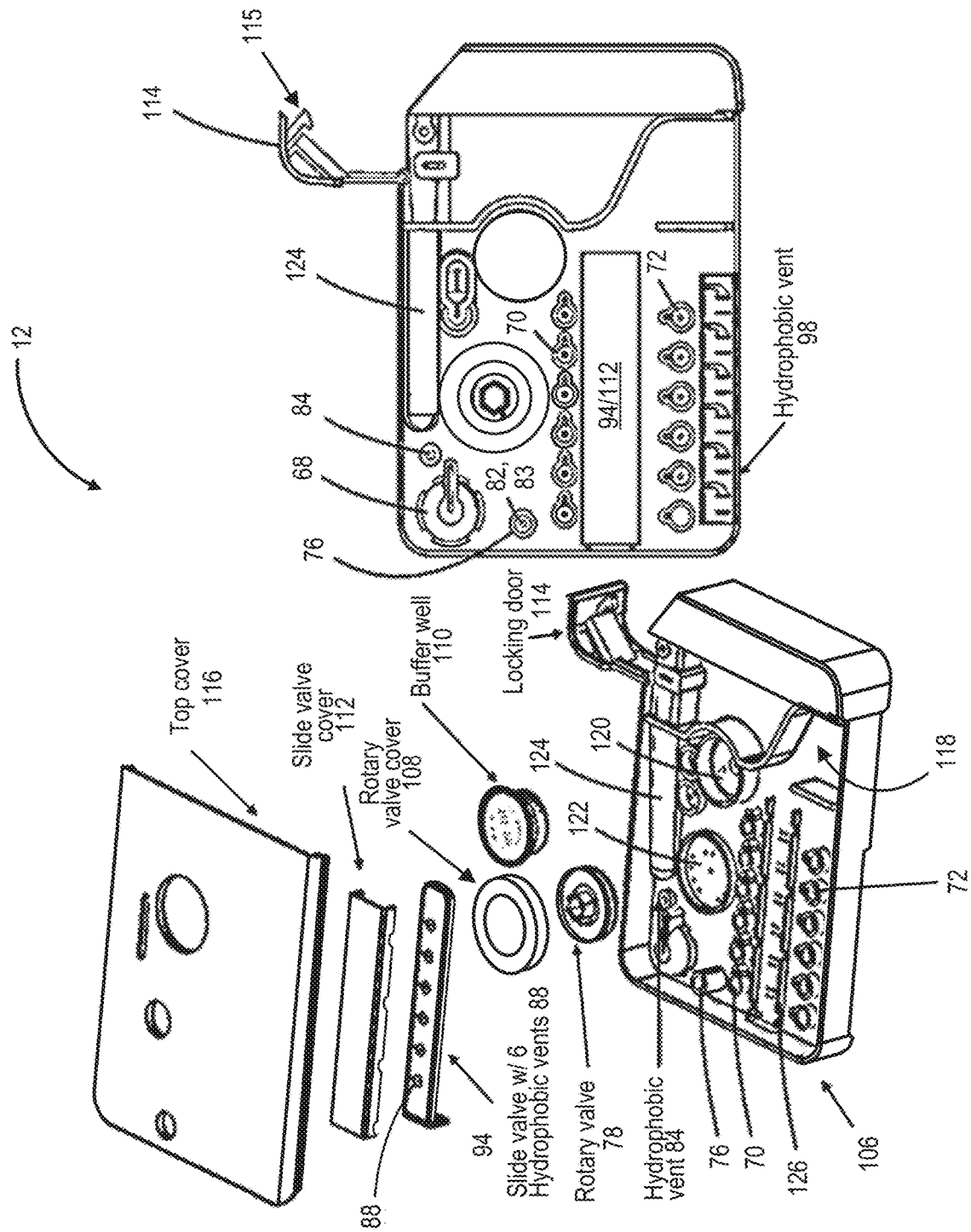
FIG. 4 is an exploded view illustration of a single-use cartridge that can be employed in the diagnostic testing system of FIG. 1.
Figure 5:
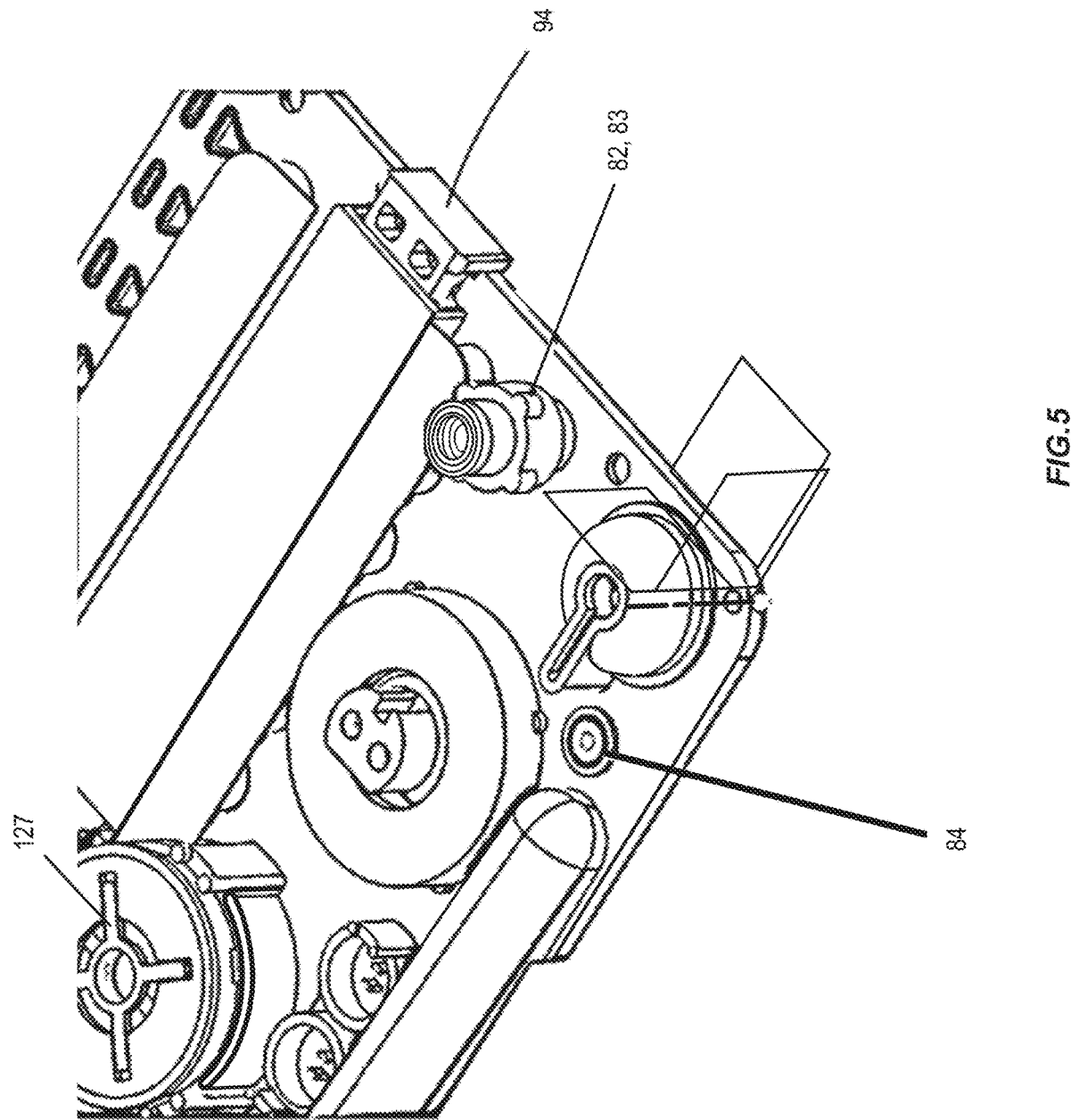
FIG. 5 is a close-up view illustration of the single-use cartridge of FIG. 4.

FIG. 4 is an exploded view illustration of the cartridge 12. The cartridge 12 includes a base assembly 106, the rotary valve 78, a rotary valve cover 108, a buffer solution chamber assembly 110, the sliding valve 94, a sliding valve cover 112, a locking door 114, and a top cover 116. The base assembly 106 includes a base panel 118 in which flow channels of the cartridge 12 are formed. The base assembly 106 also includes and/or forms at least a portion of each of a buffer well receptacle 120, a rotary valve housing 122, a swab chamber 124, the staging well 76, the actuation port 83, the amplification wells 70, a sliding valve support frame 126, the CRISP wells 72, the detection wells 74, and the detection well hydrophobic vents 98. The swab 20 is inserted into the swab chamber 124 and then enclosed in the swab chamber 124 via closing of the locking door 114, which includes a flexible latch member that engages the base assembly 106 to keep the locking door 114 shut following closure of the locking door 114. The swab 20 is inserted into the swab chamber 124 via a swab entrance. The swab chamber 124 has a suitable downward slope (e.g., 10 degrees) from the swab entrance to a distal end of the swab chamber 124 in a use orientation of the cartridge 12 (i.e., the orientation of the cartridge within the analyzer 14 with the analyzer 14 sitting on a horizontal surface). A fluid channel accommodates input of the buffer solution into the swab chamber 124. A resulting biological sample solution is removed from the distal portion of the swab chamber 124 via a suitably disposed sample solution fluid channel. The swab chamber 124 can include elongated ridges that protrude inwardly into the swab chamber 124 in the distal portion of the swab chamber 124. The elongated ridges can be configured to engage the swab head so as to form flow channels between the swab head and the swab chamber 124 that accommodate flow of the buffer solution and the resulting biological sample solution along exterior portions of the swab head. Each of the elongated ridges can extend helically around a length of the swab chamber 124. The swab chamber 124 can have any suitable downward slope. In many embodiments, the downward slope of the swab chamber 124 is in a range of 3 degrees to 20 degrees. In some embodiments, the downward slope of the elongated swab chamber 124 is in a range of 12 degrees to 18 degrees. The swab chamber 124 can have any suitable cross-sectional shape. For example, in many embodiments the swab chamber 124 has a circular cross-section. The circular cross-section can have any suitable diameter. For example, in some embodiments, the diameter of the circular cross-section is in a range from 4 mm to 8 mm. The swab chamber 124 can have any suitable height that is preferably not more than 30 mm. The buffer solution chamber assembly 110 includes a piston 127 (shown in FIG. 5) that is actuated by the clamp plunger 60 (shown in FIG. 30) during the clamping of the cartridge 12 via a clamping assembly 128 (shown in FIG. 28 and FIG. 29). FIG. 5 is a close-up view illustration of the single-use cartridge of FIG. 4.

Figure 6:
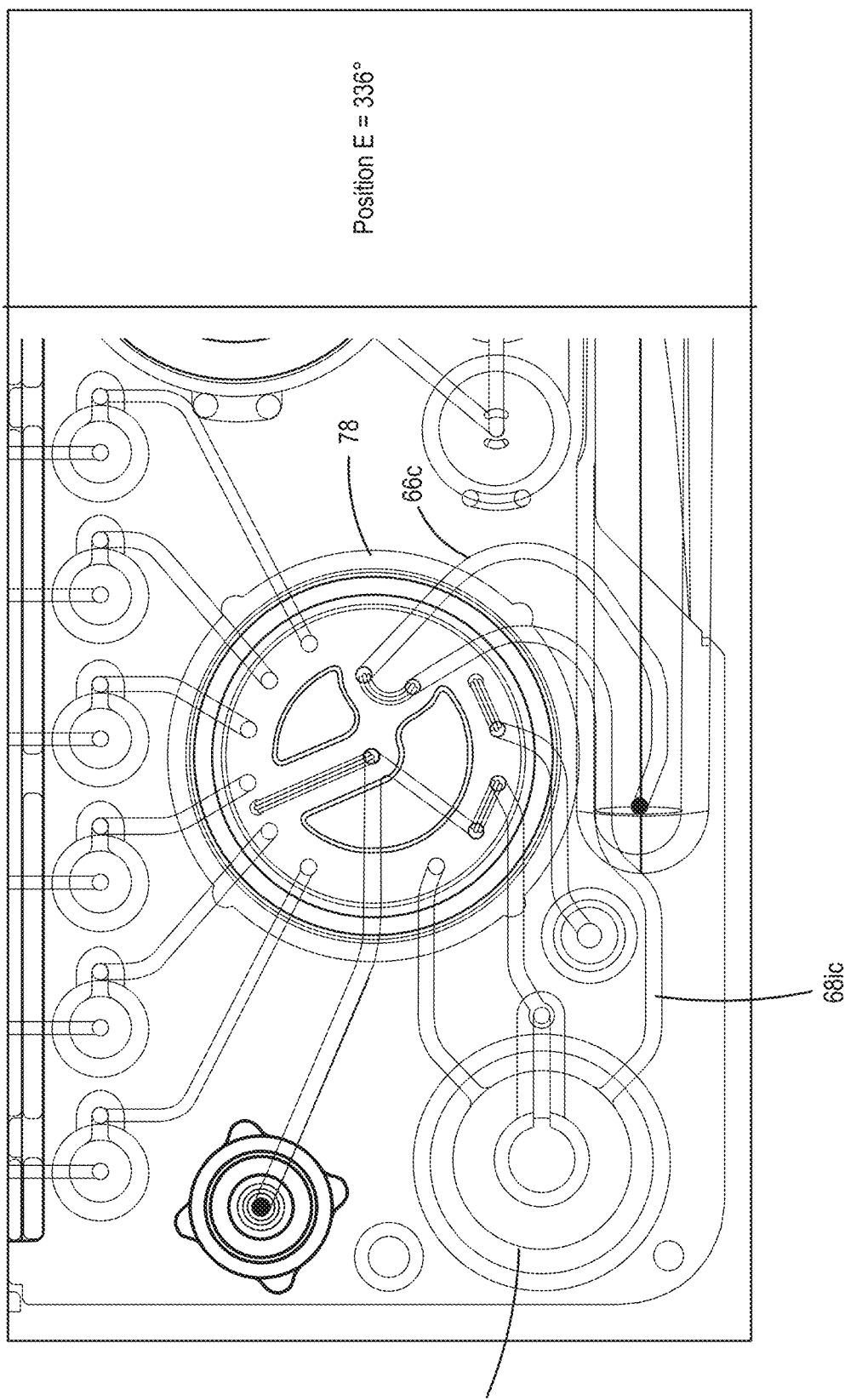
FIG. 6 is a close-up view illustration of a lysis sample solution configuration of the single-use cartridge of FIG. 4.

FIG. 6 is a close-up view illustration of a lysis sample solution configuration of the rotary valve 78. In the lysis sample solution configuration, the rotary valve 78 is in a 336 degree orientation that connects fluid channel 66c from the swab chamber 66 to fluid input channel 68ic to the lysis chamber 68, thereby fluidly connecting the swab chamber 66 to the lysis chamber 68 for transfer of the lysis sample solution from the swab chamber 66 to the lysis chamber 68.

Figure 7:
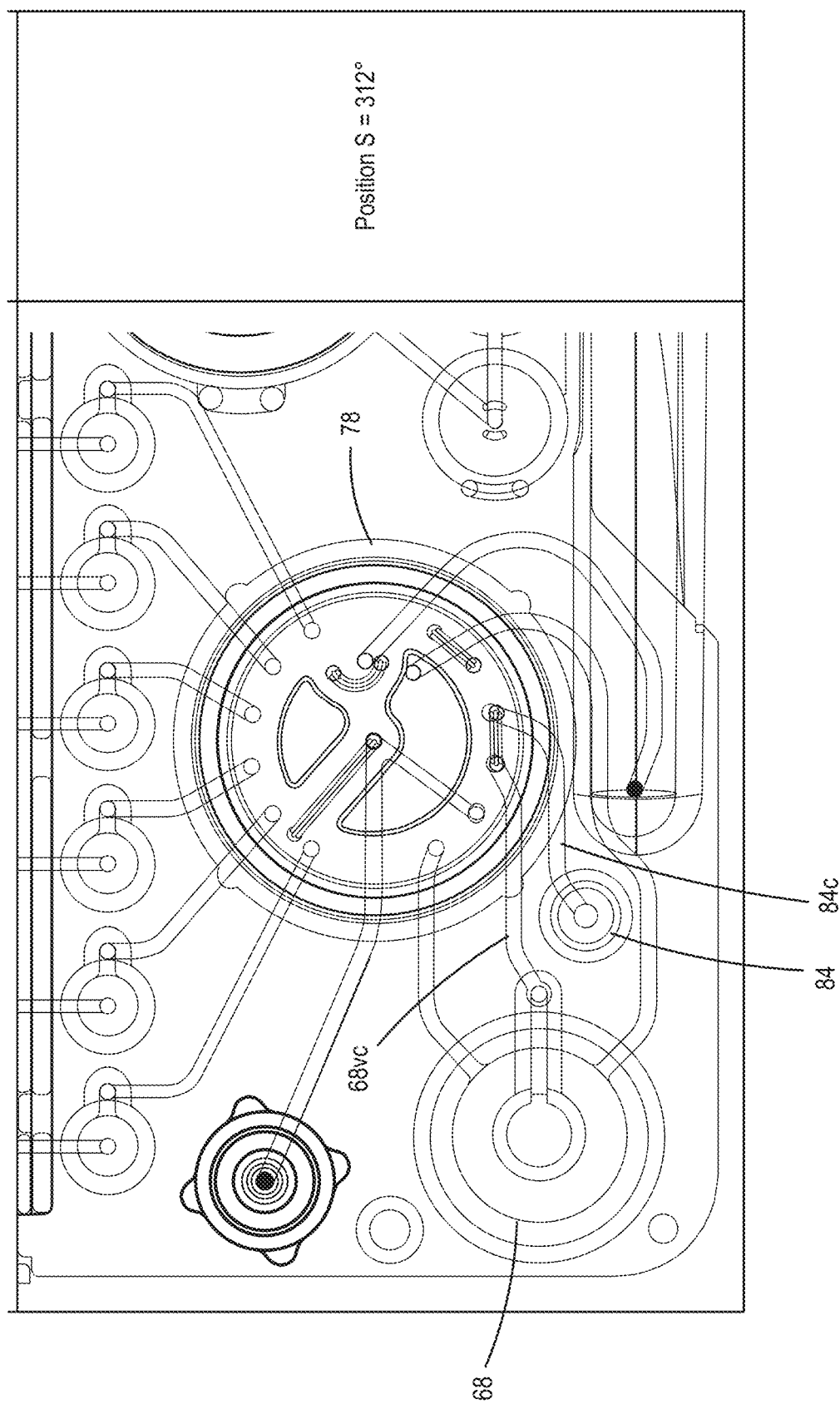
FIG. 7 is a close-up view illustration of a lysis chamber venting configuration of the single-use cartridge of FIG. 4.

FIG. 7 is a close-up view illustration of a lysis chamber venting configuration of the rotary valve 78. In the lysis chamber venting configuration, the rotary valve 78 is in a 312 degree orientation that connects fluid vent channel 68vc from the lysis chamber 68 to fluid channel 84c to the lysis chamber hydrophobic vent 84, thereby fluidly connecting the lysis chamber 68 to the lysis chamber hydrophobic vent 84 for venting of the lysis chamber 68 during the formation of the lysed sample solution in the lysis chamber 68.

Figure 8:
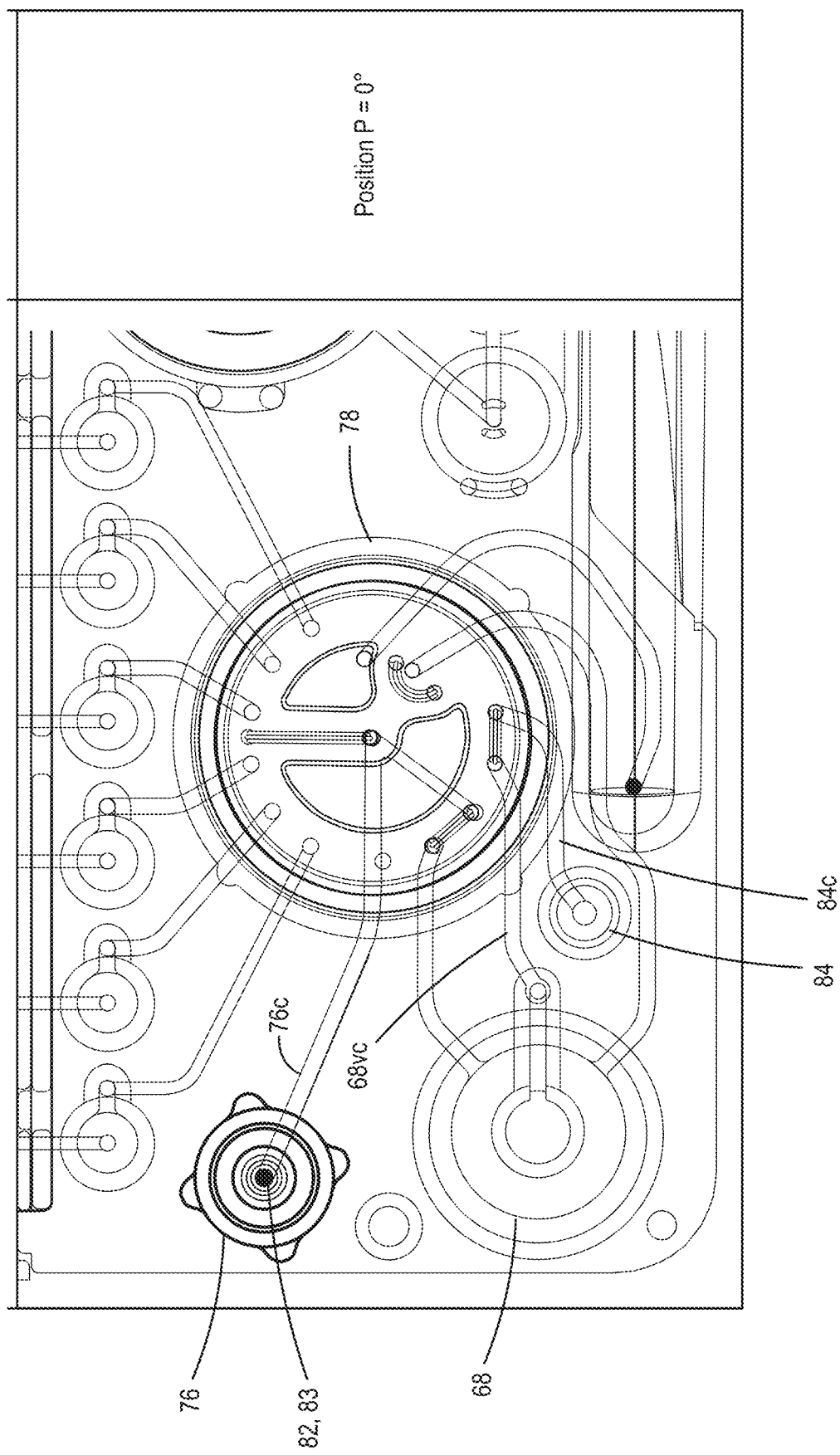
FIG. 8 is a close-up view illustration of an aliquot staging configuration of the single-use cartridge of FIG. 4.

FIG. 8 is a close-up view illustration of an aliquot staging configuration of the single-use cartridge 12. In the aliquot staging configuration, the rotary valve 78 is in a 0 degree orientation that connects a fluid output channel 68oc from the lysis chamber 68 to a fluid channel 76c to the staging well 76, thereby fluidly connecting the lysis chamber 68 to the staging well 76 for drawing an aliquot of the lysed sample solution from the lysis chamber 68 into contact with the staging well hydrophobic passage 82 via vacuum pressure applied through the staging well hydrophobic passage 82. The rotary valve 78 also connects fluid channel 68vc from the lysis chamber 68 to the fluid channel 84c to the lysis chamber vent 84 to supply air to replace the aliquot drawn from the lysis chamber 68. In many embodiments, the aliquot staging configuration is used multiple time to stage respective aliquots of the lysed sample solution from the lysis chamber 68 to the staging well 76.

Figure 9:
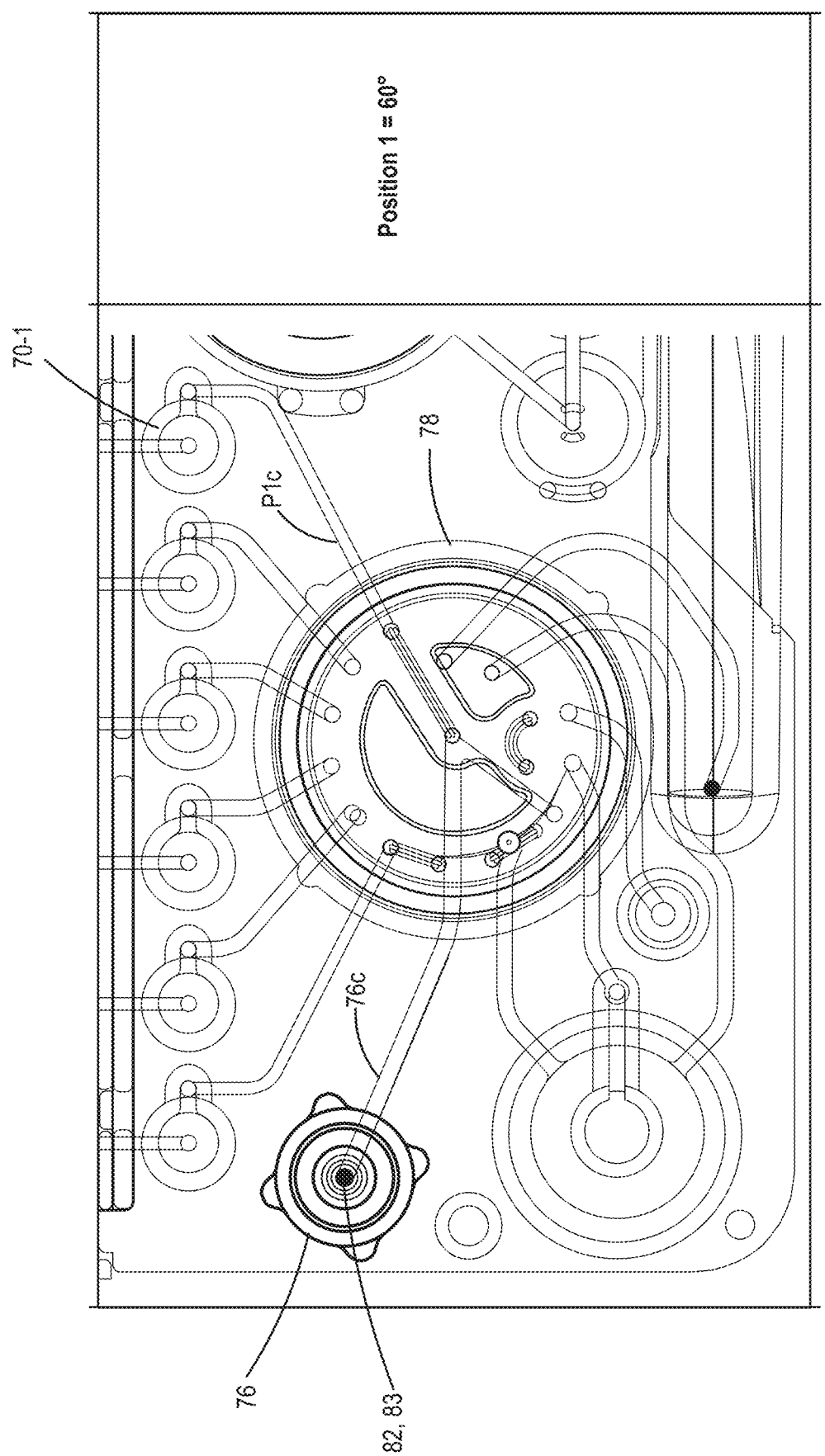
FIG. 9 and FIG. 10 are close-up view illustrations of a first processing channel configuration of the single-use cartridge of FIG. 4.
Figure 10:
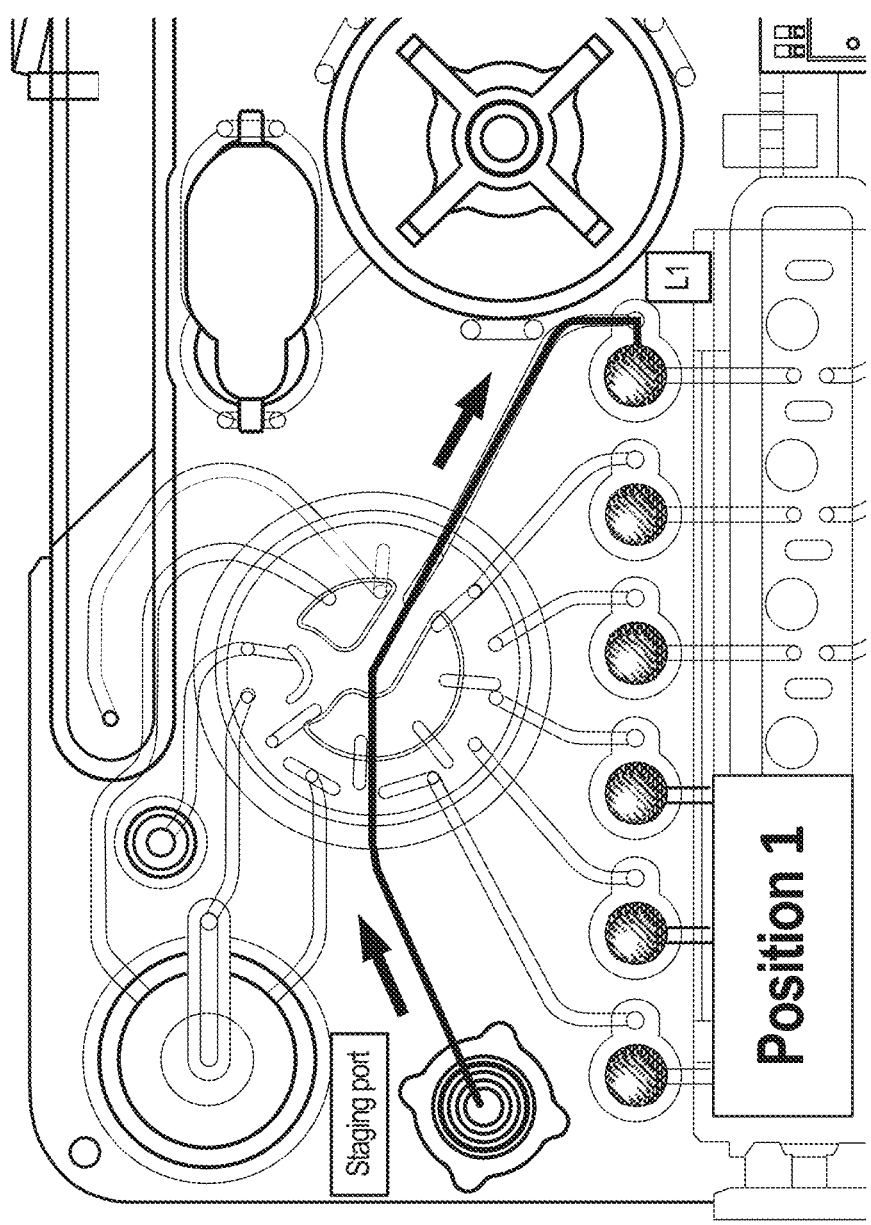

FIG. 9 and FIG. 10 are close-up view illustrations of a first processing channel configuration of the single-use cartridge 12. In the first processing channel configuration, the rotary valve 78 is in a 60 degree orientation that connects fluid channel 76c from the staging well 76 to fluid channel P1c to the first processing channel amplification well 70-1 for transfer of a first aliquot of the lysed sample solution from the staging well 76 to the first processing channel amplification well 70-1 and into contact with the first processing channel amplification well hydrophobic vent 88-1. The first processing channel configuration of the rotary valve 78 is also used to push liquid from the first processing channel amplification well 70-1 to the first processing channel CRISP well 72-1 and to push liquid from the first processing channel CRISPR well 72-1 to the first processing channel detection well 74-1.

Figure 11:
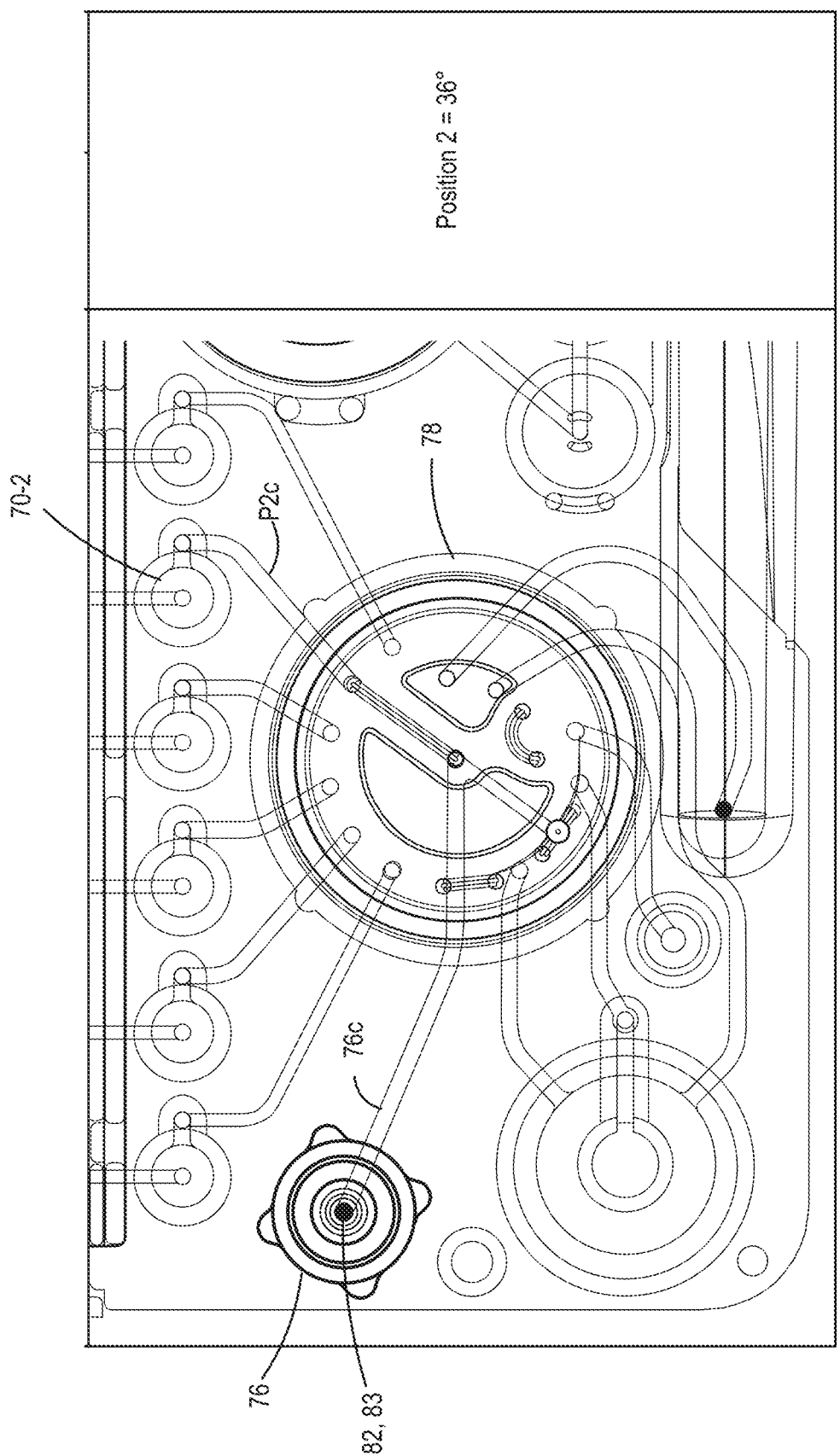
FIG. 11 and FIG. 12 are close-up view illustrations of a second processing channel configuration of the single-use cartridge of FIG. 4.
Figure 12:
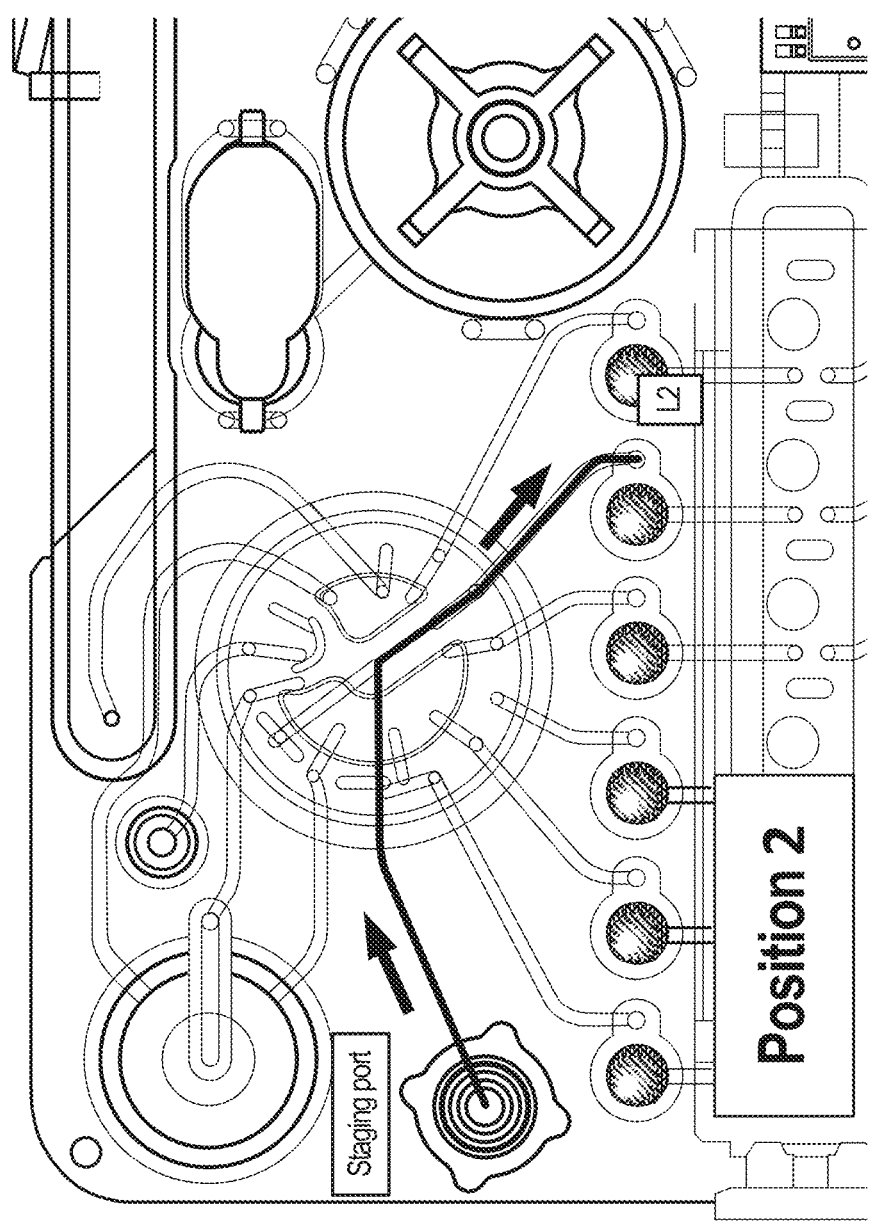

FIG. 11 and FIG. 12 are close-up view illustrations of a second processing channel configuration of the rotary valve 78. In the second processing channel configuration, the rotary valve 78 is in a 36 degree orientation that connects fluid channel 76c from the staging well 76 to fluid channel P2c to the second processing channel amplification well 70-2 for transfer of a second aliquot of the lysed sample solution from the staging well 76 to the second processing channel amplification well 70-2 and into contact with the second processing channel amplification well hydrophobic vent 88-2. The second processing channel configuration of the rotary valve 78 is also used to push liquid from the second processing channel amplification well 70-2 to the second processing channel CRISP well 72-2 and to push liquid from the second processing channel CRISPR well 72-2 to the second processing channel detection well 74-2.

Figure 13:
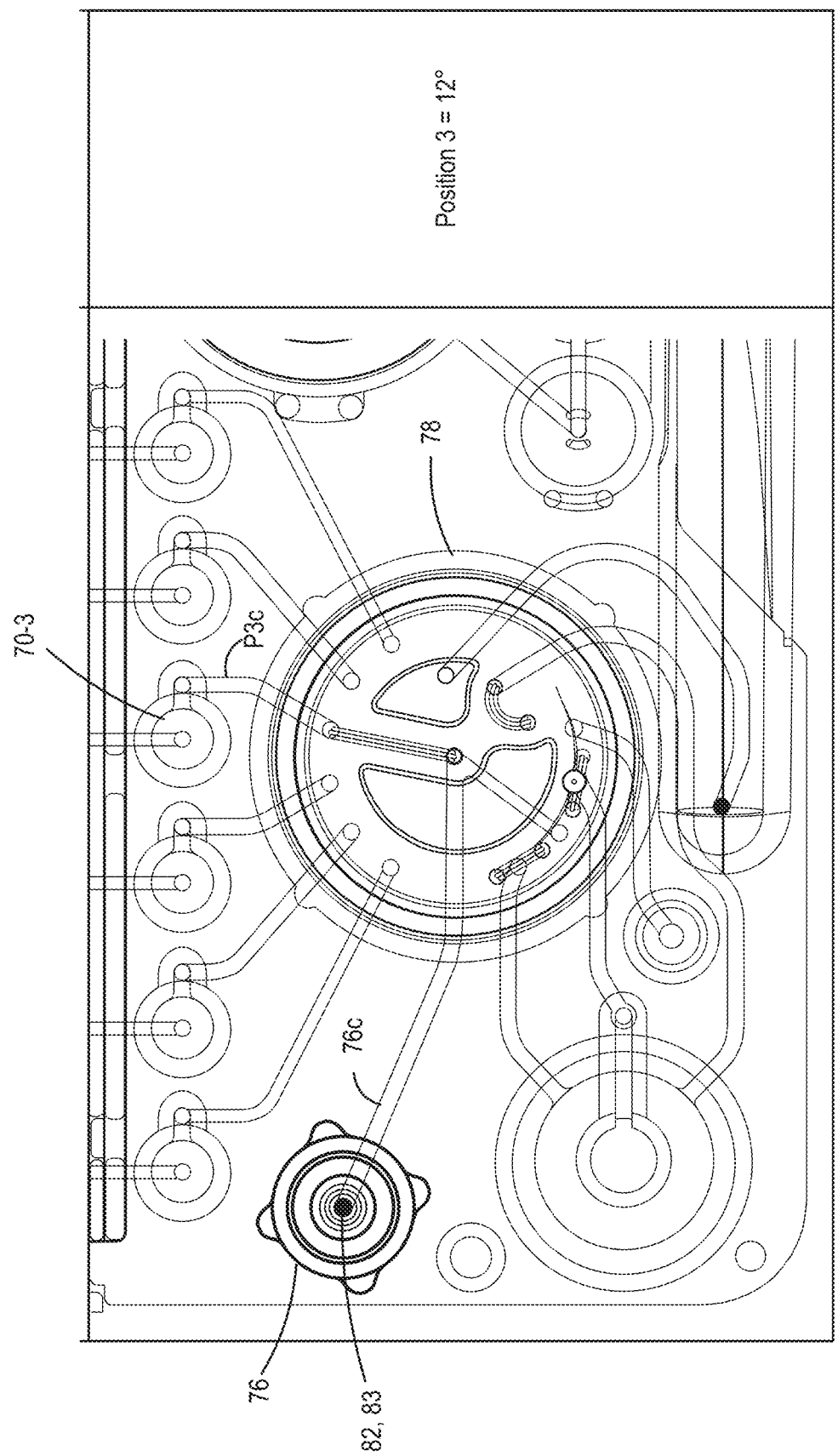
FIG. 13 and FIG. 14 are close-up view illustrations of a third processing channel configuration of the single-use cartridge of FIG. 4.
Figure 14:
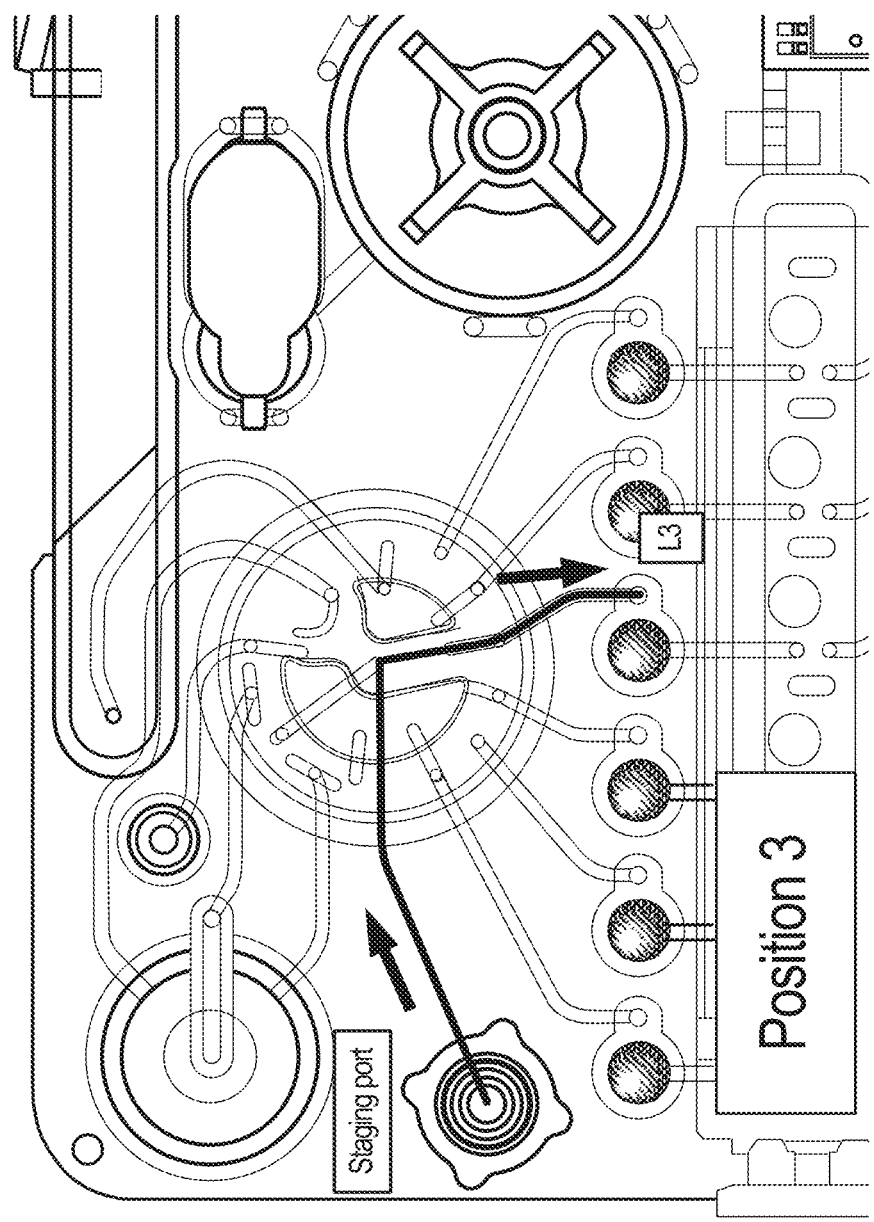

FIG. 13 and FIG. 14 are close-up view illustrations of a third processing channel configuration of the rotary valve 78. In the third processing channel configuration, the rotary valve 78 is in a 12 degree orientation that connects fluid channel 76c from the staging well 76 to fluid channel P3c to the third processing channel amplification well 70-3 for transfer of a third aliquot of the lysed sample solution from the staging well 76 to the third processing channel amplification well 70-3 and into contact with the third processing channel amplification well hydrophobic vent 88-3. The third processing channel configuration of the rotary valve 78 is also used to push liquid from the third processing channel amplification well 70-3 to the third processing channel CRISP well 72-3 and to push liquid from the third processing channel CRISPR well 72-3 to the third processing channel detection well 74-3.

Figure 15:
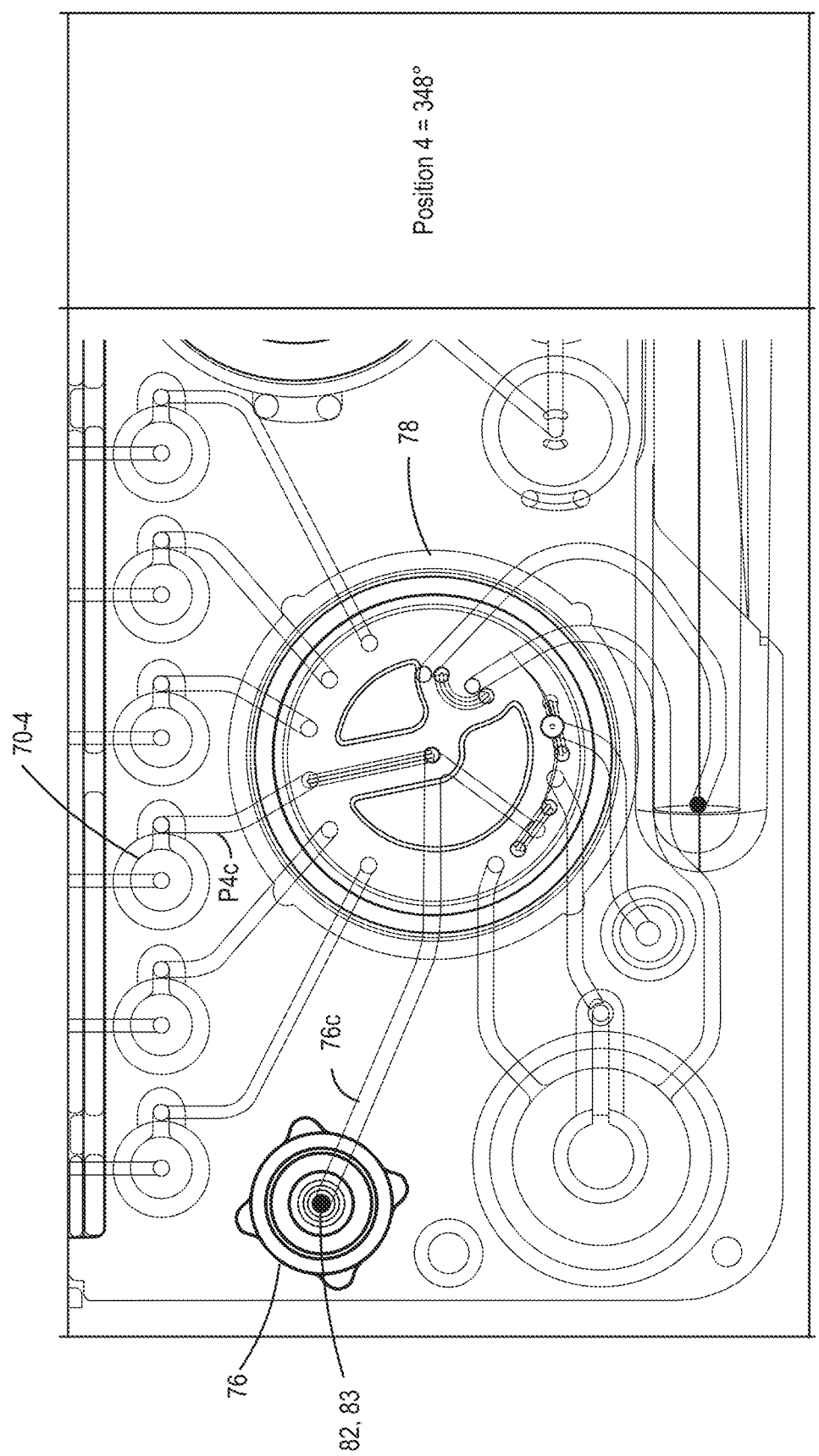
FIG. 15 and FIG. 16 are close-up view illustrations of a fourth processing channel configuration of the single-use cartridge of FIG. 4.
Figure 16:
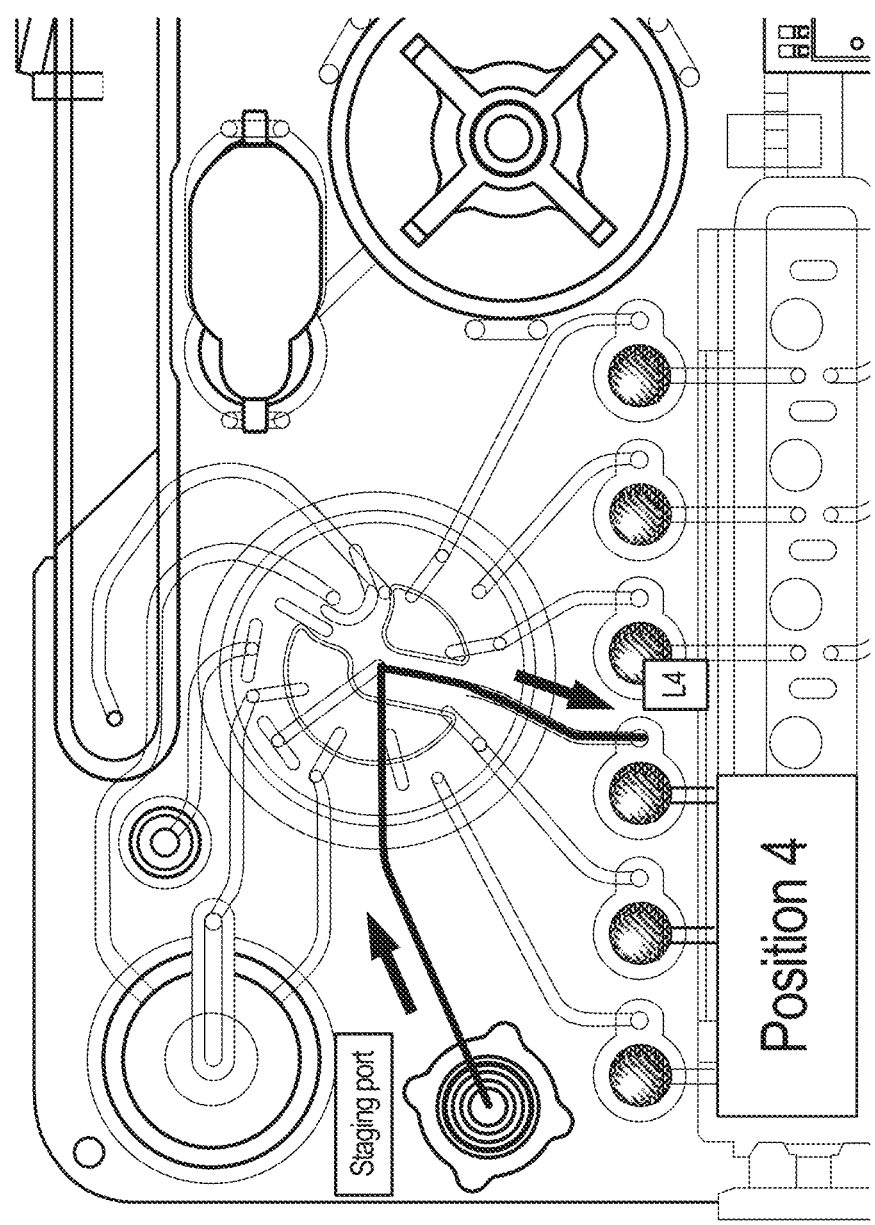

FIG. 15 and FIG. 16 are close-up view illustrations of a fourth processing channel configuration of the rotary valve 78. In the fourth processing channel configuration, the rotary valve 78 is in a 348 degree orientation that connects fluid channel 76c from the staging well 76 to fluid channel P4c to the fourth processing channel amplification well 70-4 for transfer of a fourth aliquot of the lysed sample solution from the staging well 76 to the fourth processing channel amplification well 70-4 and into contact with the fourth processing channel amplification well hydrophobic vent 88-4. The fourth processing channel configuration of the rotary valve 78 is also used to push liquid from the fourth processing channel amplification well 70-4 to the fourth processing channel CRISP well 72-4 and to push liquid from the fourth processing channel CRISPR well 72-4 to the fourth processing channel detection well 74-4.

Figure 17:
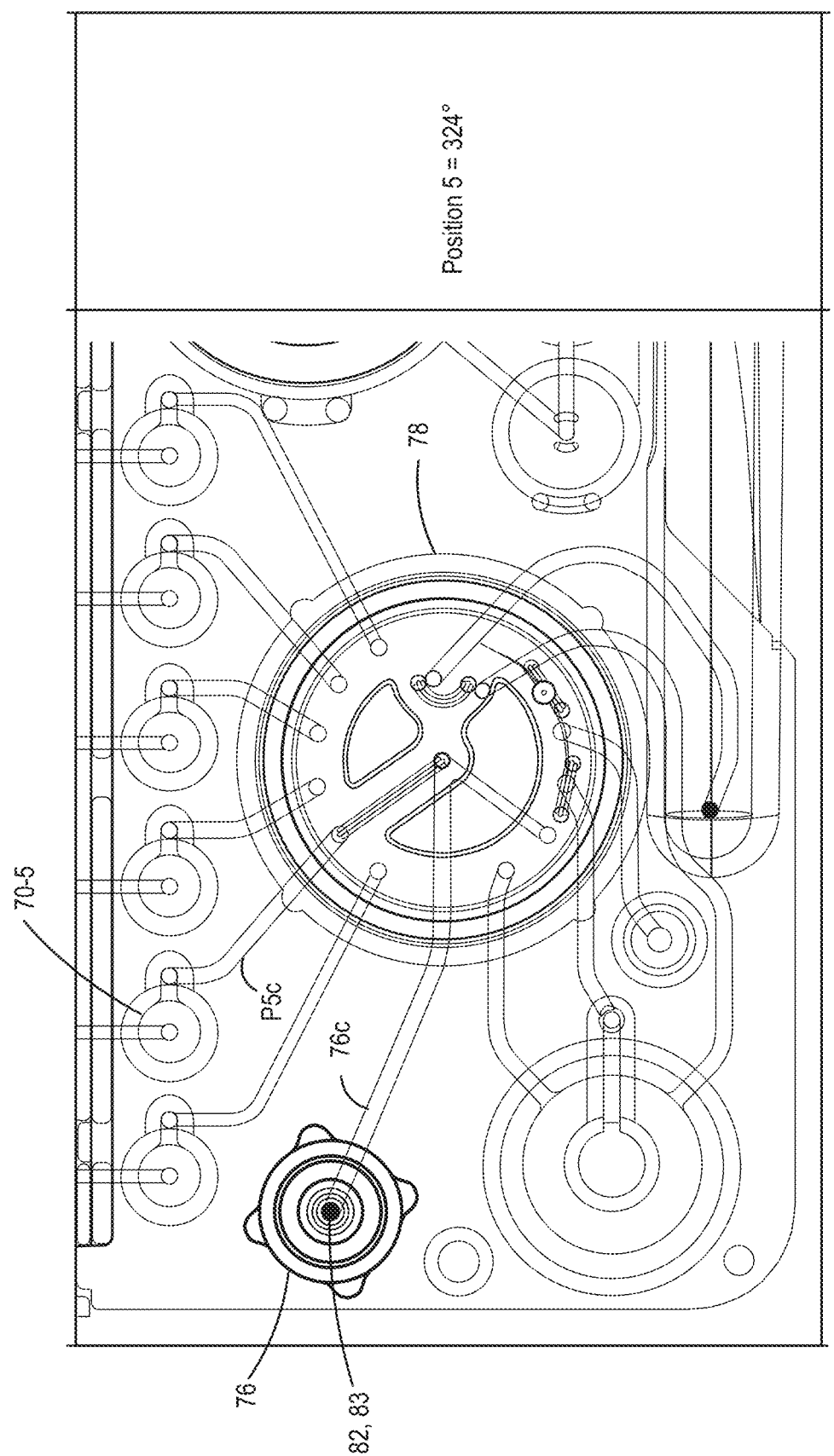
FIG. 17 and FIG. 18 are close-up view illustrations of a fifth processing channel configuration of the single-use cartridge of FIG. 4.
Figure 18:
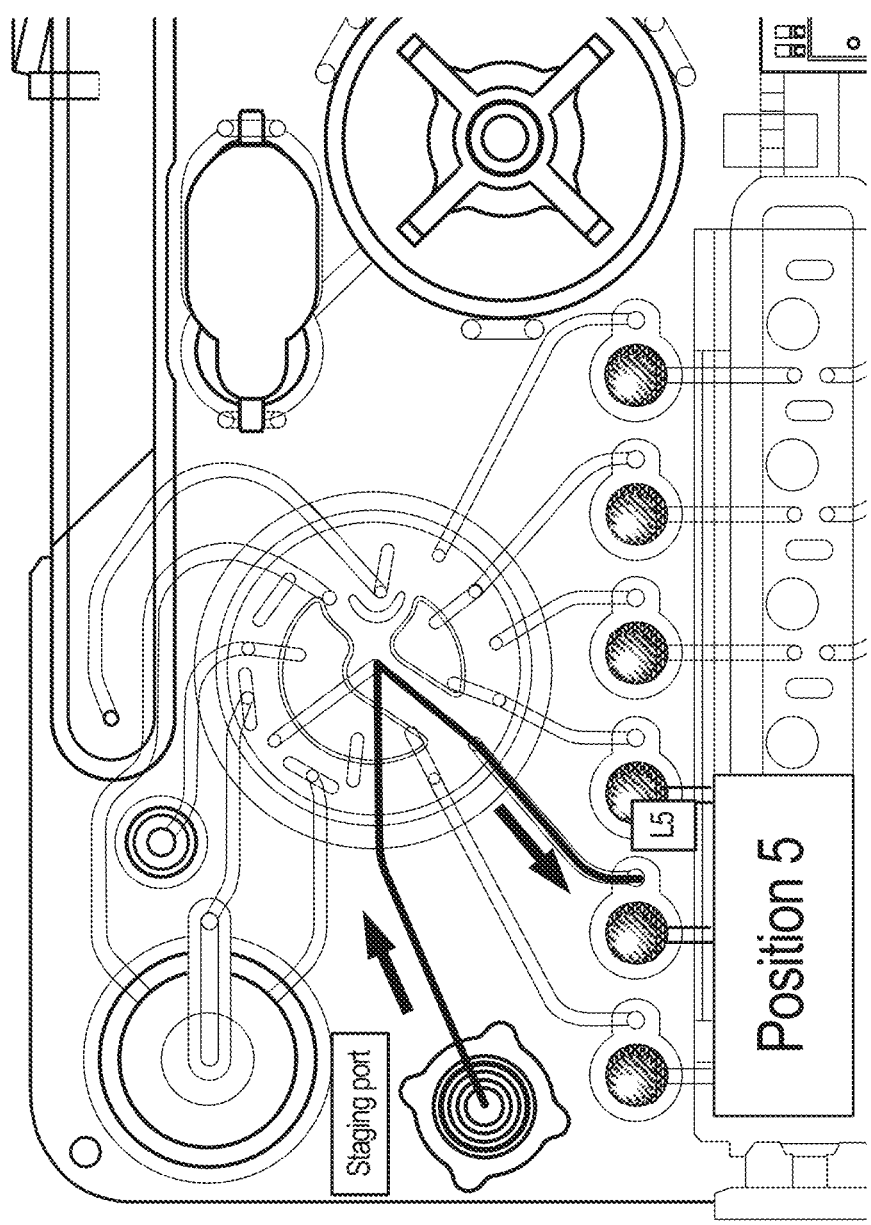

FIG. 17 and FIG. 18 are close-up view illustrations of a fifth processing channel configuration of the rotary valve 78. In the fifth processing channel configuration, the rotary valve 78 is in a 324 degree orientation that connects fluid channel 76c from the staging well 76 to fluid channel P5c to the fifth processing channel amplification well 70-5 for transfer of a fifth aliquot of the lysed sample solution from the staging well 76 to the fifth processing channel amplification well 70-5 and into contact with the fifth processing channel amplification well hydrophobic vent 88-5. The fifth processing channel configuration of the rotary valve 78 is also used to push liquid from the fifth processing channel amplification well 70-5 to the fifth processing channel CRISP well 72-5 and to push liquid from the fifth processing channel CRISPR well 72-5 to the fifth processing channel detection well 74-5.

Figure 19:
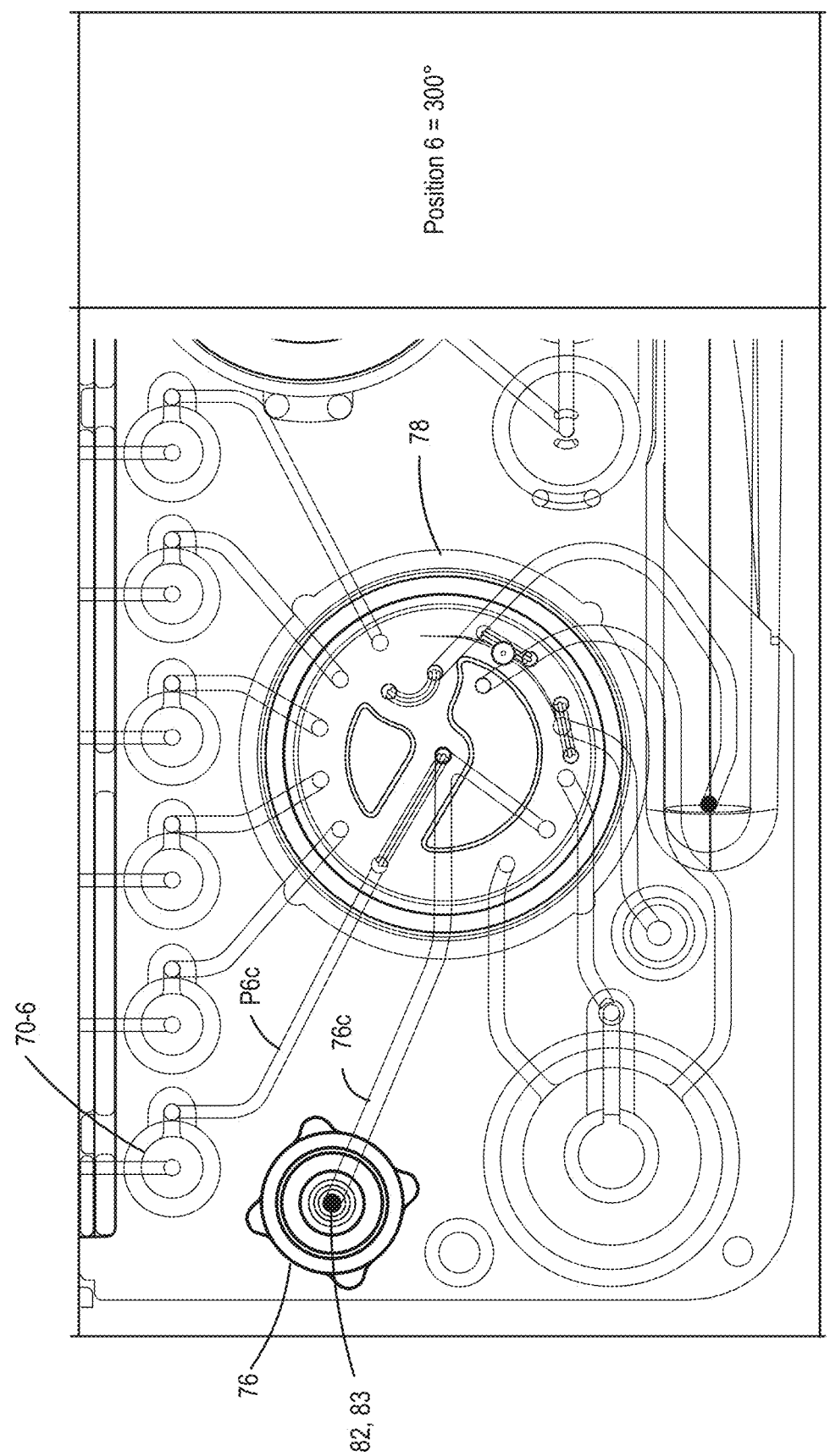
FIG. 19 and FIG. 20 are close-up view illustrations of a sixth processing channel configuration of the single-use cartridge of FIG. 4.
Figure 20:
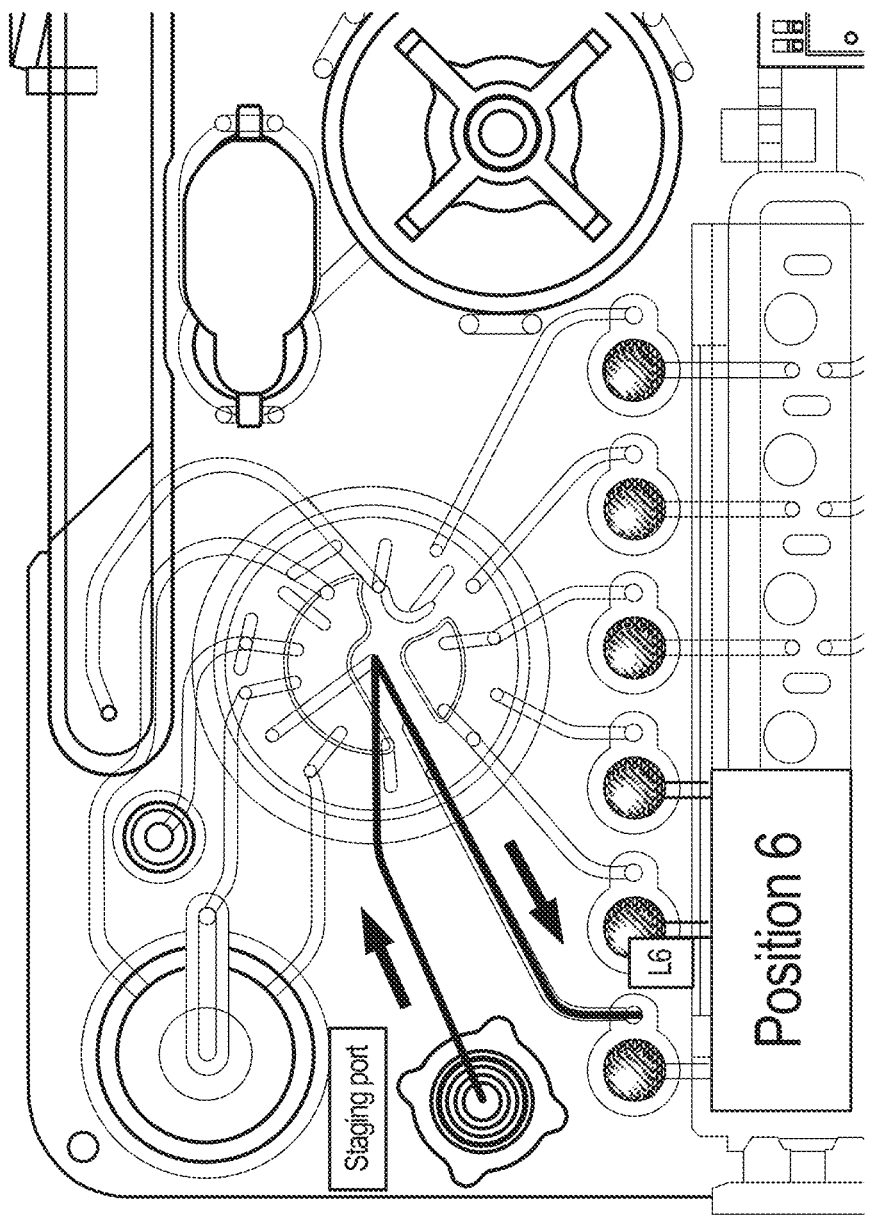

FIG. 19 and FIG. 20 are close-up view illustrations of a sixth processing channel configuration of the rotary valve 78. In the sixth processing channel configuration, the rotary valve 78 is in a 300 degree orientation that connects fluid channel 76c from the staging well 76 to fluid channel P6c to the sixth processing channel amplification well 70-6 for transfer of a sixth aliquot of the lysed sample solution from the staging well 76 to the sixth processing channel amplification well 70-6 and into contact with the sixth processing channel amplification well hydrophobic vent 88-6. The sixth processing channel configuration of the rotary valve is also used to push liquid from the sixth processing channel amplification well 70-6 to the sixth processing channel CRISP well 72-6 and to push liquid from the sixth processing channel CRISPR well 72-6 to the sixth processing channel detection well 74-6.

Figure 21:
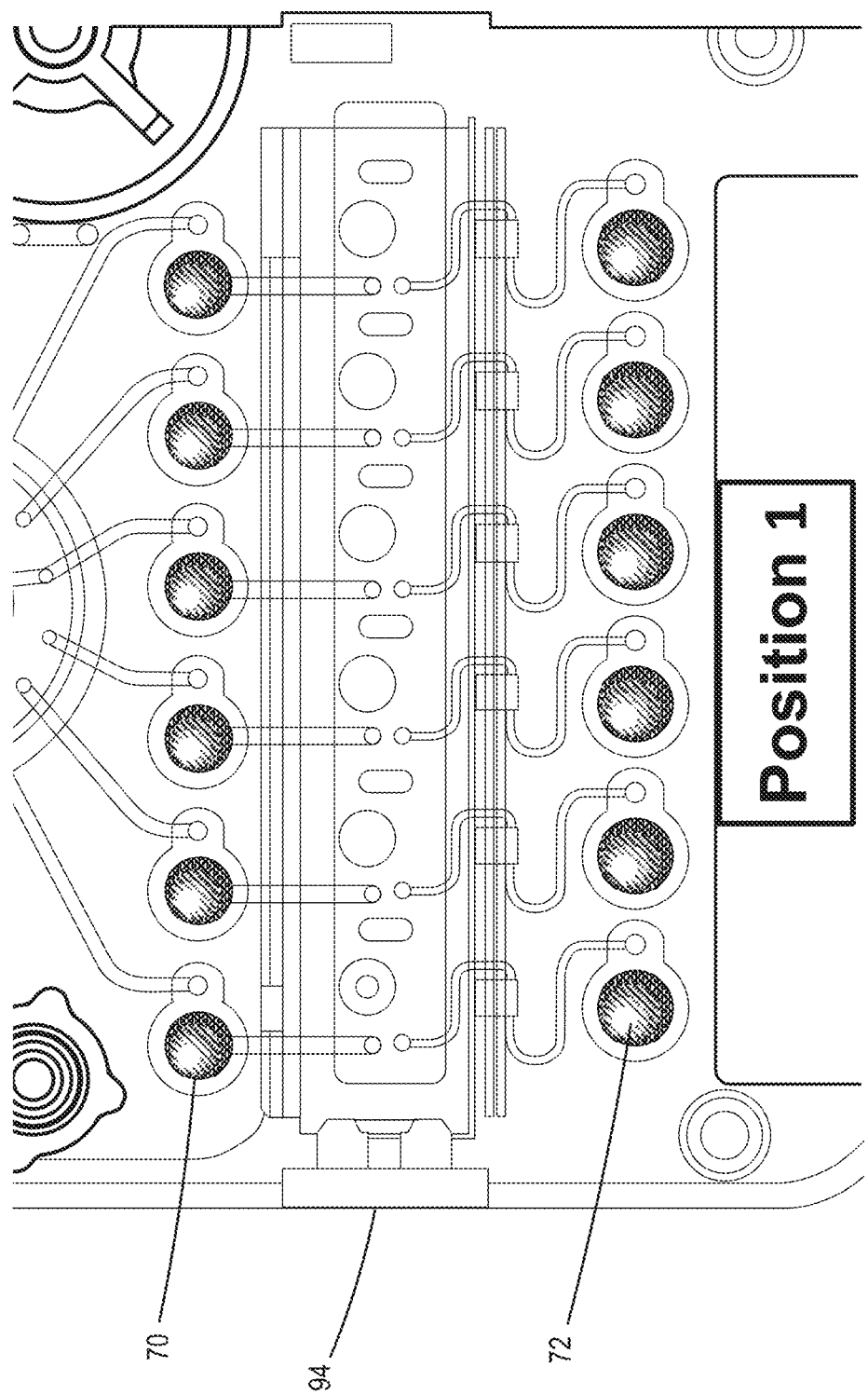
FIG. 21 is a close-up view illustration of a shipping configuration of a sliding valve assembly of the single-use cartridge of FIG. 4.
Figure 22:
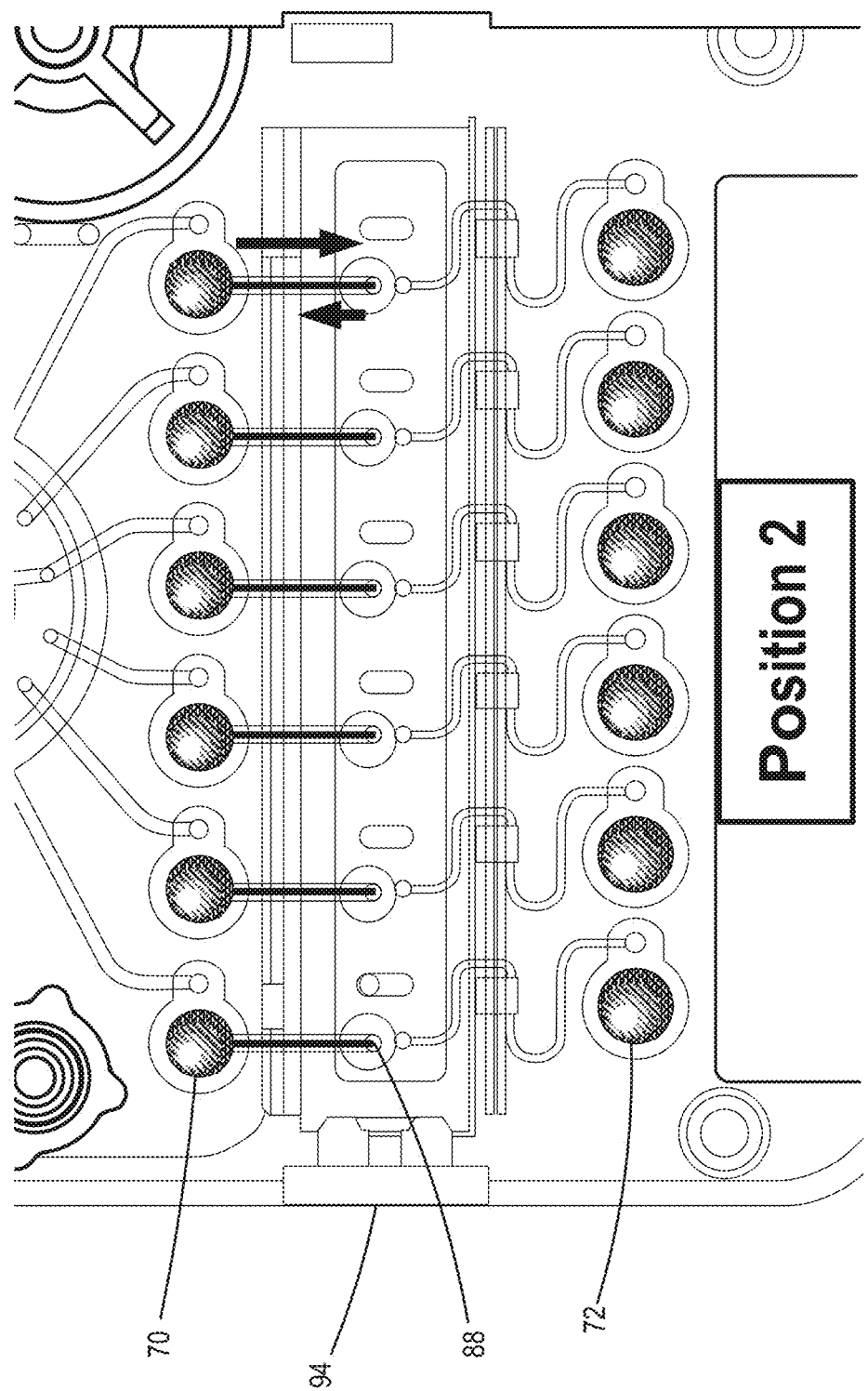
FIG. 22 is a close-up view illustration of a blocking configuration of the sliding valve assembly of the single-use cartridge of FIG. 4.
Figure 23:
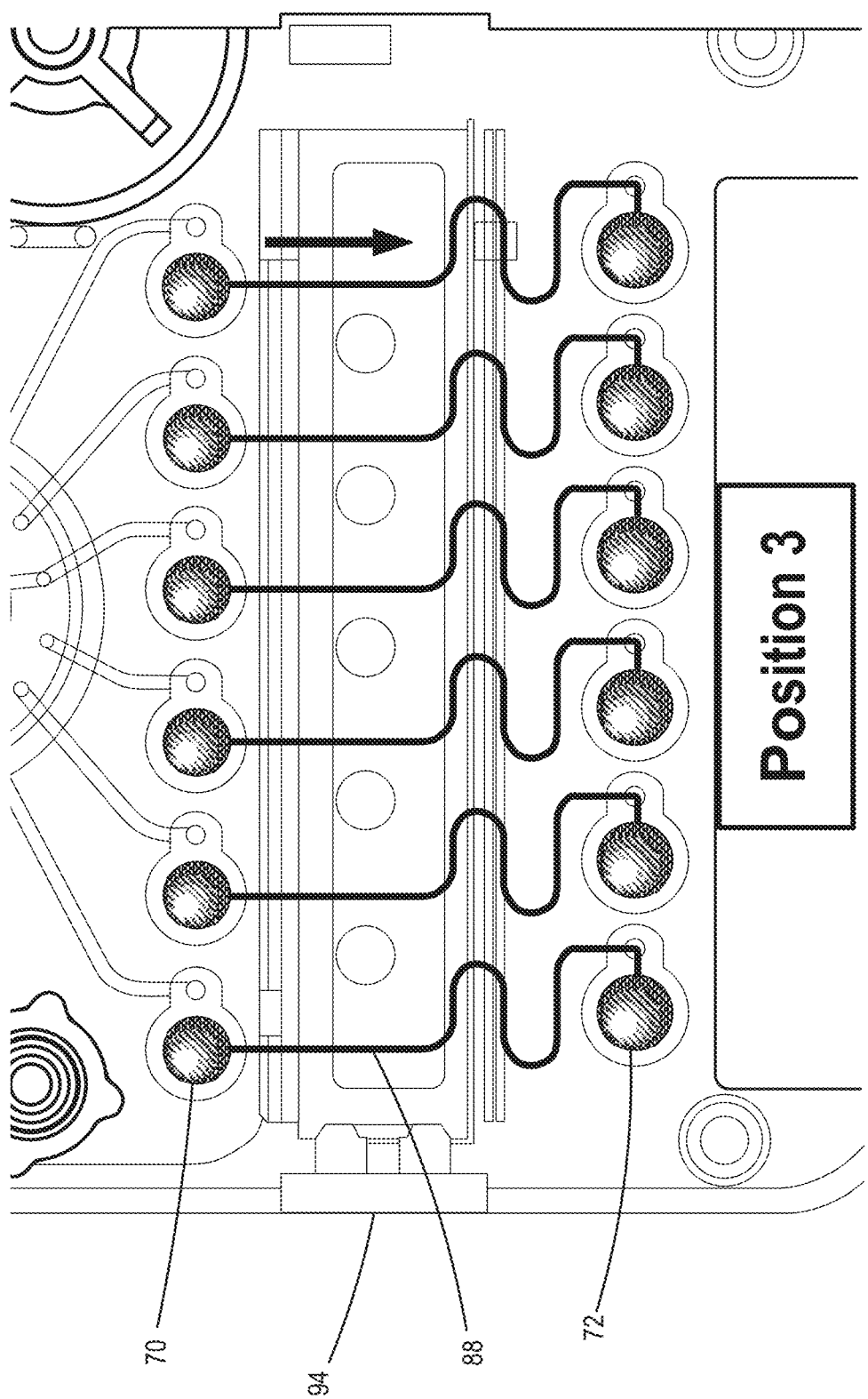
FIG. 23 is a close-up view illustration of a transfer configuration of the sliding valve assembly of the single-use cartridge of FIG. 4.

FIG. 21 is a close-up view illustration of a shipping configuration of a sliding valve assembly of the single-use cartridge of FIG. 4. FIG. 22 is a close-up view illustration of a blocking configuration of the sliding valve assembly of the single-use cartridge of FIG. 4. FIG. 23 is a close-up view illustration of a transfer configuration of the sliding valve assembly of the single-use cartridge of FIG. 4.

Figure 24:
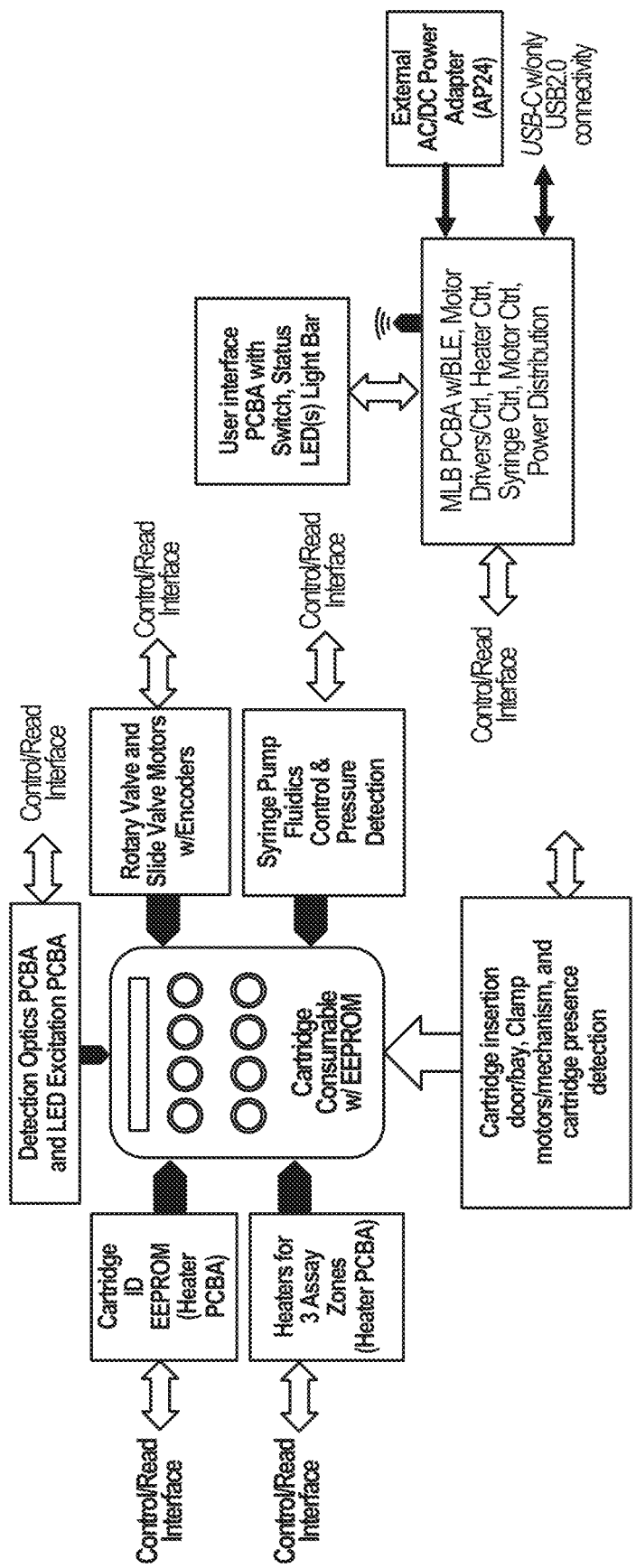
FIG. 24 is a schematic diagram illustrating aspects of an example portable analyzer of the diagnostic testing system of FIG. 1.
Figure 25:
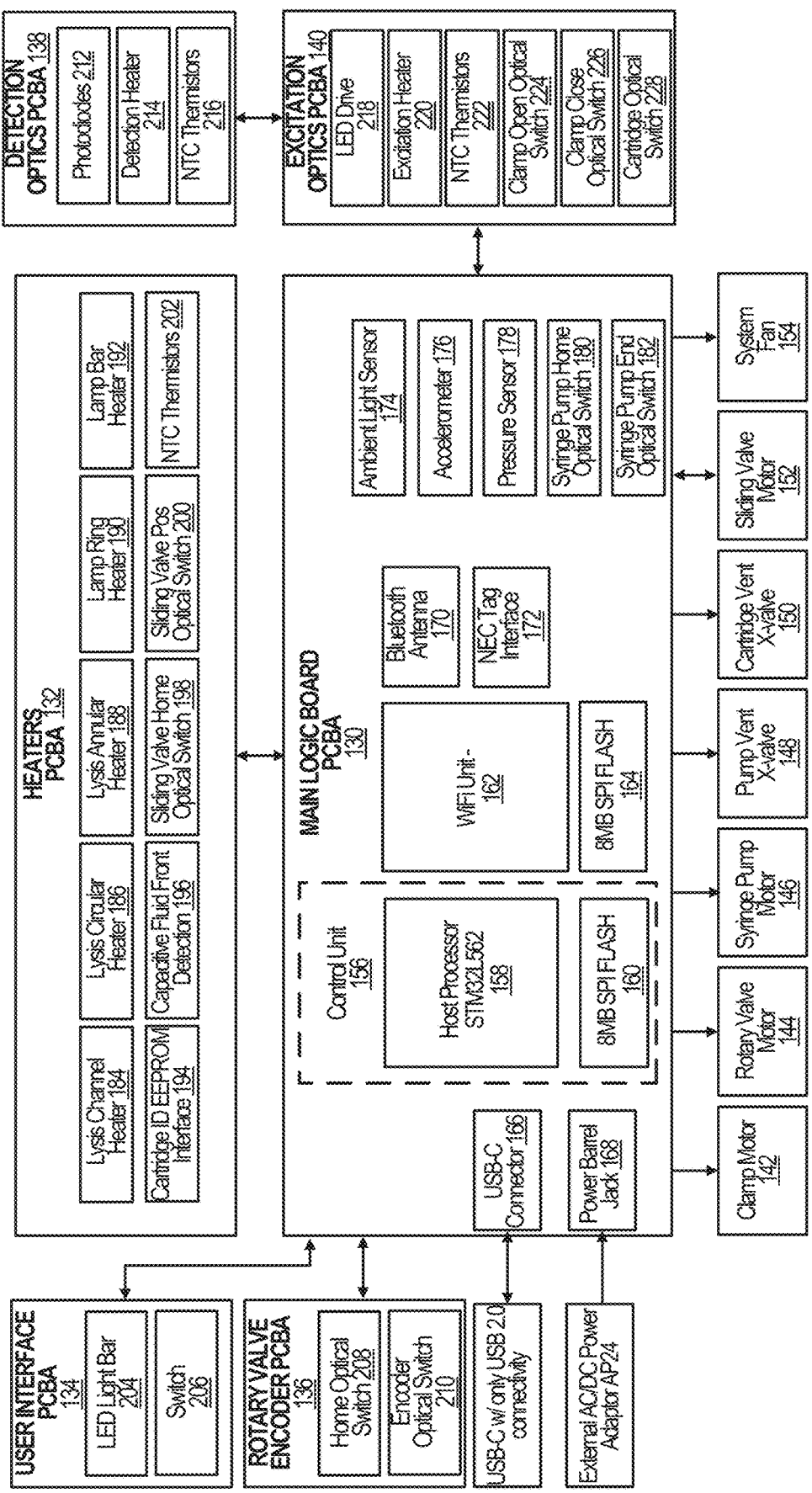
FIG. 25 is a block diagram illustrating aspects of the portable analyzer of FIG. 5.

FIG. 24 and FIG. 25 are schematic diagrams illustrating cartridge operation and related control aspects and components of the analyzer 14. The analyzer 14 includes a main logic board printed circuit board assembly (PCBA) 130, a heaters PCBA 132, a user interface PCBA 134, a rotary valve encoder PCBA 136, a detection optics PCBA 138, an excitation optics PCBA 140, a clamp motor 142, a rotary valve motor 144, a pump assembly motor 146, a pump vent x-valve 148, a cartridge vent x-valve 150, a sliding valve motor 152, and a system fan 154. The main logic circuit board PCBA 130 includes a control unit 156 that controls the operation of the various components of the analyzer 14. The control unit 156 includes a processor 158 and flash memory 160 that stores instructions executable by the processor 158 for the control of the various components of the analyzer 14. The main logic circuit board PCBA 130 further includes a wireless Bluetooth unit 162, wireless Bluetooth unit flash memory 164, a Universal Serial Bus Type C (USB-C) connector 166, a power jack 168, a Bluetooth antenna 170, a near-field communication (NFC) tag interface 172, an ambient light sensor 174, an accelerometer 176, a pressure sensor 178, a syringe pump home optical sensor 180, and a pump assembly end optical sensor 182. The heaters PCBA 132 includes a lysis channel heater 184, a lysis circular heater 186, a lysis annular heater 188, amplification well ring heaters 190, amplification well bar heaters 192, a cartridge identification (ID) electronically erasable programmable read-only memory (EEPROM) interface 194, a capacitive fluid front detection 196, a sliding valve home optical switch 198, a sliding valve position optical switch 200, and thermally sensitive resisters (aka NTC thermistors) 202. The user interface PCBA 134 includes a light emitting diode (LED) light bar 204 and an on/off switch 206. The rotary valve encoder PCBA 136 includes a home optical switch 208 and an encoder optical switch 210. The detection optics PCBA includes a detection photodiode analogue front end (AFE) 212, a detection well heating assembly 214, and NTC thermistors 216. The excitation optics PCBA 140 includes an LED drive 218, an excitation heater 220, NTC thermistors 222, a clamp open optical switch 224, a clamp closed optical switch 226, and a cartridge optical switch 228. As illustrated in FIG. 25, there are many interfaces between the analyzer 14 and the cartridge 12 including heaters, excitation optics, detection optics, rotary and slider valve actuation, cartridge clamping mechanism, and related sensors.

Figure 26:
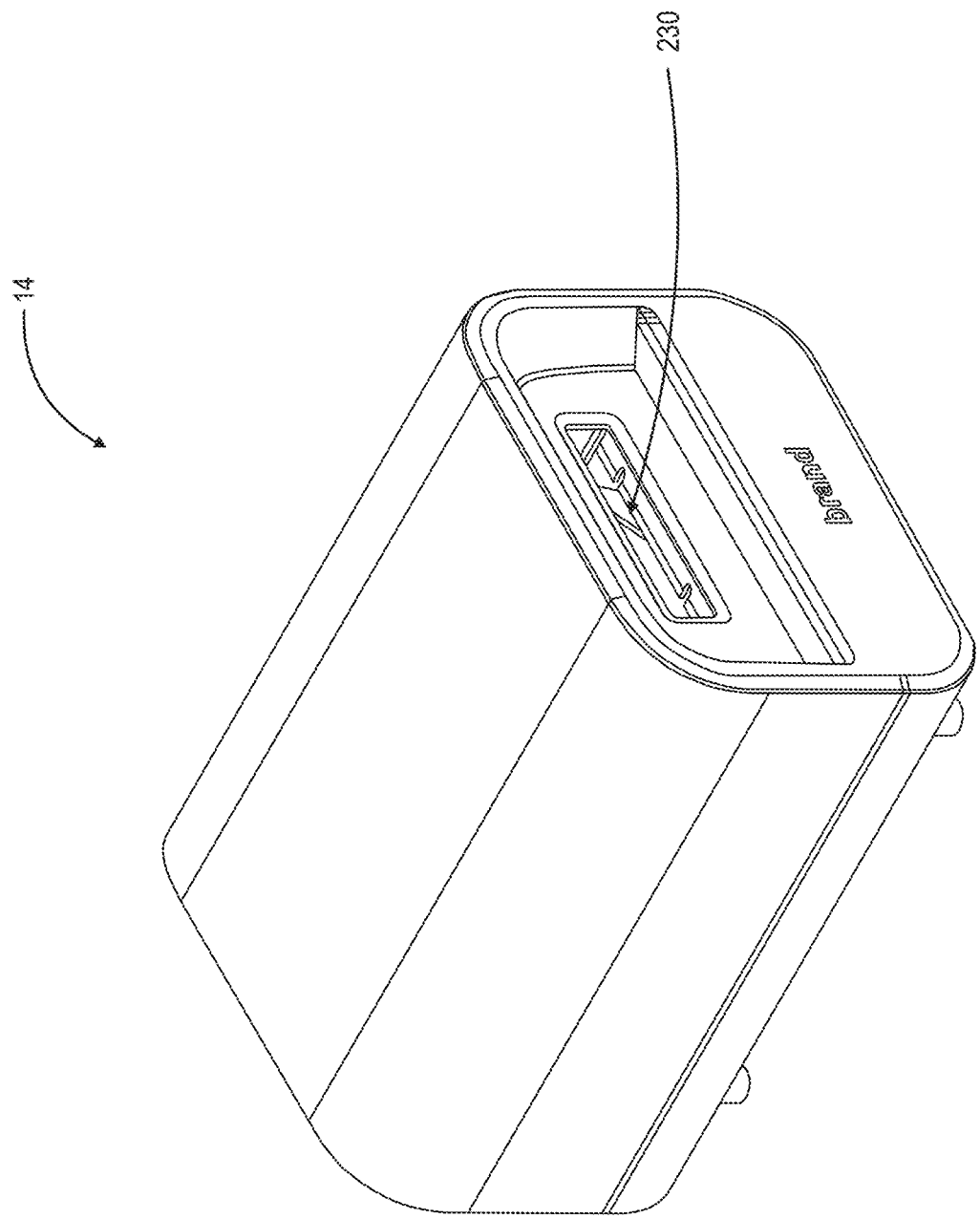
FIG. 26 is an external view illustrating an embodiment of the portable analyzer of FIG. 5.

FIG. 26 shows an external view of the analyzer 14. The analyzer 14 has a slot 230 for insertion of the cartridge 12. In many embodiments, the cartridge 12 and the slot 230 are shaped to prevent insertion of the cartridge 12 in the wrong direction and/or orientation. The analyzer 14 has a spring-loaded door that automatically closes whenever a cartridge 12 is not inserted in the analyzer 14. The analyzer 14 can be configured to detect if the cartridge swab entrance door is completely closed and sealed, output an alert if the cartridge swab entrance door is not completely closed and sealed, and not proceed with operation of the cartridge 12 if the cartridge swab door is not completely closed and sealed.

Figure 27:
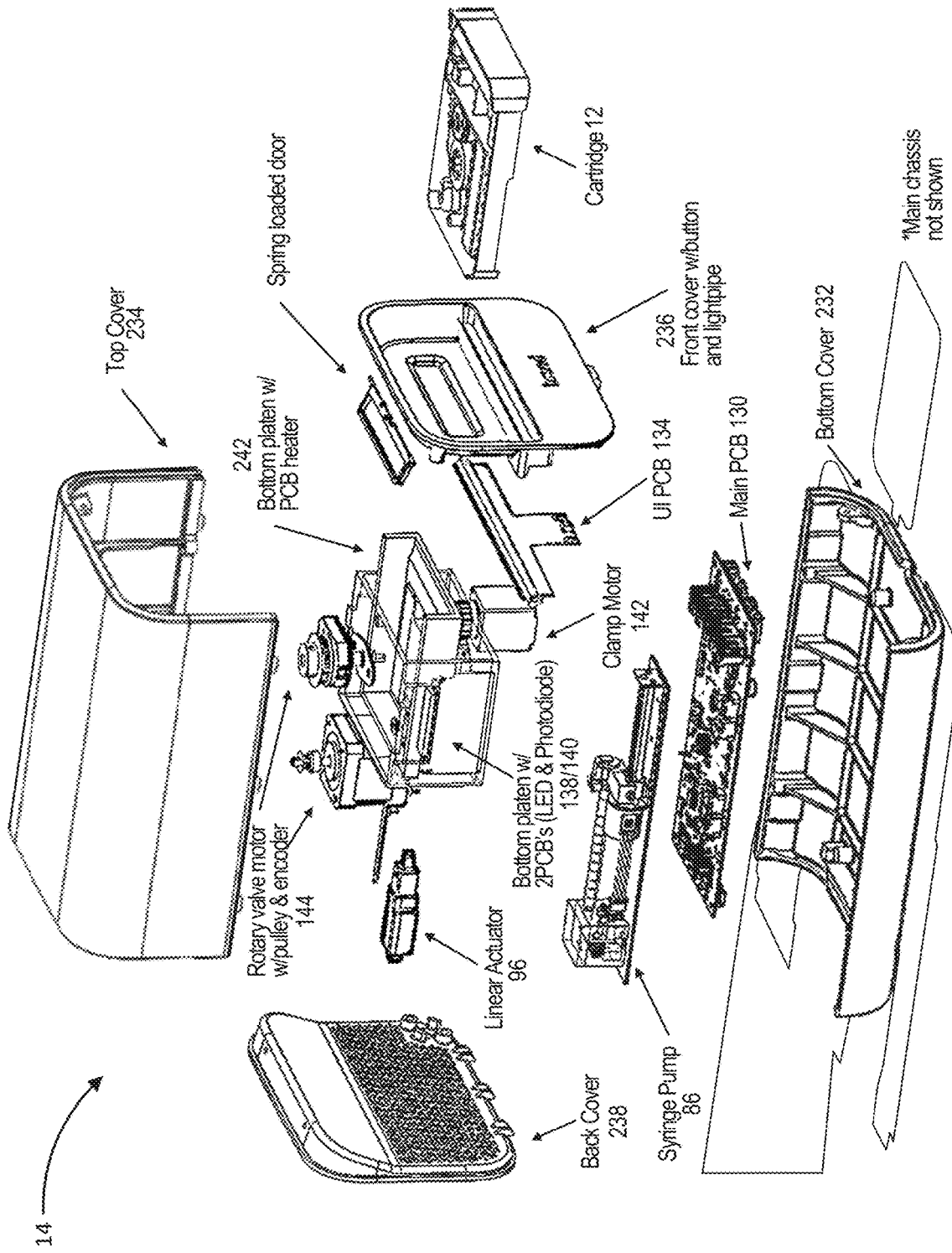
FIG. 27 is an exploded view illustrating the portable analyzer of FIG. 26.

FIG. 27 is an exploded view illustrating components/assemblies of the analyzer 14. The illustrated components/assemblies of the analyzer 14 include a bottom cover 232, a top cover 234, a front cover 236, a back cover 238, the main PCBA 130, the pump assembly 86, the user interface PCBA 134, the sliding valve linear actuator 96, a spring loaded door 240, the rotary valve motor 144, the clamp motor 142, a cartridge support 242, the detection optics PCBA 138, and the excitation optics PCBA 140.

Figure 28:
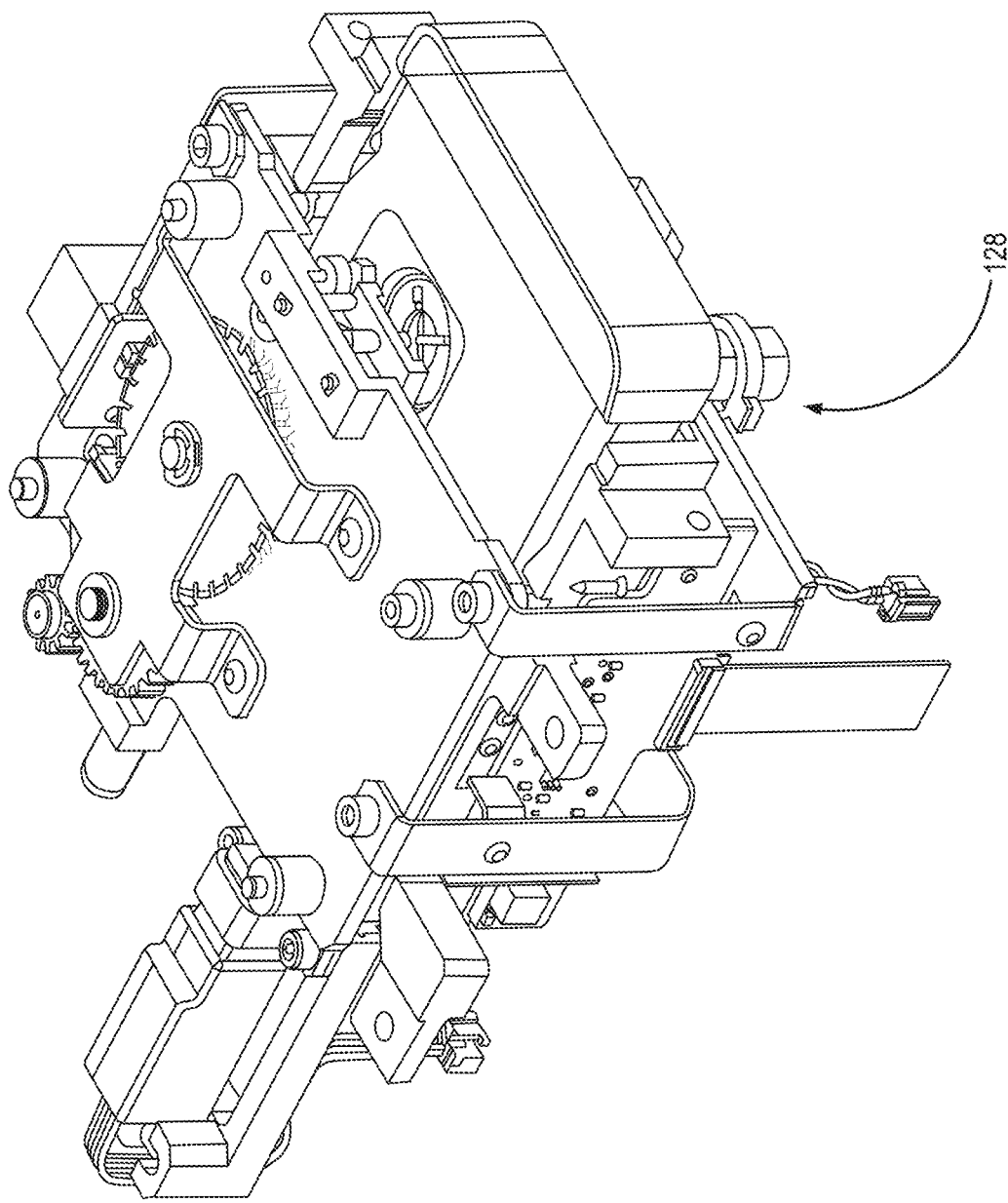
FIG. 28 illustrates a clamping system and a cartridge of the portable analyzer of FIG. 26.
Figure 29:
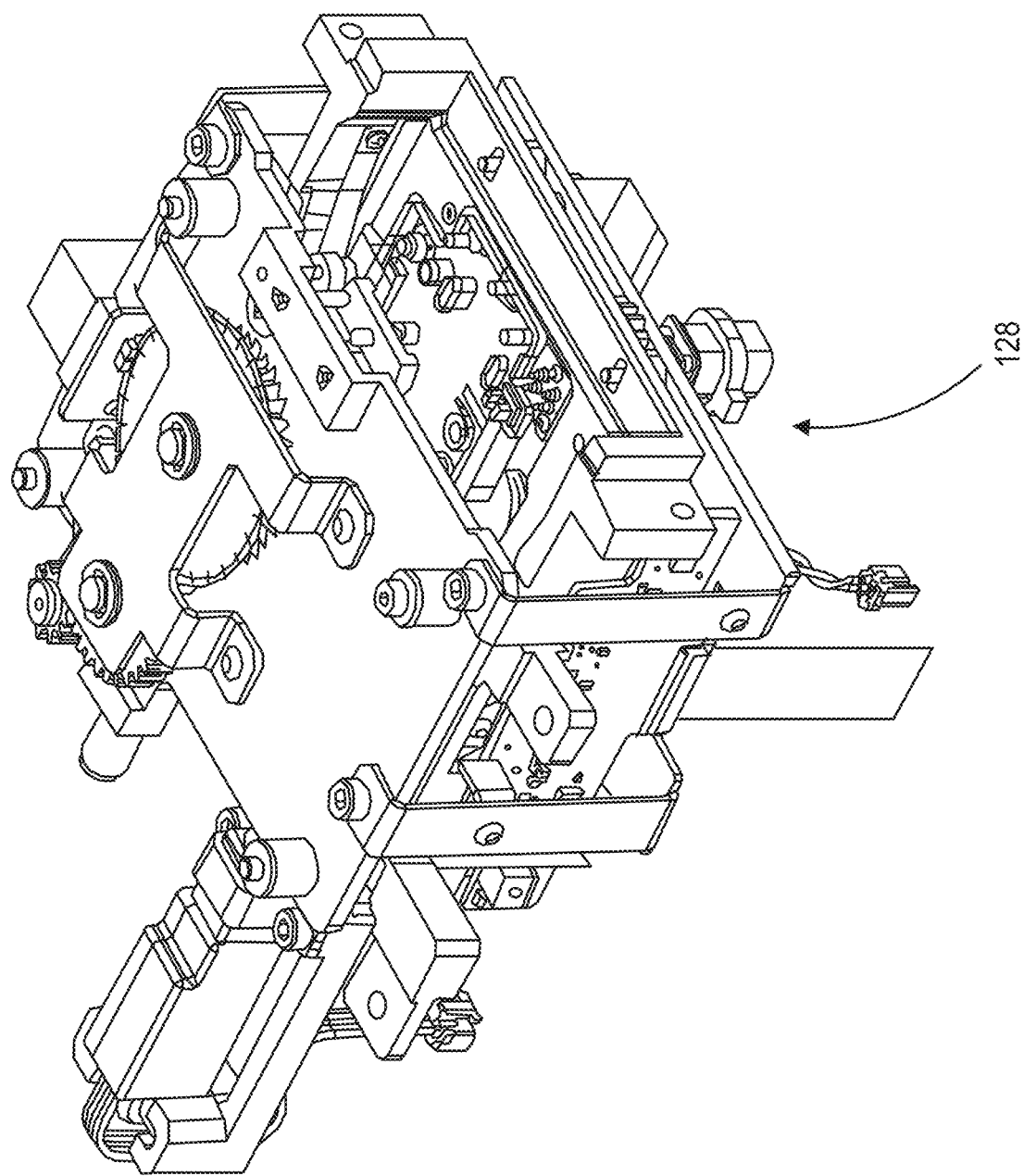
FIG. 29 illustrates the clamping system (without the cartridge) of FIG. 28.
Figure 30:
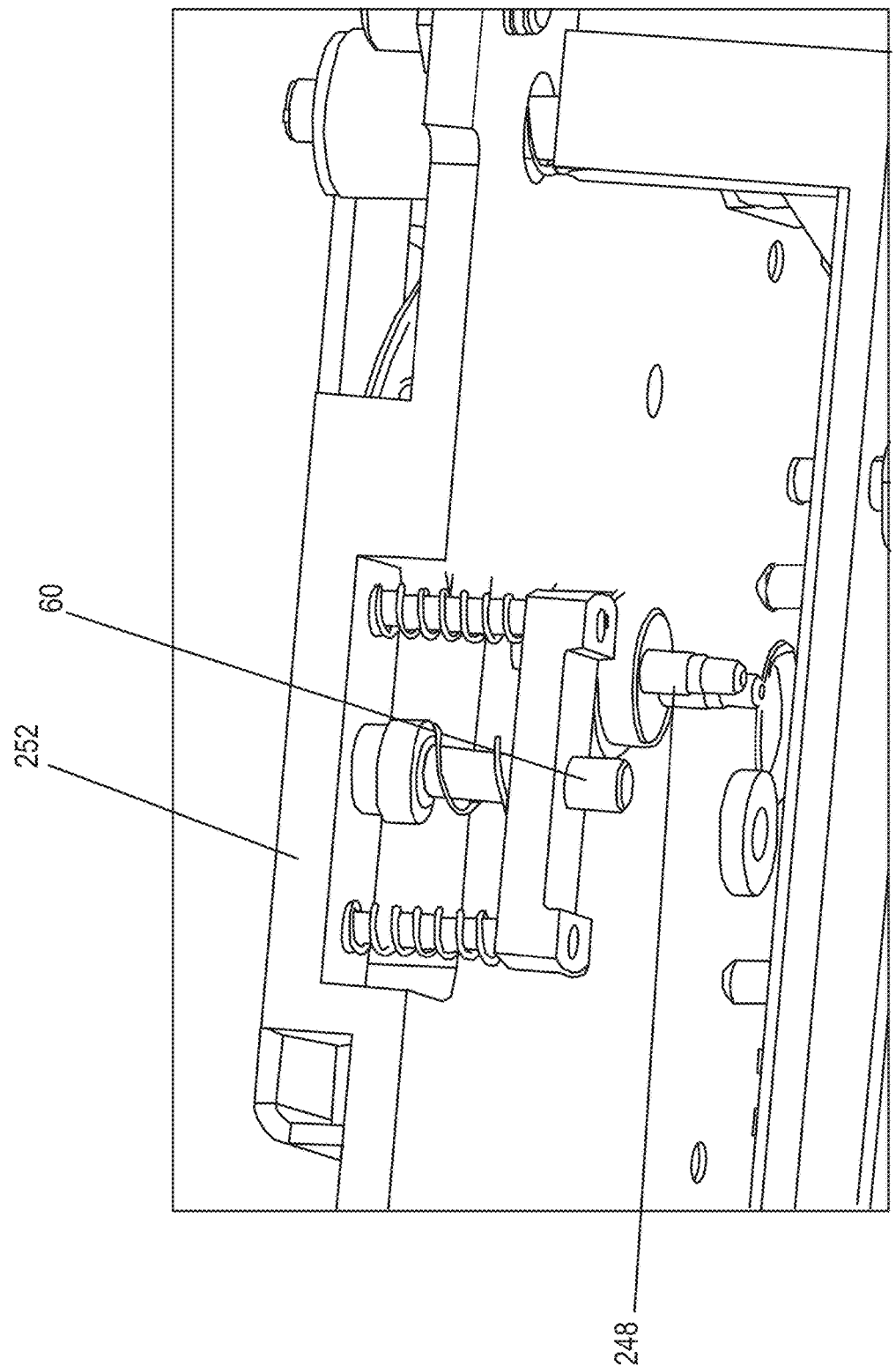
FIG. 30 illustrates cartridge interfacing assemblies of the portable analyzer of FIG. 26.
Figure 31:
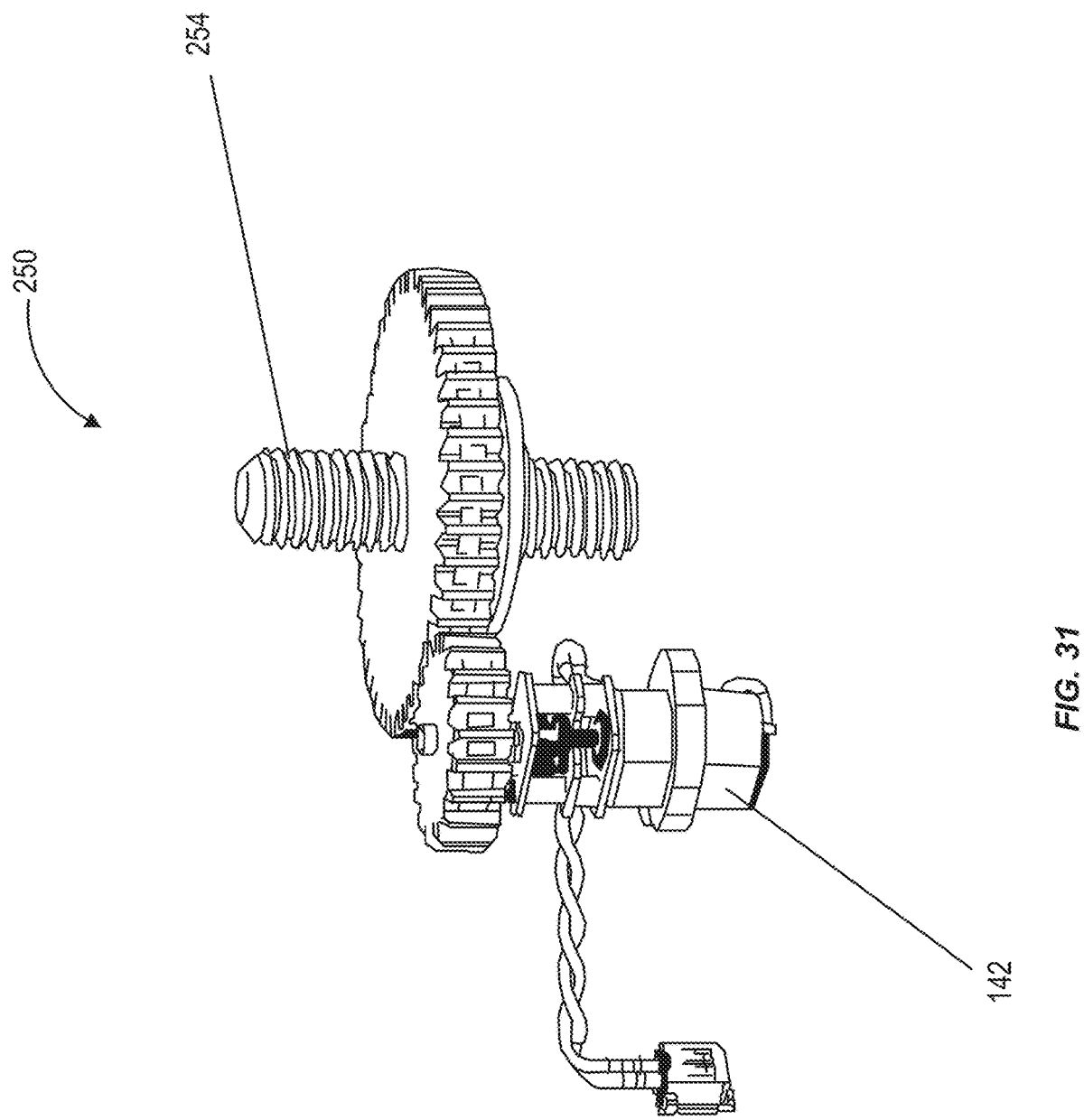
FIG. 31 illustrates a lead screw actuation assembly of the clamping system of FIG. 28.
Figure 32:
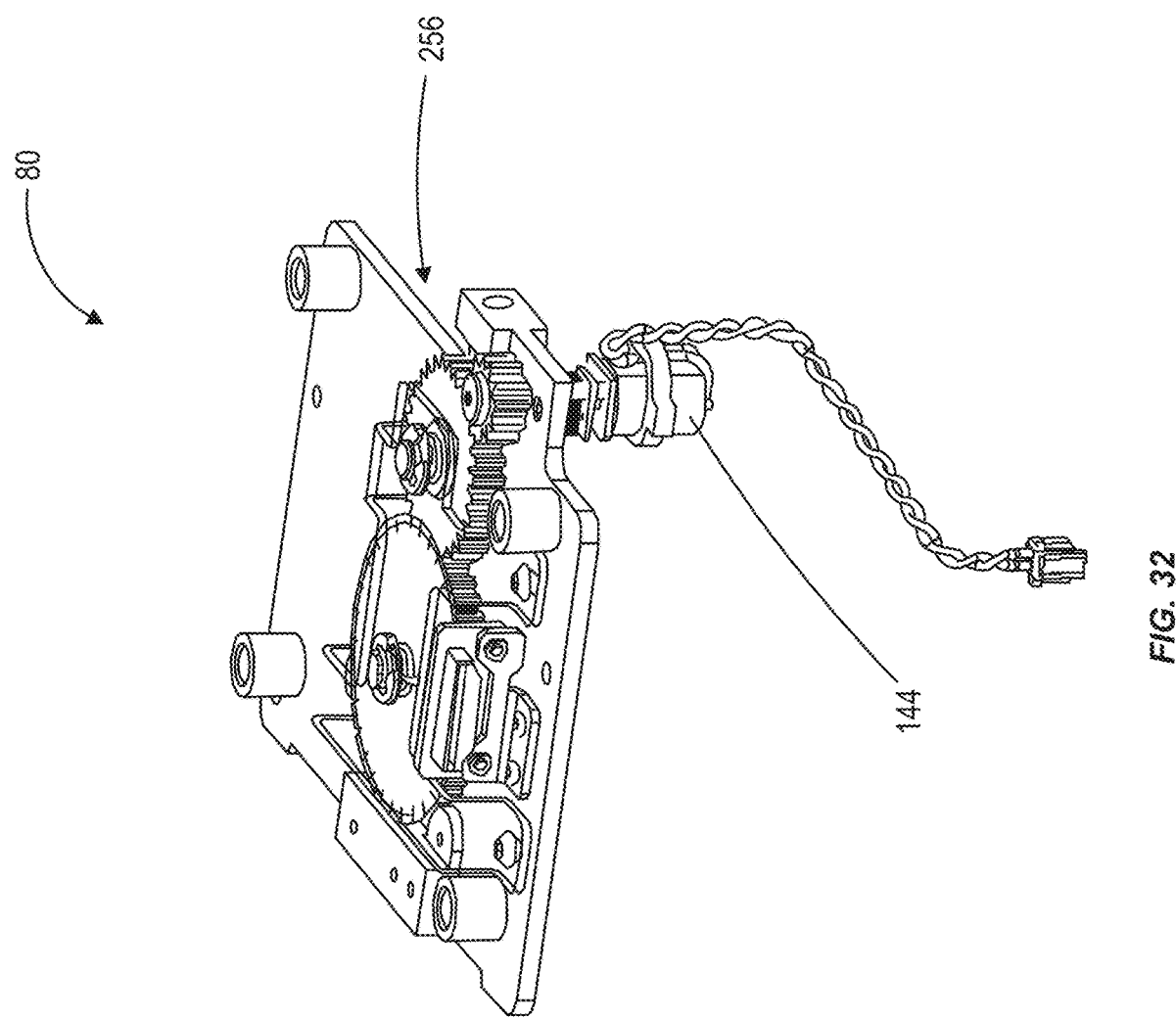
FIG. 32 is a top-side view of a rotary valve actuation assembly of the portable analyzer of FIG. 26.
Figure 33:
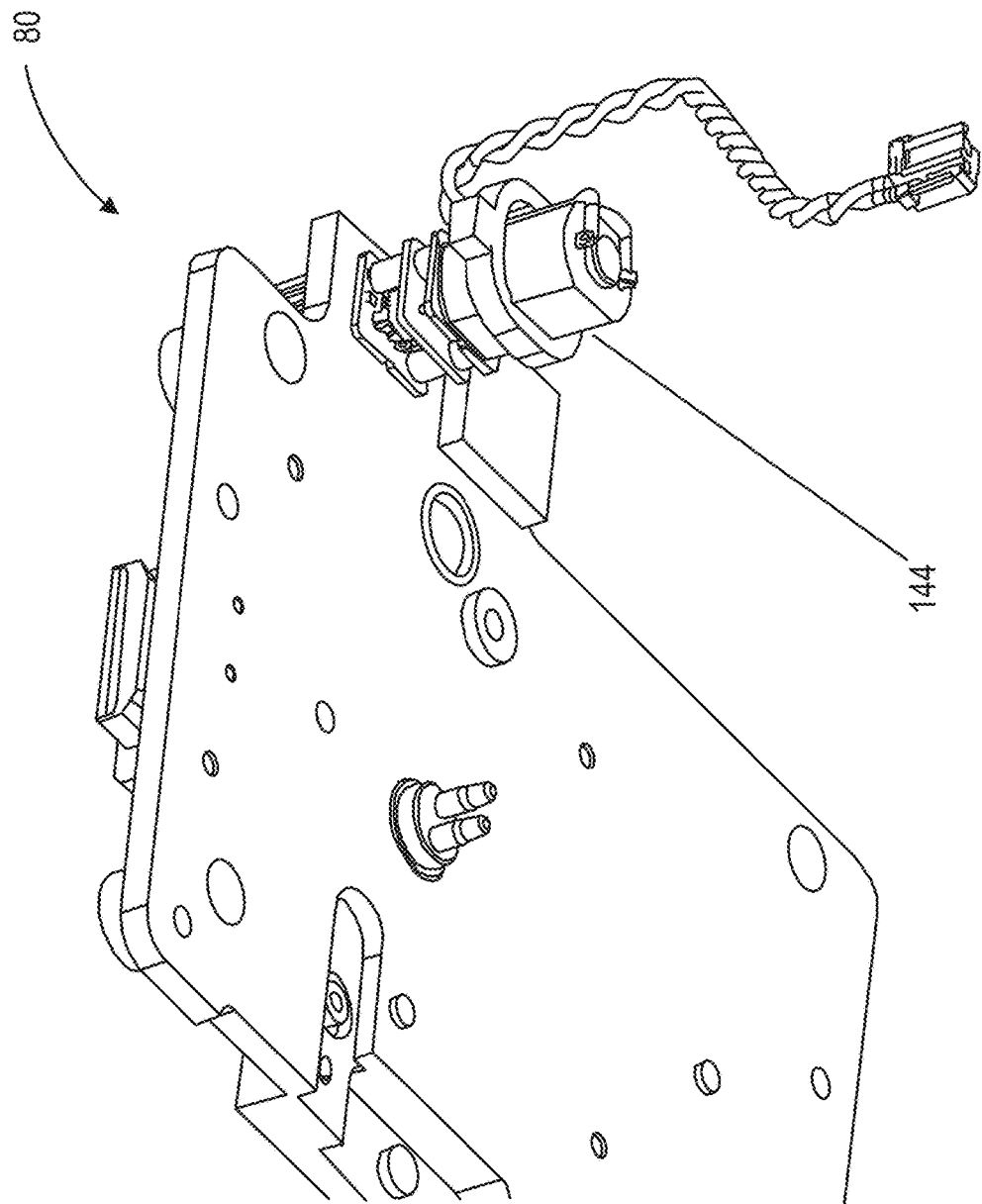
FIG. 33 is a bottom-side view of the rotary valve actuation assembly of FIG. 26.

FIG. 28, FIG. 29, FIG. 30, FIG. 31, FIG. 32, and FIG. 33 illustrate cartridge clamping and interfacing assemblies of the analyzer 14. FIG. 28 shows cartridge clamping and interfacing assemblies of the analyzer 14 and a cartridge 12 in a configuration in which the cartridge 12 has been fully inserted but not yet clamped by the analyzer 14. FIG. 29 shows cartridge clamping and interfacing assemblies of the analyzer 14 in the configuration of FIG. 28, but with the cartridge 12 not shown. FIG. 30 shows a close-up view of interfacing assemblies of the analyzer 14 including the clamp plunger 60, and a rotary valve interface coupler 248. FIG. 31 illustrates a lead screw actuation assembly 250 for translating the cartridge support 242 relative to an upper platen 252. The lead screw actuation assembly 250 includes the clamp motor 142 and a gear driven leadscrew 254 that is attached to the cartridge support 242. The cartridge support 242 is movably coupled with the upper platen 252 to controlled up and down translation of the cartridge support 242 relative to the upper platen 252 via translation of the gear driven leadscrew 254 via operation of the clamp motor 142. FIG. 32 is a top-side view of the rotary valve actuation assembly 80 of the portable analyzer 14. FIG. 33 is a bottom-side view of the rotary valve actuation assembly 80. The rotary valve actuation assembly 80 includes the rotary valve motor 144, which is drivingly coupled with the rotary valve interface coupler 248 via a gear train 256.

Figure 34:
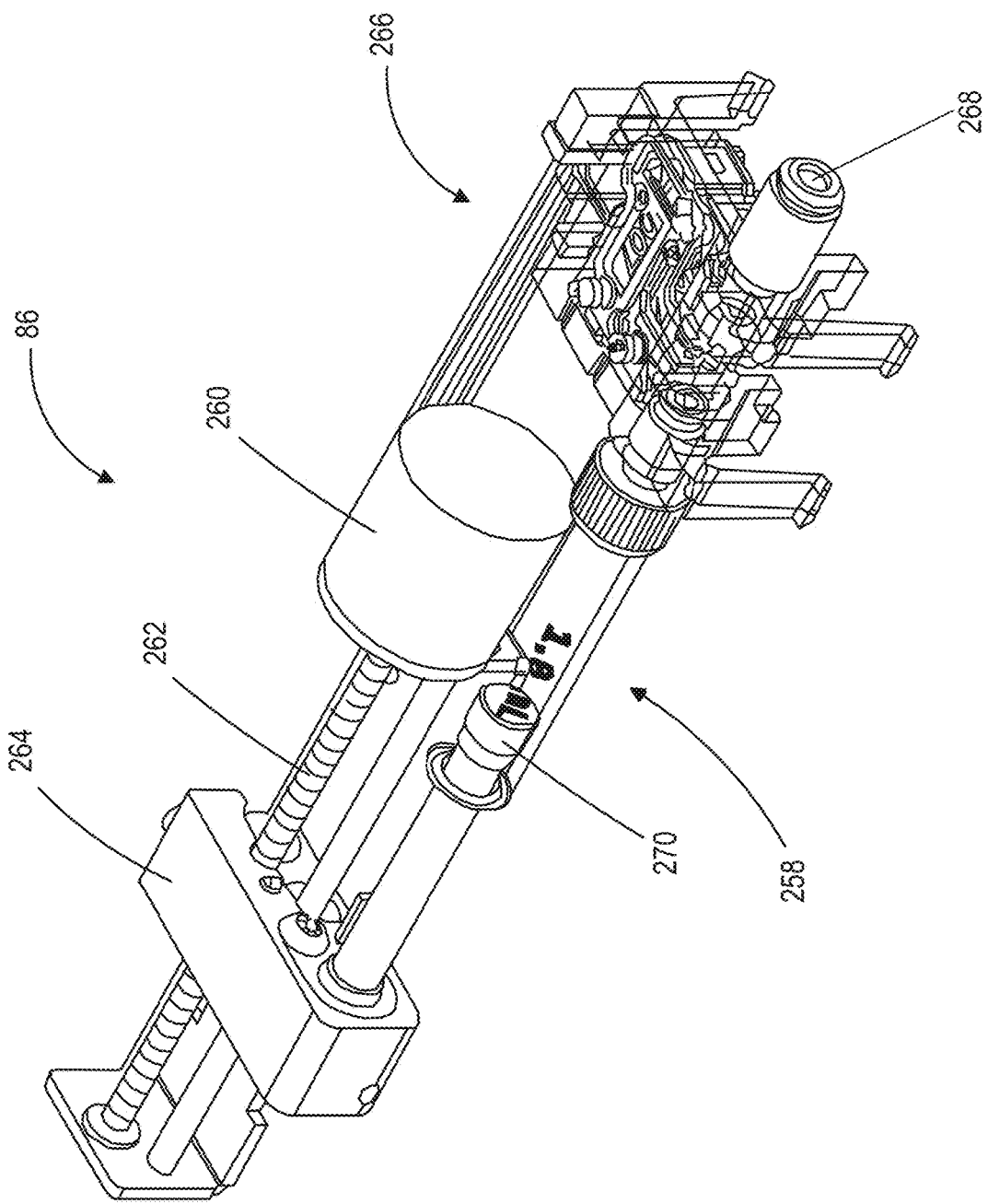
FIG. 34 illustrates a pump assembly of the portable analyzer of FIG. 26.

FIG. 34 illustrates the pump assembly 86 of the analyzer 14. The pump assembly 86 includes a syringe pump 258, the pump motor 260, a leadscrew 262, the drive member 264, a manifold assembly 266, and an output port 268. The output port 268 is placed in fluid communication with the actuation port 83 via an intervening assembly during clamping of the cartridge 12 by the analyzer 14. Rotation of the leadscrew 262 by the pump motor 260 produces translation of the drive member 264 along the leadscrew 262. The syringe pump 258 includes a plunger member 270 that is attached to the drive member 264 so as to actuate the plunger member 270 via the operation of the pump motor 260. The manifold assembly 266 includes the pump vent x-valve 148, which is controllably reconfigured to accommodate venting of the syringe pump 258 for reconfiguration of the syringe pump 258 without pulling air out of the cartridge 12 through the actuation port 83 or without injecting air into the cartridge 12 through the actuation port 83.

Figure 35:
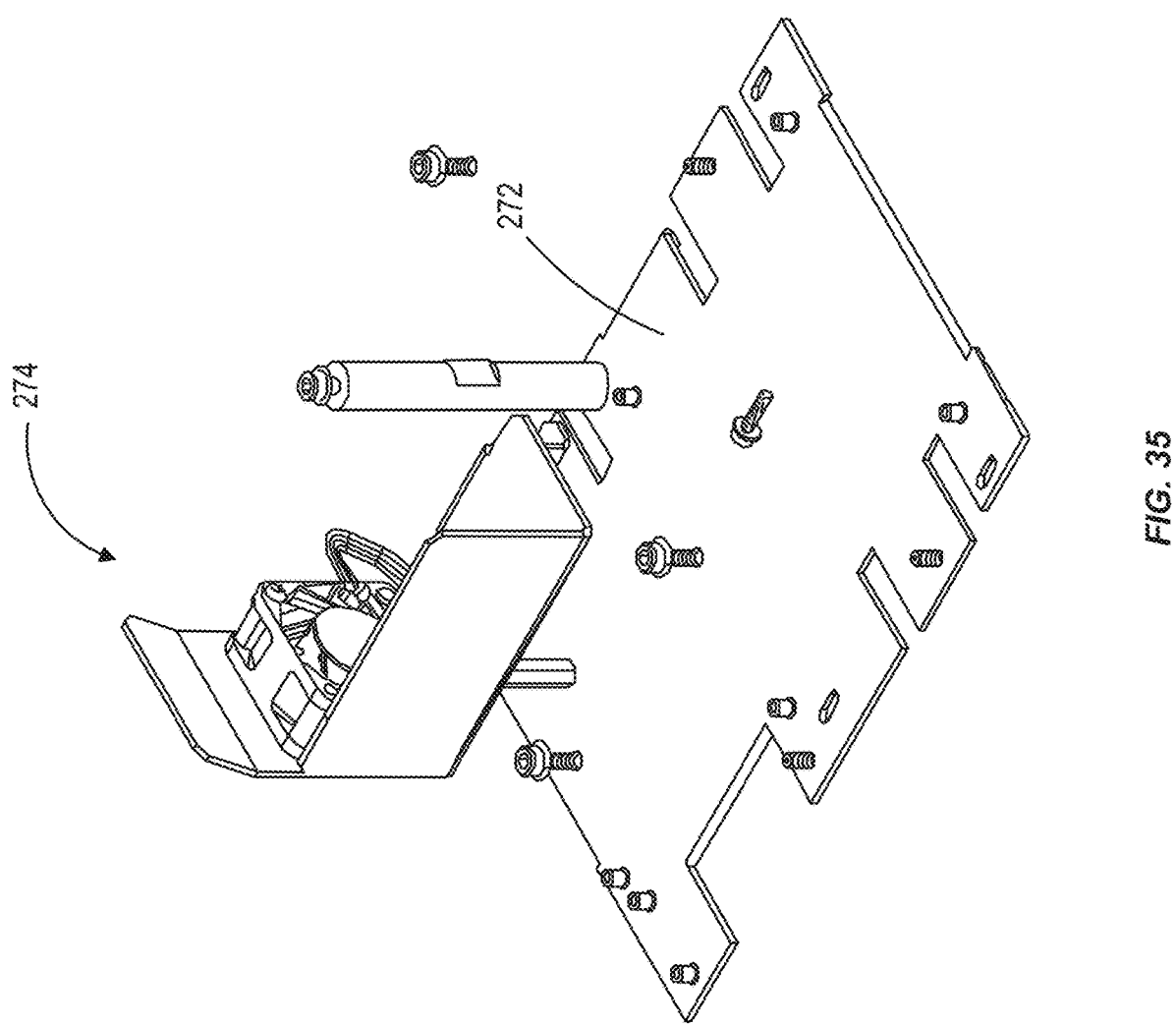
FIG. 35 illustrates a main chassis and a system cooling fan of the portable analyzer of FIG. 26.
Figure 36:
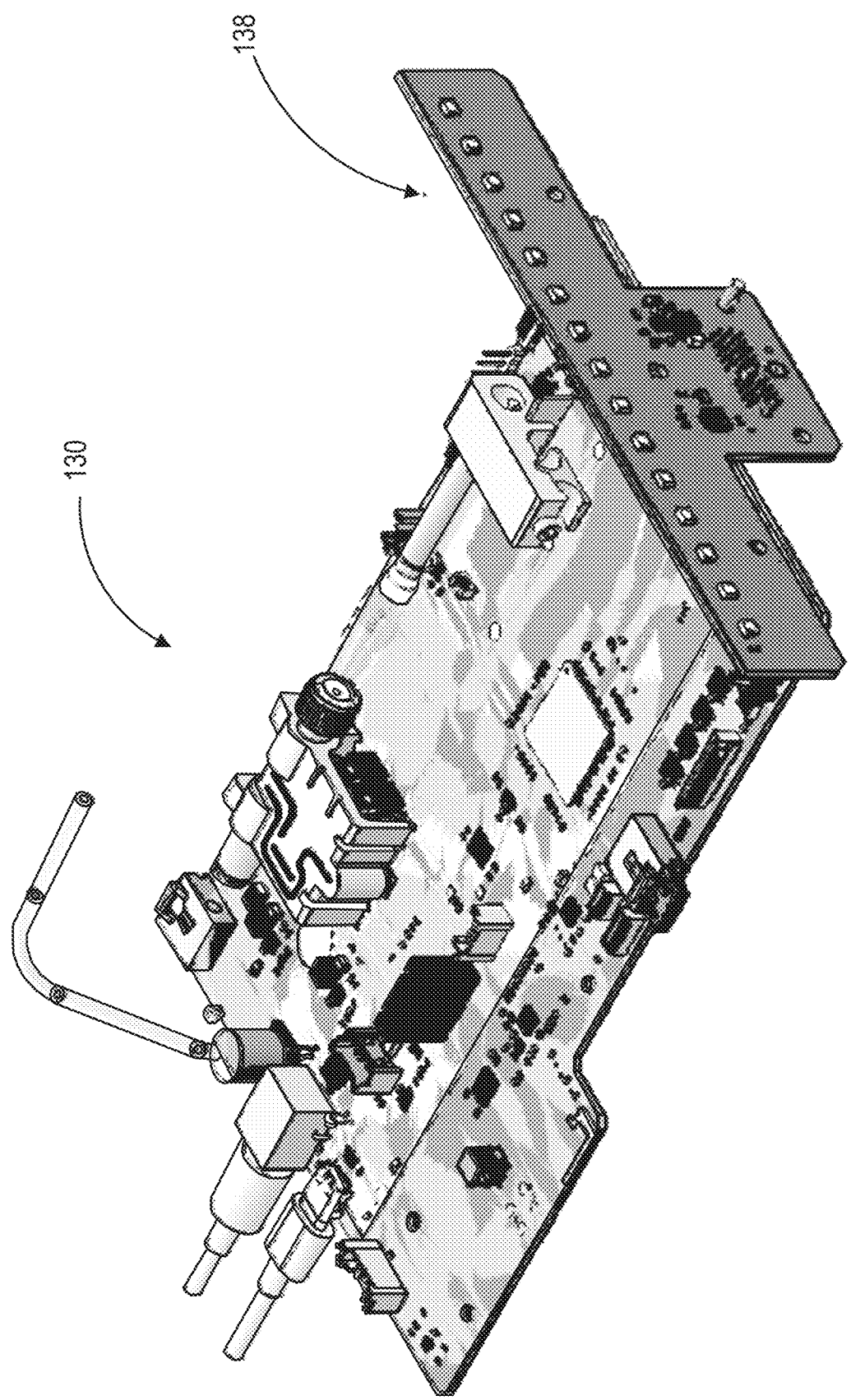
FIG. 36 illustrates a main printed circuit board assembly and a light bar of the portable analyzer of FIG. 26.

FIG. 35 illustrates a main chassis 272 and the system fan 274 of the analyzer 14. The main chassis 272 is attached to the bottom cover 232. The main PCBA 130 is attached to the main chassis 272. FIG. 36 illustrates the main PCBA 130 and the detection PCBA 138 of the analyzer 14.

Figure 37:
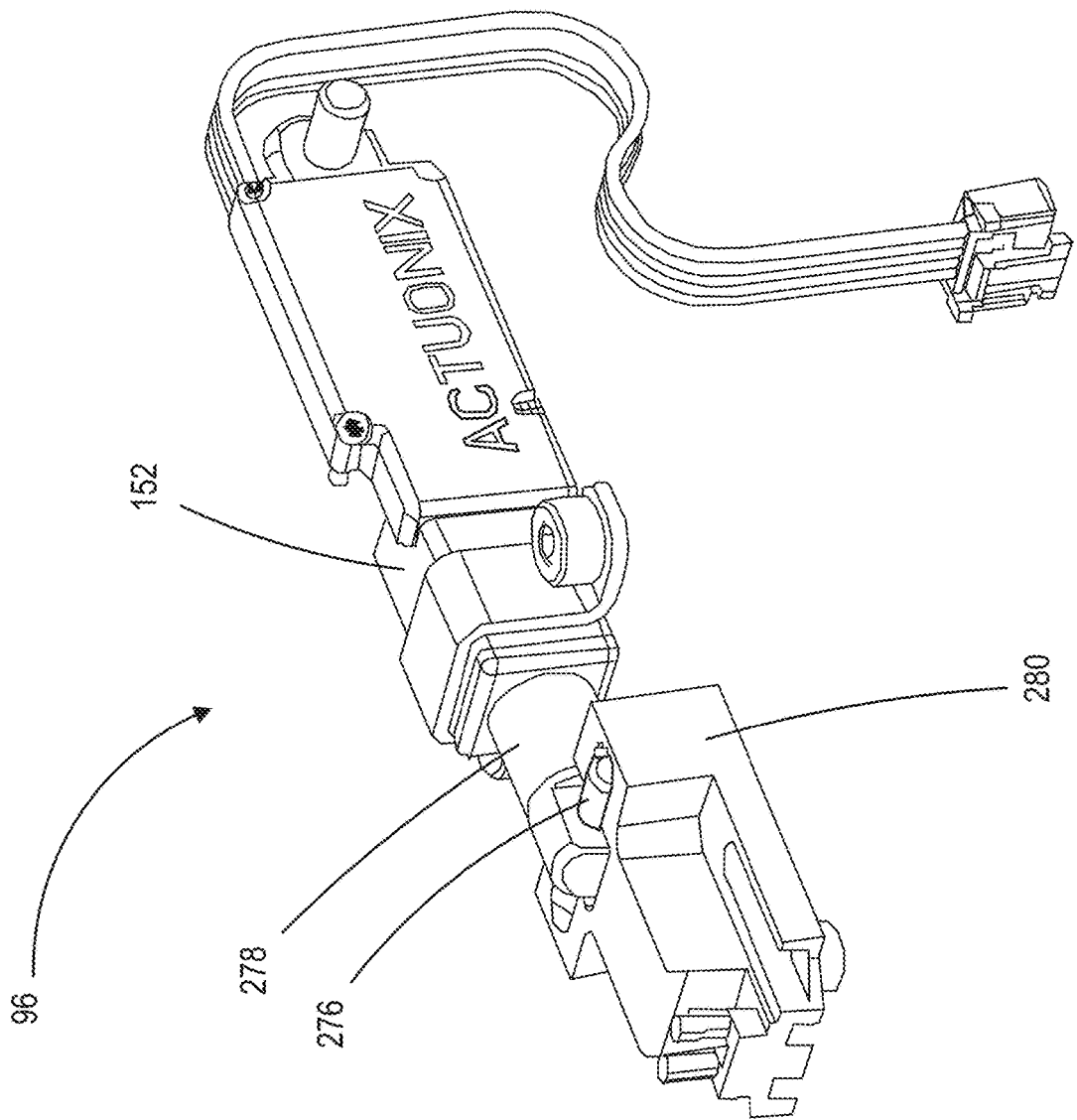
FIG. 37 illustrates a sliding valve actuator of the portable analyzer of FIG. 26.

FIG. 37 illustrates the sliding valve actuator assembly 96. The sliding valve actuation assembly 96 includes the sliding valve motor 152 and a coupling pin 276 attached and oriented perpendicular to an output shaft 278 of the sliding valve actuation assembly 96. The coupling pin 276 comes into engagement with a coupling fitting 280 of the slider valve 94 during the operatively coupling of the cartridge 12 to the analyzer 14 via the clamping of the cartridge 12 following insertion of the cartridge 12.

Figure 38:
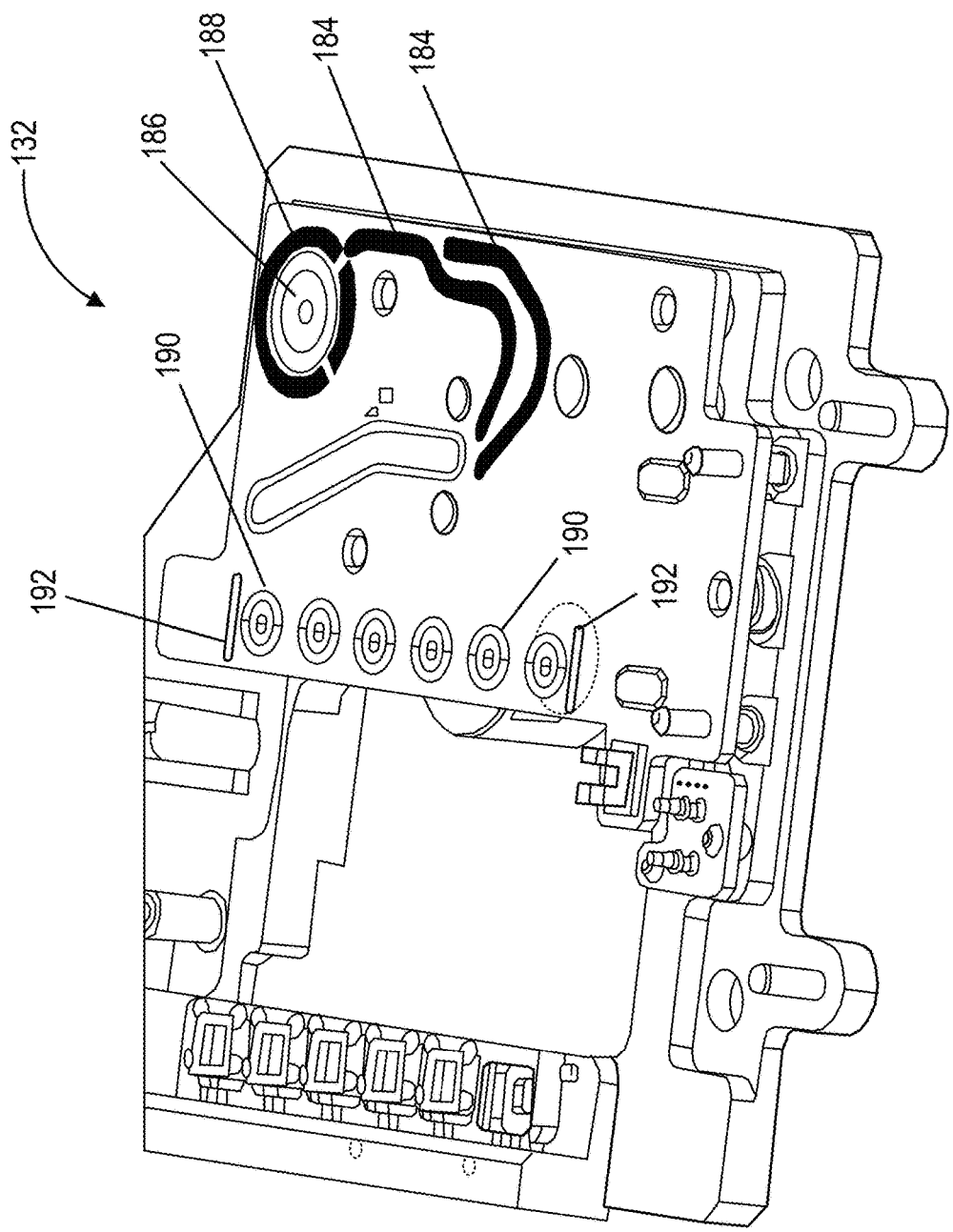
FIG. 38 illustrates heating elements of the portable analyzer of FIG. 26.

FIG. 38 shows the heaters PCBA 132 and the detection heating elements 100. The heaters PCBA 132 includes the lysis channel heating element 184, the lysis circular heating element 186, and the lysis annular heating element 188. The lysis channel heating element 184 is employed to heat the lysis sample solution prior to entering the lysis chamber 68. The lysis annular heating element 188 surrounds the lysis circular heating element 186. The lysis annular heating element 188 encircles the outside of the lysis chamber 68. The lysis circular heating element 186 is located in the center and directly below the lysis chamber 68. The combination of these three lysis solution heating elements is employed to obtain a fast ramp up time and minimal thermal gradient. Heating the lysis sample solution prior to entering the lysis chamber may help reduce the possibility of non-inactivated proteinase-k buffer contamination of lysed sample aliquots.

The amplification well ring heating elements 190 and the amplification well bar heating elements 192 cover two zones. Each of the amplification well ring heating elements 190 encircles one of the amplification wells 70. Each of the amplification well bar heating elements 192 is located adjacent to the a respective edge of a respective one of the first and sixth amplification wells 70. The combination of the amplification well ring heating elements 190 and the amplification well bar heating elements 192 is employed to obtain a fast ramp up time (about 2 minutes) and minimal thermal gradient around the 60 degree C. target set point.

The detection heating element 214 and the excitation heating element 220 contact the housing surrounding the cartridge detection wells 74. The combination of the detection heating element 214 and the excitation heating element 220 are employed to provide a stable detection well temperature around the 37 degree C. target set point.

The analyzer 14 employs printed circuit board (PCB) traces along with surface mount (SMT) resistors as the heating elements. The PCB traces are configured to provide a suitable resistance at the supplied voltage to obtain the required heater wattage. Each heating element is separately controlled via a proportional-integral-derivative (PID) controller via pulse wave modulation (PWM) switching the PCB heater trace to ground connection and using the heater zone's NTC thermistor as control loop feedback.

Figure 39:
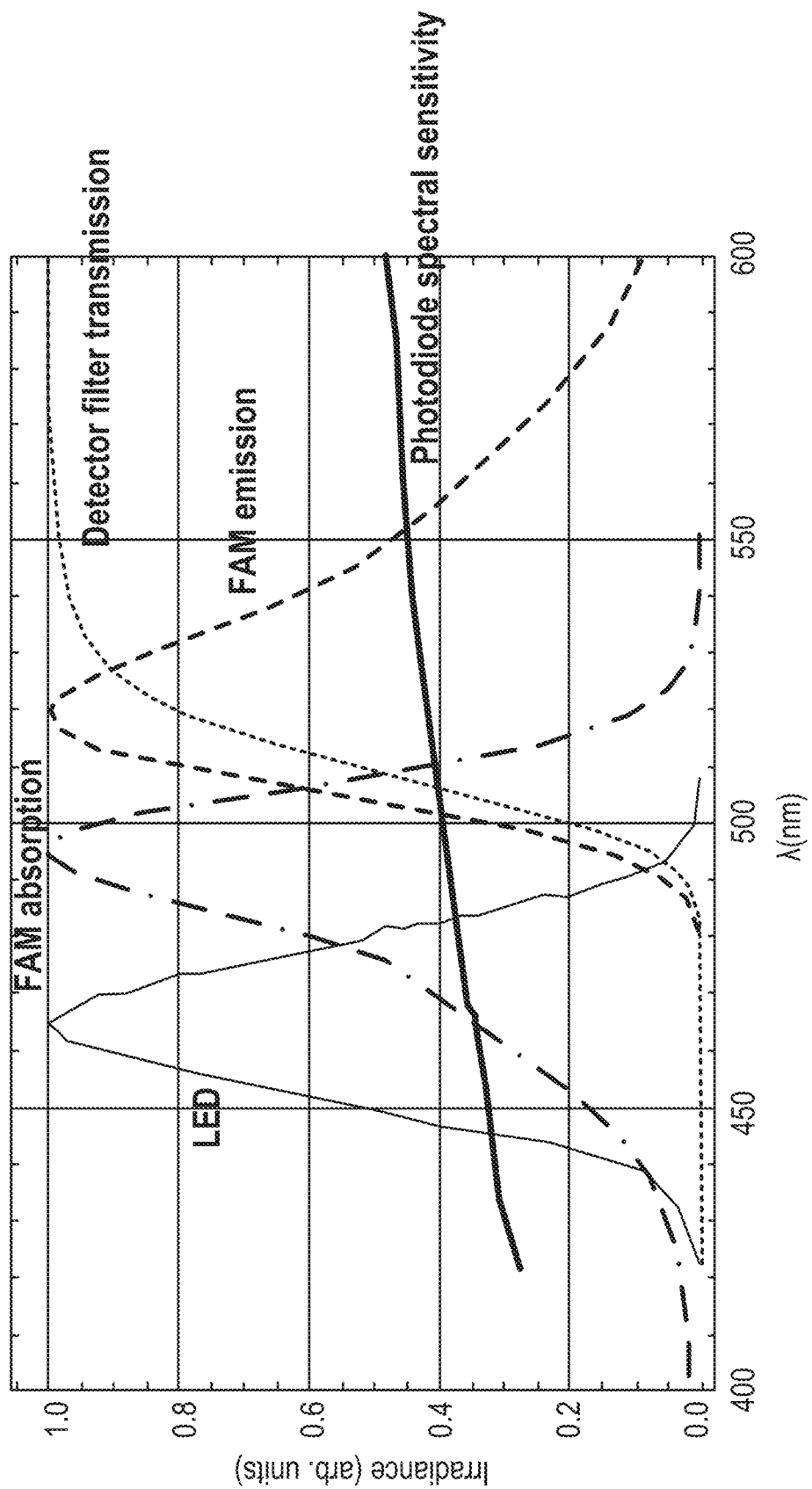
FIG. 39 illustrates an absorption and emission spectrum for the fluorescent dye FAM (Carboxyfluorescein) applicable to some embodiments of the diagnostic testing system of FIG. 1.

CRISPR reactions are detecting by measuring FAM emission light intensity. Upon excitation of the CRISPR product within the FAM absorption wavelength bandwidth (max 495 nm), FAM emits light across a shifted wavelength bandwidth (max 520 nm). FIG. 39 illustrates a FAM (Carboxyfluorescein) absorption and emission spectrum that are applicable to some embodiments of the diagnostic testing system 10 and include the FAM absorption wavelength spectrum and the FAM emissions wavelength spectrum.

Figure 40:
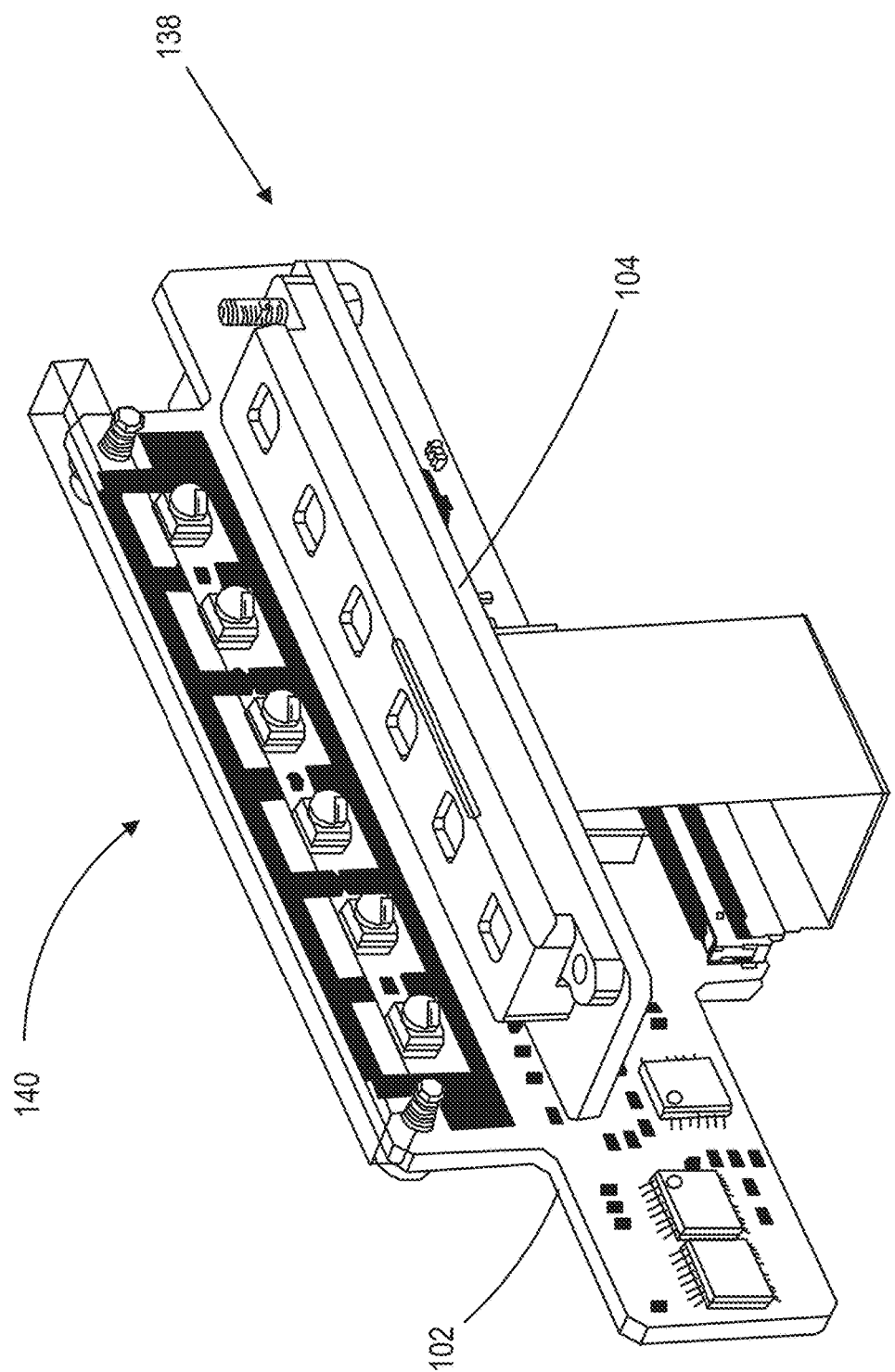
FIG. 40 and FIG. 41 illustrate excitation light and fluorescence detection assemblies of the portable analyzer of FIG. 26.
Figure 41:
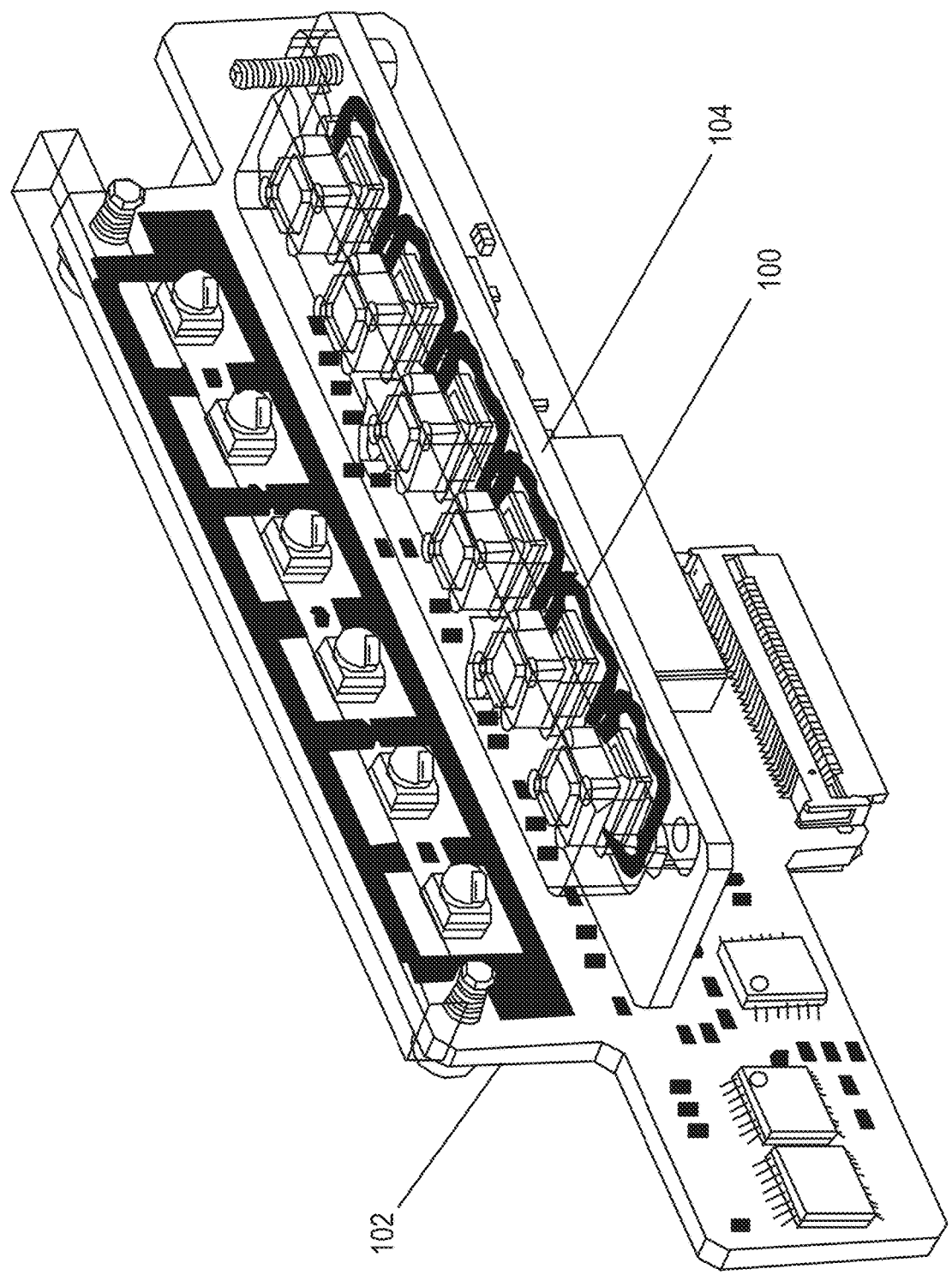
Figure 42:
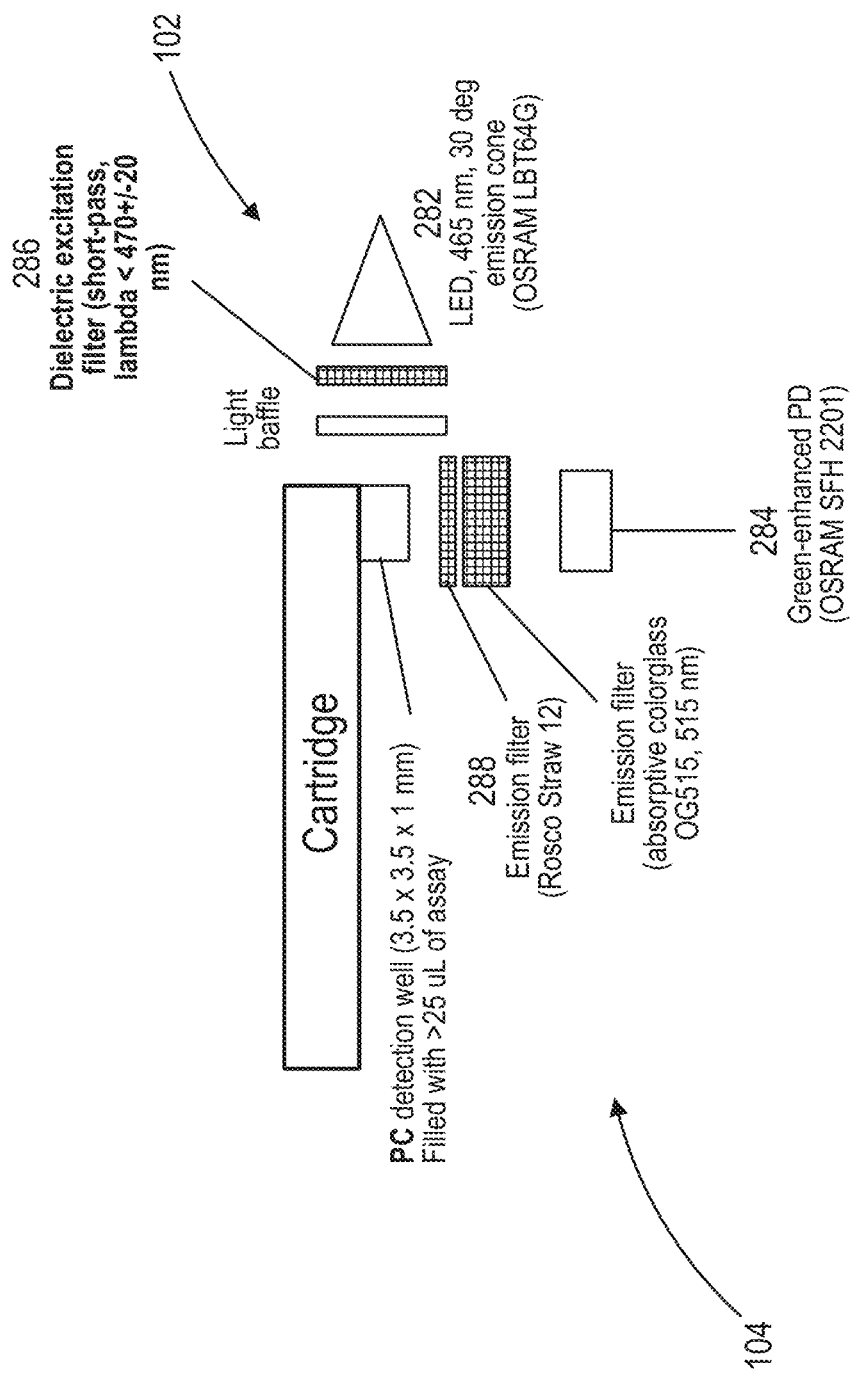
FIG. 42 illustrates fluorescence excitation and detection components of the portable analyzer of FIG. 26.

FIG. 40 and FIG. 41 show the excitation optics PCBA 140 and the detection optics PCBA 138. The excitation optics PCBA 140 includes six LEDs 282 for irradiating the detection solution in the detection wells with excitation light. The detection optics PCBA 138 includes six photodiodes 284 for sensing resulting fluorescence from the irradiated detection solutions. As shown in FIG. 42, an excitation optical filter 286 is used to band-pass filter the excitation bandwidth and an emissions optical filter 288 is used to band-pass filter the emission detection bandwidth. The optical filters 286, 288 are employed to inhibit detection of the LED excitation light by the photodiodes 284 to inhibit excitation light induced degradation of the signal to noise ratio of the detection signals generated by the photodiodes 284.

There are six optical detection channels in the analyzer 14. The detection photodiode analog front end (AFE) outputs along with related AFE reference voltage and AFE supply voltage are multiplexed to a single 12-bit, 200 ksps, SAR ADC. The photodiode AFE gain is firmware adjustable via an analog switching of different resistor networks into its trans-impedance amplifier (TIA) feedback. AFE gain settings allow ranging from photodiode peak current of 10 nA to 10 uA. The excitation LED drive current is PWM adjustable with the PWM signal low-pass filtered to set the reference voltage on the current-feedback op-amp stage driving the LED bipolar junction transistor (BJT). The combination of LED driver current adjustability and photodiode adjustable TIA gain allows detected signal levels to be scaled to within the ADC voltage range. A low on-state resistance, fast settle time analog switch is used to switch inputs to the ADC.

Figure 43:
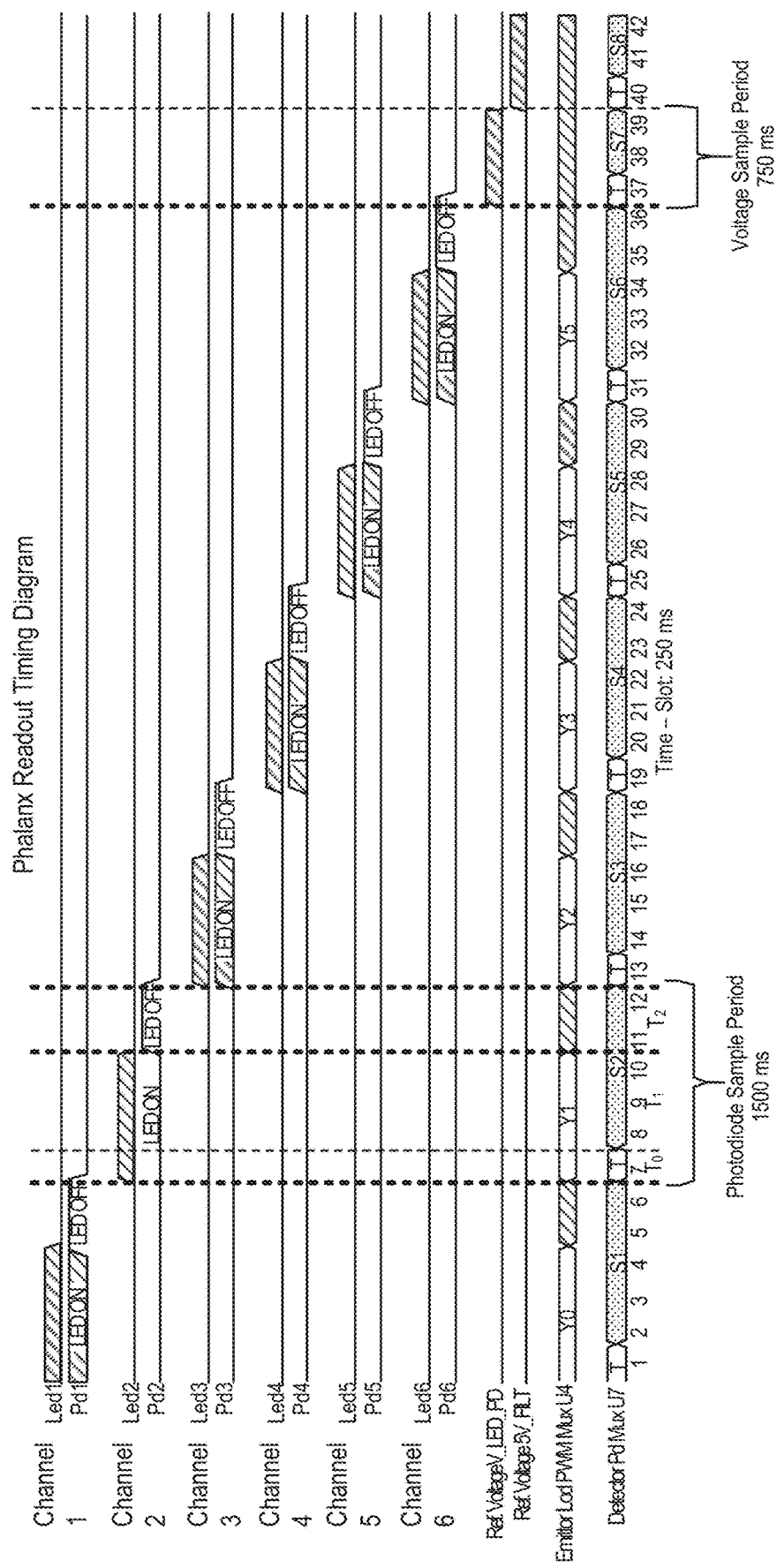
FIG. 43 illustrates detection channel sample timing that can be used by the portable analyzer of FIG. 26.

Referring now to FIG. 43, during sampling of a photodiode channel, the associated excitation LED is turned on for a period of time to capture FAM emission from the CRISPR reaction (time $T_1$), and then the LED is turned off for a period of time (time $T_2$) to capture background light levels. Background levels are subtracted from FAM emission readings. Background level sampling is also be used to detect ambient light excursions and LED intensity drift. If ambient light reduces signal-to-background levels below acceptable CRISPR kinetic detection levels, a LED/PD modulation scheme at 240 Hz (2*120 Hz for fluorescent light tube switch frequency) can be used to effectively filter out background light by de-convolving in software. At the beginning of each photodiode channel sampling period, there is a switch settling period of 250 ms (time $T_0$) for the ADC low-pass input filter. Each photodiode channel is sampled for 1500 ms. At the end of sampling all six photodiode channels, the AFE reference and supply voltages are sampled for 750 ms each. These voltages are sampled to detect voltage excursions that may impact and correlate to erroneous photodiode readings. A total of 10.5 seconds may be sufficient to sample all six photodiode channels and the AFE voltages.

Figure 44:
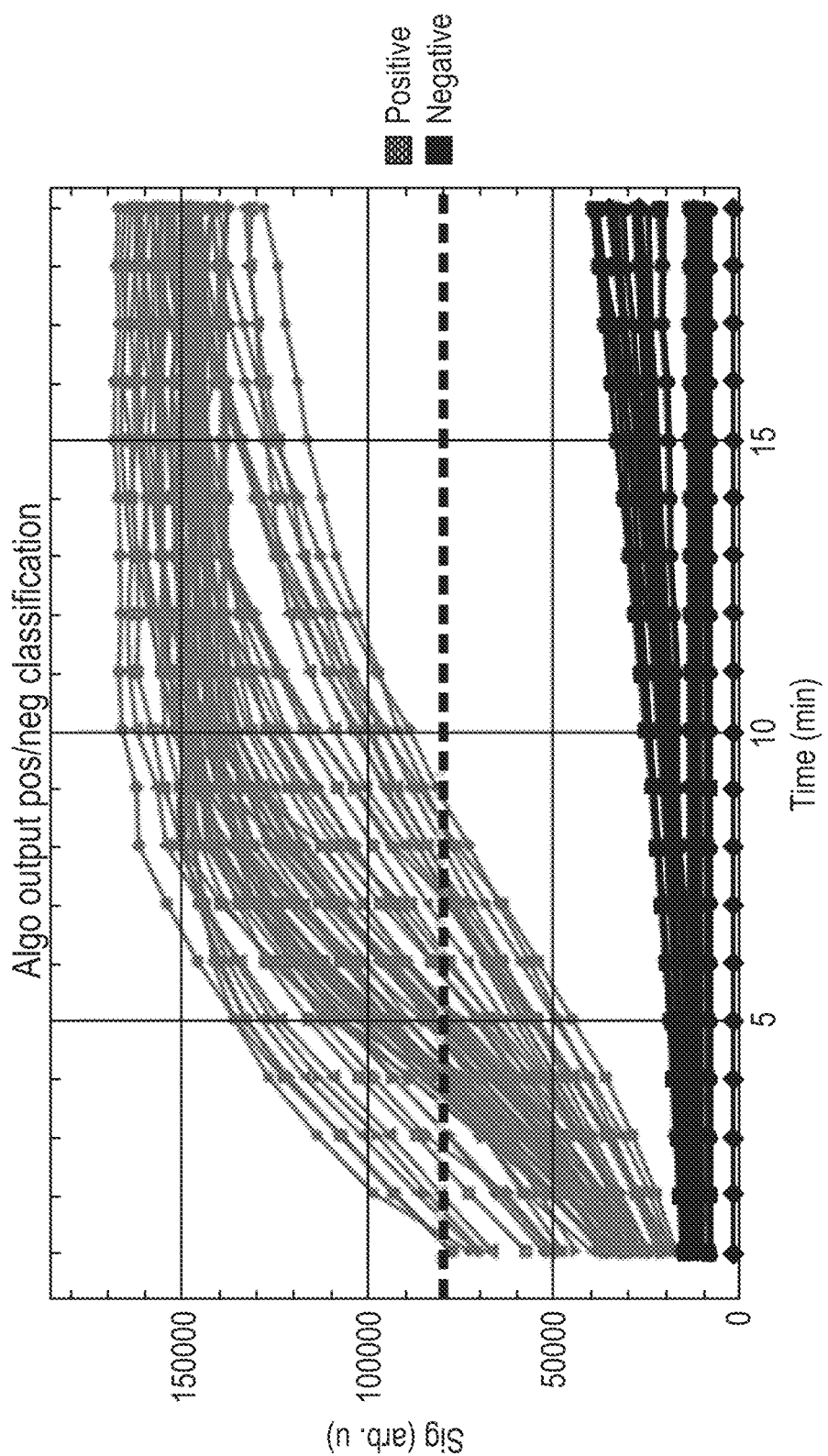
FIG. 44 illustrates example fluorescence curves measured by the portable analyzer of FIG. 26 for both positive and negative test results.

Cycling of sample timing can be repeated for up to 15 minutes in order to collect CRISPR reaction kinetic raw data. CRISPR kinetic data is used by the smartphone application to determine a positive, negative or invalid result. As shown in FIG. 44, positive fluorescence readings resemble a sigmoid curve with a sharp positive slope. In contrast, negative fluorescence readings have a shallow to flat positive slope.

Figure 45:
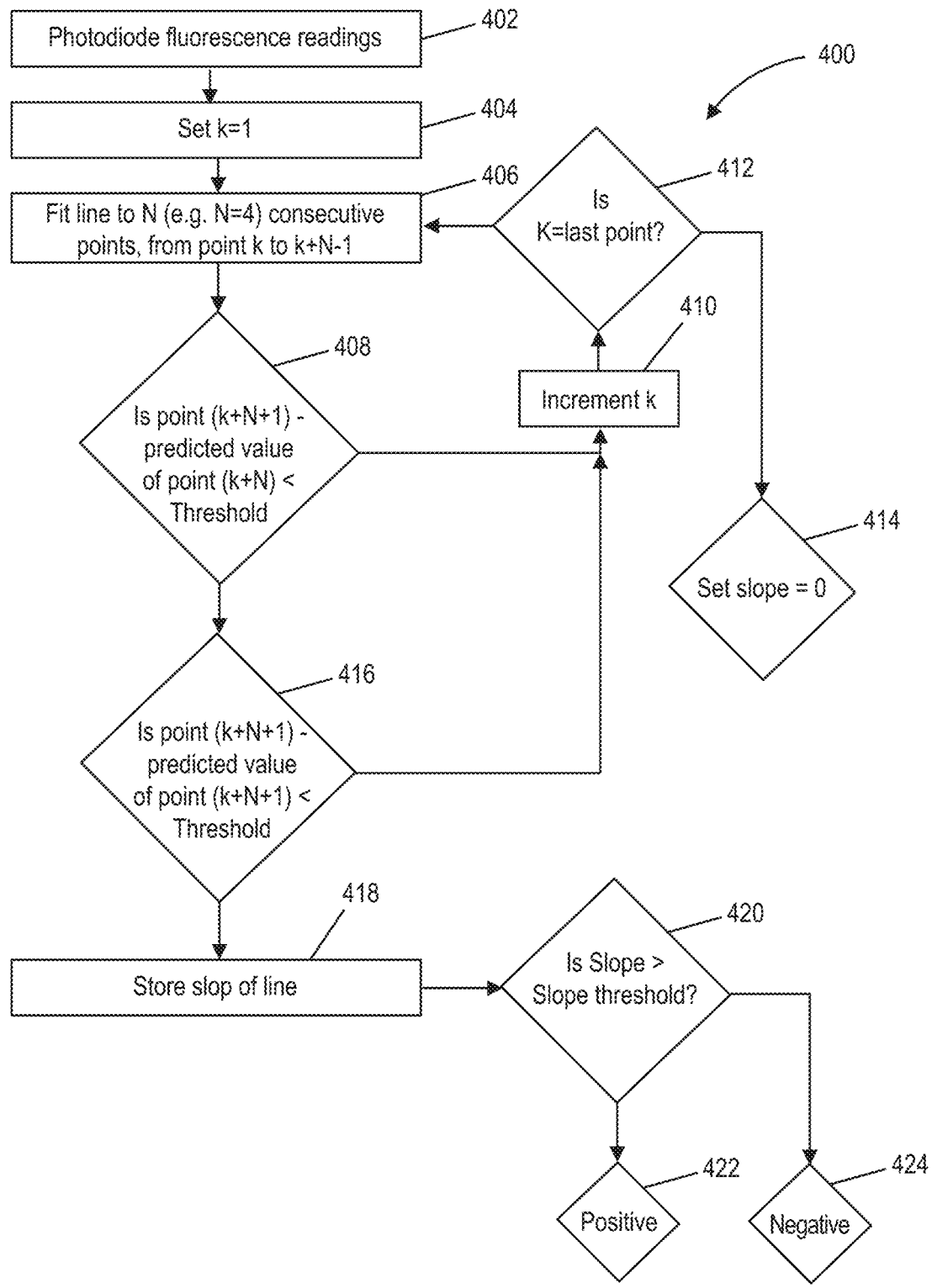
FIG. 45 illustrates an approach for processing detected fluorescence to determine a positive or negative test result in the diagnostic testing system of FIG. 1.

FIG. 45 illustrates an approach 400 for processing the CRISPR kinetic data to determine a positive or negative test result. The detection algorithm 400 uses the slope deltas within the first 5 minutes of the CRISPR reaction along with threshold fluorescence values to render a positive or negative results to the user. Invalid results can occur in the event that the cartridge positive control does not "come up" positive or the human beta-actin gene is not detected. In act 402, the photodiode fluorescence readings are taken at a suitable time interval over a suitable total time span. For example, as shown in FIG. 44, the photodiode fluorescence readings can be taken every minute over an eighteen minute total time span. In many embodiments, the photodiode fluorescence readings are corrected for electronic offsets via dark reading subtraction. In act 404, a counter (K) is set to 1. In act 406, line segments are fit between consecutive photodiode fluorescence readings to span a suitable number of the time intervals. For example, four line segments can be fit between consecutive photodiode fluorescence readings to cover 4 of the time intervals, which would cover 4 minutes for a 1 minute interval between readings. In act 408, the change in the photodiode fluorescence reading over the last of the fit line segments is compared to a suitable threshold. If the change in the photodiode fluorescence reading over the last of the fit line segments is less than the threshold, the counter is incremented in act 410. In act 412, the counter (K) is evaluated to check if the counter (K) corresponds to the last of the consecutive photodiode fluorescence readings. If the counter (K) corresponds to the last of the consecutive photodiode fluorescence readings, the slope for the consecutive photodiode fluorescence readings is set to zero in act 414. If the counter (K) has not reached the number that corresponds to the last of the consecutive photodiode fluorescence readings, act 406 and act 408 are repeated. If the change in the photodiode fluorescence reading over the last of the fit line segments is greater than the threshold in act 408, the detection algorithm 400 proceeds to act 416. In act 416, the magnitude of the last photodiode fluorescence reading of the fit line segments is compared to a predicted value for the last photodiode fluorescence reading of the fit line segments obtained by extrapolating the second to last of the fit line segments. If the magnitude of the last photodiode fluorescence reading of the fit line segments is greater than the predicted value by a suitable threshold, this indicates that the slope of the last of the fit line segments is greater than the slope of the second to last of the fit line segments by the threshold. If the slope of the last of the fit line segments is greater than the slope of the second to last of the fit line segments by the threshold, the detection algorithm 400 returns to act 410 to attempt identify a line segment with the highest positive slope. If the slope of the last of the fit line segments is not greater than the slope of the second to last of the fit line segments by the threshold, the detection algorithm 400 proceeds to act 418 in which the slope of the last of the fit line segments is stored. In act 420, if the slope stored in act 418 is greater than a suitable slope threshold, a positive test result is determined in act 422. If the slope stored in act 418 is not greater than the slope threshold, a negative test result in determined in act 424.

Cartridge Identification/Authorization

Figure 46:
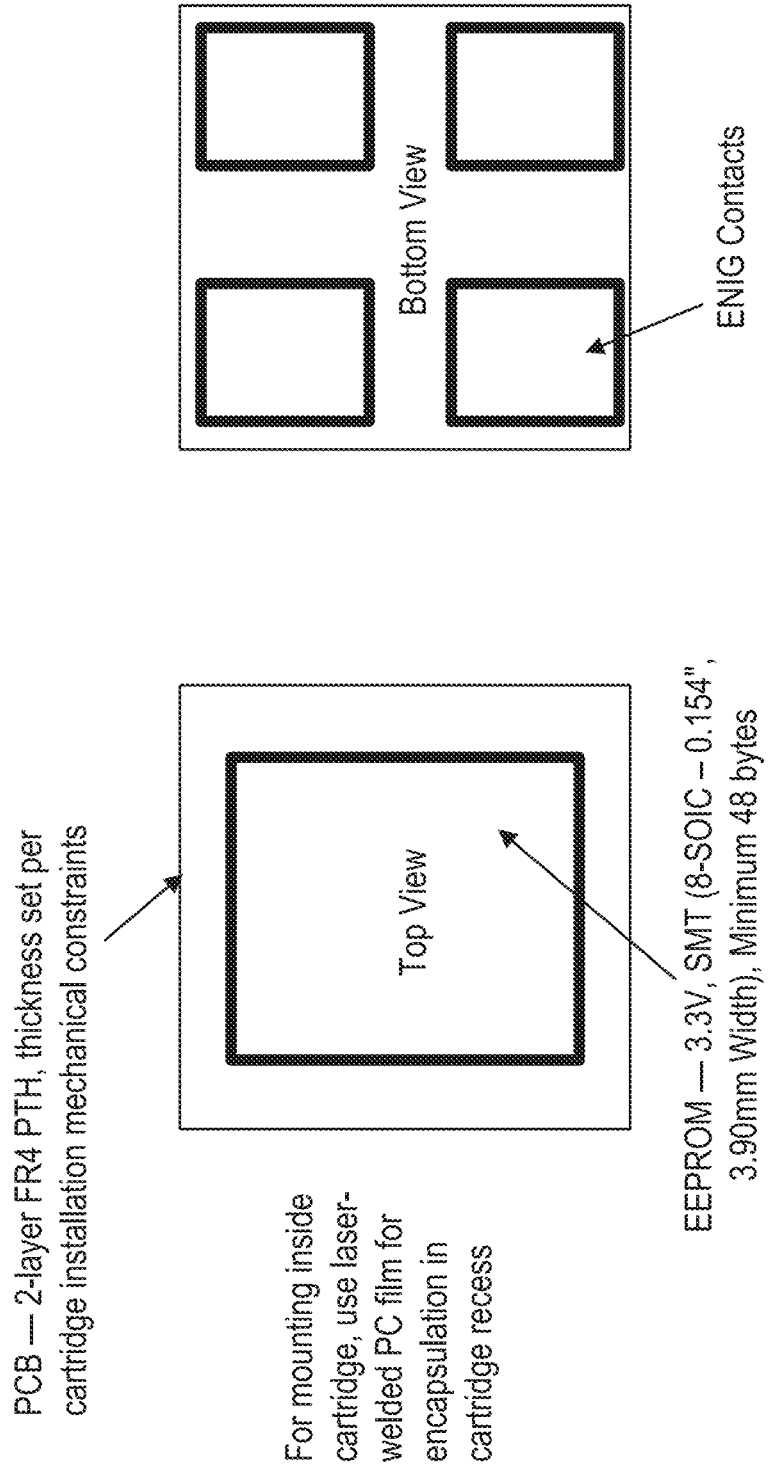
FIG. 46 illustrates cartridge identification/authorization components of the diagnostic testing system of FIG. 1.

Each cartridge 12 run on the analyzer 14 can be required to have a unique identifier (UID) in order to provide traceability between cartridge manufacturing parameters and customer usage/results. The UID can be read by the analyzer 14 and authorized via back-end cloud services prior operation of the cartridge 12 by the analyzer 14. For example, an EEPROM PCBA, such as illustrated in FIG. 46, can be incorporated into each cartridge 12. The EEPROM can read by the analyzer 14 over an inter-integrated circuit ($I^2C$) interface or a serial peripheral interface (SPI) with direct electrical spring-loaded contacts between the EEPROM and the analyzer 14. The EEPROM PCBA can have electroless nickel immersion gold (ENIG) contacts that are sufficiently large and have relatively large center-to-center spacing so as to ensure alignment of the analyzer spring-loaded contacts and the EEPROM ENIG contacts. The spring-loaded contacts can be selected with a suitable range of travel and cycle life from available spring-leaf type contacts and pogo pins.

The inclusion of a UID in each cartridge 12 can be used to satisfy any suitable cartridge identification/authorization requirements in any suitable manner. For example, the UID can be incorporated into the cartridge so as to allow the cartridge to be uniquely identified when inserted into the analyzer 14. The analyzer 14 can be configured to be able to scan/read the cartridge UID after the cartridge 12 has been clamped/locked into the analyzer 14. If the analyzer 14 is not able to read the cartridge UID, the analyzer 14 can be configured to unclamp the cartridge 12 to accommodate removal of the cartridge 12 from the analyzer 14 by the user for inspection/cleaning and reinsertion into the analyzer 14. The cartridge UID can be in accordance with any suitable cartridge device serial number specification. The UID data stored on each cartridge 12 may not be write protected, but can be encrypted using a suitable encryption standard to prevent mass counterfeiting. Each cartridge 12 can be configured to provide a suitable minimum number of data bytes (e.g., 48) for storage of an encrypted UID. The system 10 can be configured to authorize a cartridge 12 for use based on any suitable condition or combination of conditions. For example, the system 10 can be configured to authorize a cartridge 12 for use via backend cloud services based on any of the following conditions or any suitable combination of the following conditions: (1) a shelf-life for the cartridge 12 has not been exceeded, (2) the cartridge 12 is not from a bad manufacturing lot, and/or (3) the cartridge 12 is from an authorized manufacture and has a correctly encrypted and formatted UID. Following completion of the test, the cartridge UID can be associated and recorded with its test result along with any other suitable associated data.

Sensors

In addition to the heater and heater protection NTC thermistors, the analyzer 14 includes the accelerometer 176, the ambient light sensor 174, and an internal ambient temperature sensor. The accelerometer 176 is employed to ensure that the orientation of the analyzer 14 is suitable for processing the assay. Fluids levels in the cartridge 12 are sensitive to the degree of tilt of the cartridge 12. In particular, the swab chamber 124 may need at least a 4 degree tilt in order for the lysis buffer to properly hydrate the swab tip and allow sufficient sample recovery. The swab chamber 124 can be designed with a negative 4 degree tilt front to back of the analyzer 12. The analyzer cartridge clamp assembly can be configured to provide an additional 2 degree tilt front to back. Accordingly, on a level surface, the swab chamber 124 can have a nominal tilt of 6 degrees. The accelerometer 176 can be configured to output a signal that is processed by the controller to detect a back to front tilt of the analyzer 14 of greater than 2 degrees that could impact the swab chamber sample recovery.

The ambient light sensor 174 is employed to measure external light penetration into the analyzer 14. The measured external light penetration can be used to assess whether the CRISPR kinetic data reflects any significant external light component to alert for any potential detection errors.

An ambient temperature sensor can be used to correlate external ambient temperature with the internal temperature of the analyzer 14. For example, an internal temperature NTC thermistor can be used to correlate external temperatures with internal temperatures. An internal temperature of the analyzer 14 outside an acceptable range can be used to alert the user and prevent running of an assay.

Pressure Based Aliquot Staging

Figure 47:
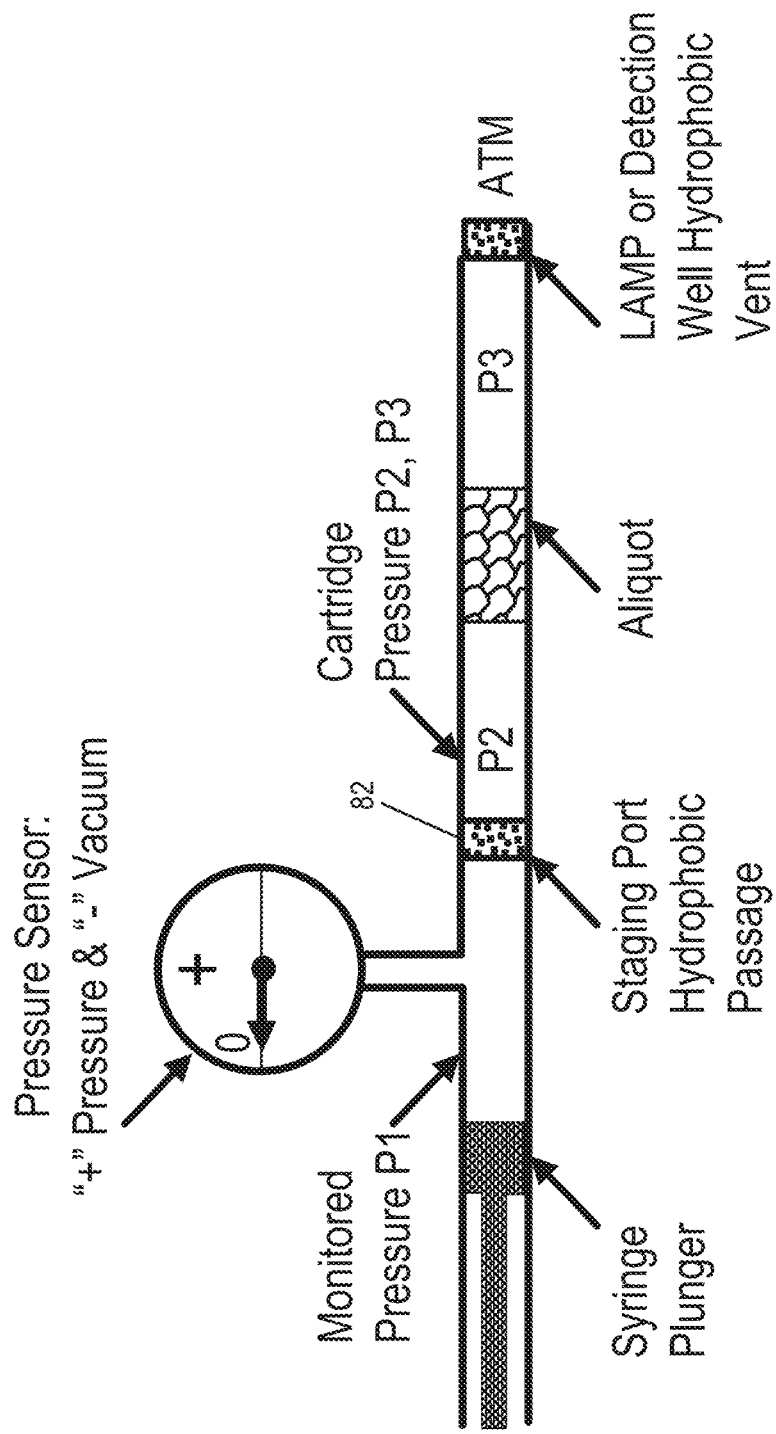
FIG. 47 schematically illustrates components and an actuation pressure based approach used to induce and control fluid transfer within the cartridge in the diagnostic testing system of FIG. 1.

FIG. 47 illustrates the pressure based approach for controlling transfer of an aliquot within the cartridge 12. As described herein, an aliquot of the lysed sample solution can be drawn from the lysis chamber 68 via air extracted from the actuation port 83 via the syringe pump 258. The pressure sensor 178 measures pressure (P1) within the syringe pump 258 during the staging of the aliquot. When the aliquot comes into contact with the aliquot staging hydrophobic vent 82 associated with the staging well 76, the aliquot staging hydrophobic vent 82 resists passage of the lysed sample solution through the aliquot staging hydrophobic vent. With the movement of the aliquot stopped by the hydrophobic vent 82, continued actuation of the syringe pump 258 induces an increase in the suction pressure generated by the syringe pump 258. The pressure sensor 178 generates a pressure signal that is monitored by the control unit 156. The control unit 156 is configured to cease further actuation of the syringe pump 258 in response to detecting an increase in the suction pressure indicative of contact of the aliquot with the hydrophobic vent 82.

Figure 48:
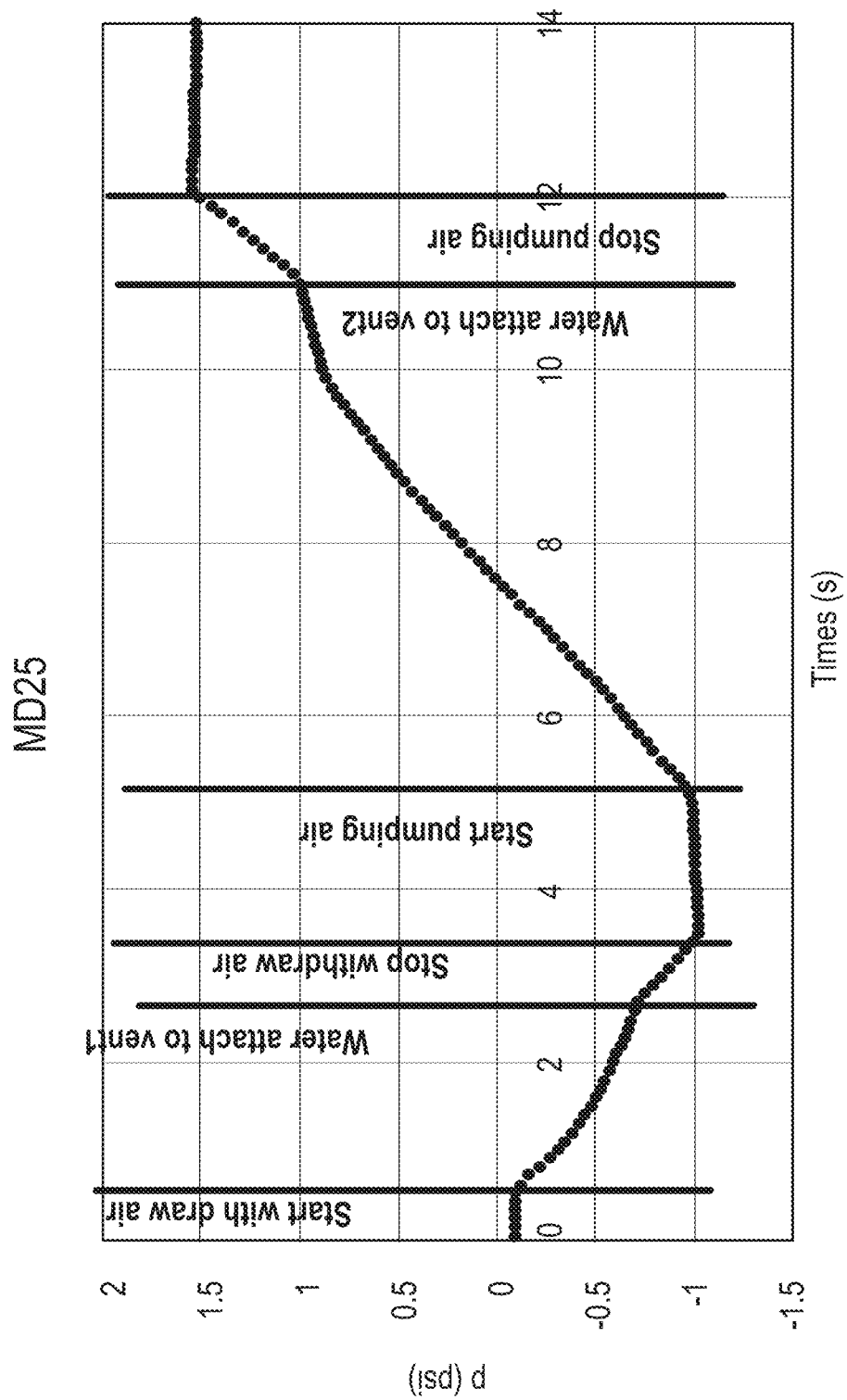
FIG. 48 illustrates pressure applied to an actuation port of the cartridge by the pump assembly of FIG. 36 to stage an aliquot and move the aliquot to a processing well.

Following staging of the aliquot from the lysis chamber 68 to the staging well 76, the aliquot is then transferred from the staging well 76 to one of the amplification wells 70. As described herein, an aliquot of the lysed sample solution can be pushed from the staging well 76 via air injected into the actuation port 83 by the syringe pump 258. The pressure sensor 178 measures pressure (P1) within the syringe pump 258 during the pushing of the aliquot to the amplification well 70. When the aliquot comes into contact with the amplification well hydrophobic vent 88, the amplification well hydrophobic vent 88 resists passage of the lysed sample solution through the amplification well hydrophobic vent. With the movement of the aliquot stopped by the amplification well hydrophobic vent 88, continued actuation of the syringe pump 258 induces an increase in the positive pressure generated by the syringe pump 258. The pressure sensor 178 generates a pressure signal that is monitored by the control unit 156. The control unit 156 is configured to cease further actuation of the syringe pump 258 in response to detecting an increase in the positive pressure indicative of contact of the aliquot with the amplification well hydrophobic vent 88. FIG. 48 shows a representative pressure curve for the staging of the aliquot to the staging well and the transfer of the aliquot to the amplification well.

Figure 49:
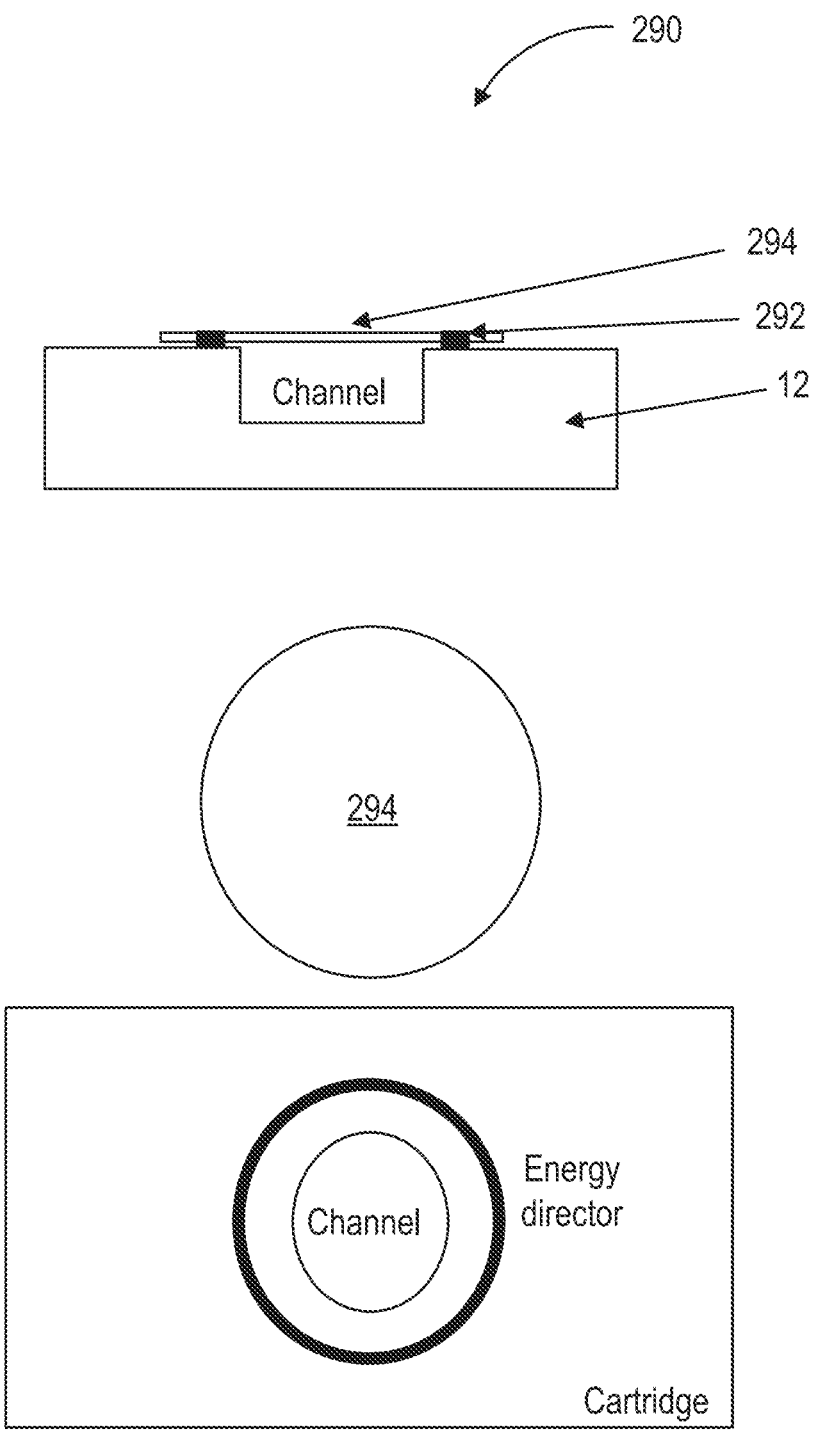
FIG. 49 illustrates a hydrophobic staging vent that can be used in the cartridge of the diagnostic testing system of FIG. 1.

FIG. 49 illustrates the configuration of a hydrophobic vent 290 that can be used in the cartridge 12. The hydrophobic vent 290 includes a cylindrical mount 292 and a Polytetrafluoroethylene (PTFE) porous membrane 294 mounted to the cylindrical mount 292. The cylindrical mount 292 is mounted to the cartridge 12 and surrounds an aperture 296 connected to a fluidic channel 298 of the cartridge 12. In the illustrated embodiment, the cylindrical mount 292 has an inner diameter that is greater than a diameter of the aperture 296, thereby giving the PTFE porous membrane 294 a surface area greater than the cross-sectional area of the aperture 296. The PTFE porous membrane 294 is configured to accommodate passage of airflow and inhibit the passage of liquid.

Figure 50:
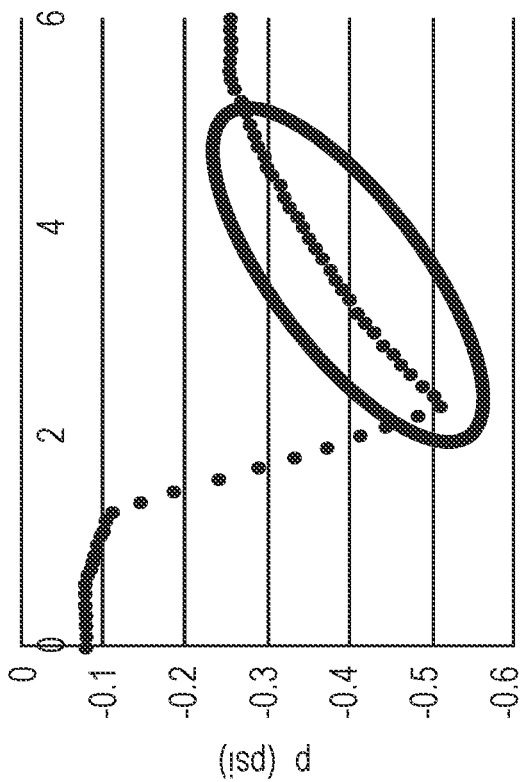
FIG. 50 illustrates an actuation pressure profile indicative of lack of contact between an aliquot and an aliquot hydrophobic staging vent in the diagnostic testing system of FIG. 1.
Figure 50:
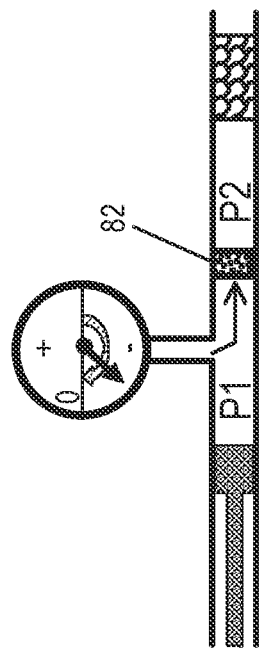
Figure 51:
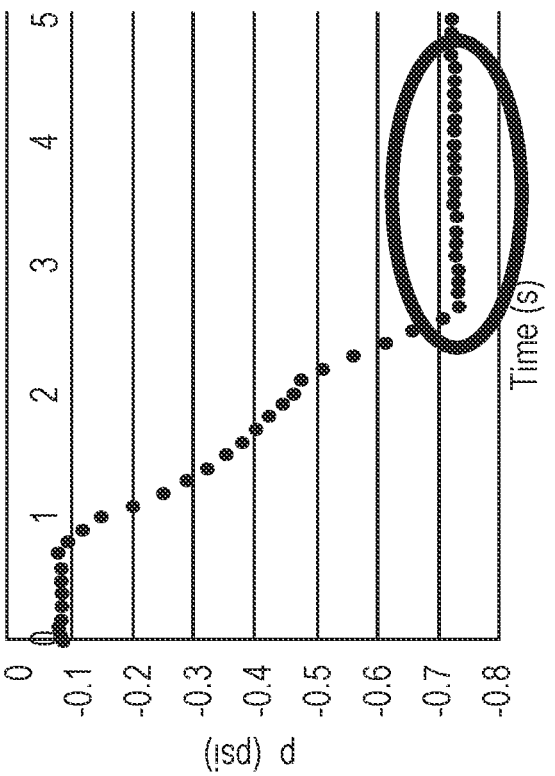
FIG. 51 illustrates an actuation pressure profile indicative of contact between an aliquot and an aliquot hydrophobic staging vent in the diagnostic testing system of FIG. 1.
Figure 51:
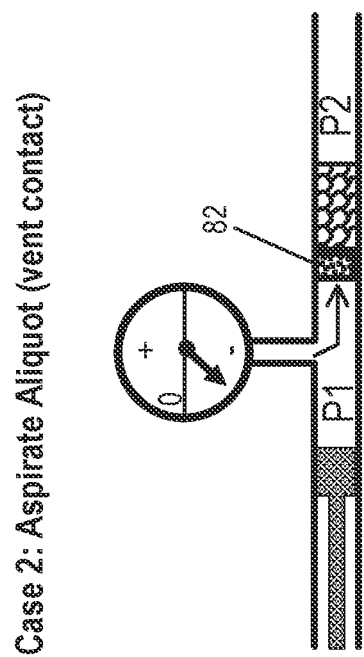

FIG. 50, FIG. 51, FIG. 52, and FIG. 53 illustrate example actuation pressure profiles that may occur during the transfer of an aliquot within the cartridge 12. FIG. 50 shows a pressure profile in which an aliquot is drawn from the lysis chamber 68 towards the staging well 76 but does not come into contact with the aliquot staging hydrophobic passage 82 at the end of a limited actuation stroke of the syringe pump 258. Due to the lack of contact, air continues to flow through the aliquot staging hydrophobic passage 82 due to pressure (P1) being less than pressure (P2), thereby increasing pressure (P1) over time. FIG. 51 shows a pressure profile in which an aliquot is drawn from the lysis chamber 68 towards the staging well 76 and comes into contact with the aliquot staging hydrophobic passage 82 at the end of a limited actuation stroke of the syringe pump 258. Due to the contact, no air flows through the aliquot staging hydrophobic vent 82 following the end of the limited actuation stroke of the syringe pump 258 so that the pressure (P1) does not change over time.

Figure 52:
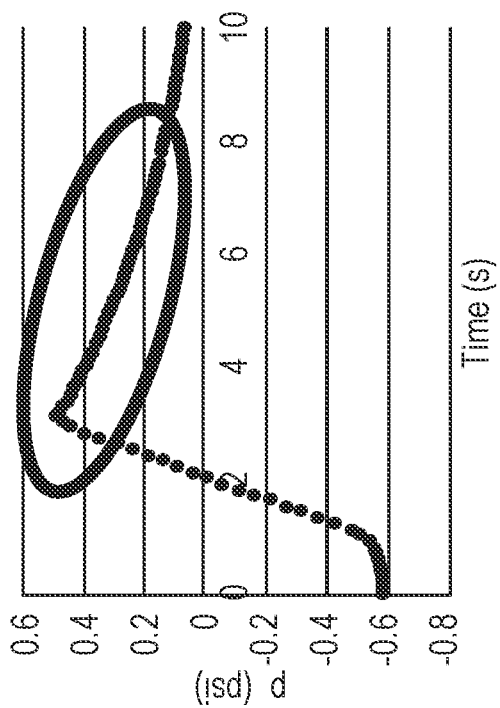
FIG. 52 illustrates an actuation pressure profile indicative of lack of contact between an aliquot and a downstream hydrophobic staging vent in the diagnostic testing system of FIG. 1.
Figure 52:
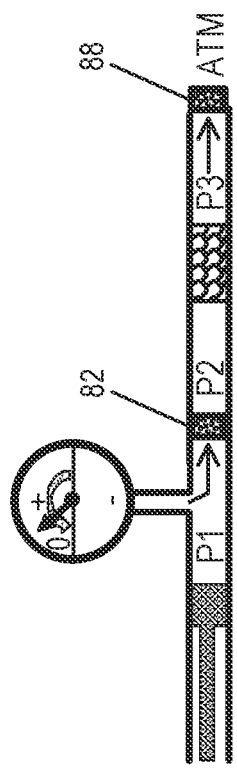
Figure 53:
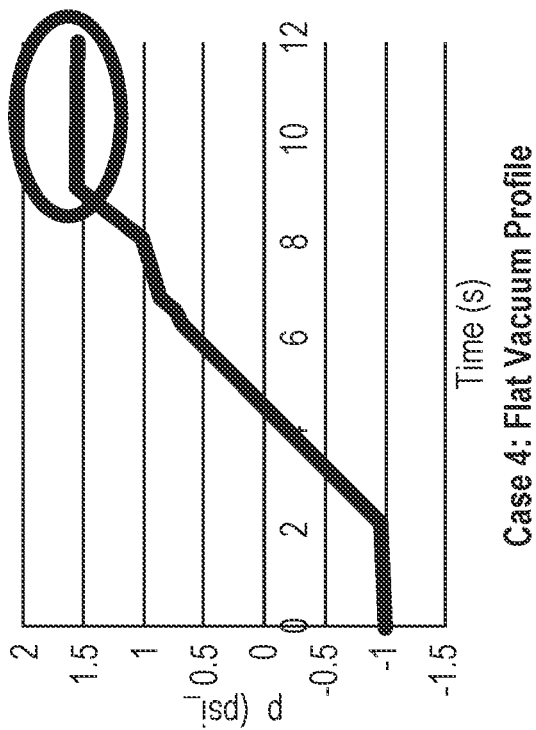
FIG. 53 illustrates an actuation pressure profile indicative of contact between an aliquot and a downstream hydrophobic staging vent in the diagnostic testing system of FIG. 1.
Figure 53:
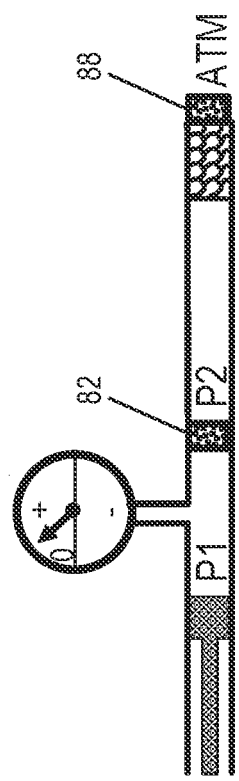

FIG. 52 shows a pressure profile in which an aliquot is pushed from the staging well 76 towards the amplification well 70 but does not come into contact with the amplification well hydrophobic vent 88 at the end of a limited actuation stroke of the syringe pump 258. Due to the lack of contact, air continues to flow through the amplification well hydrophobic vent 88 due to pressure (P3) being greater than ambient pressure on the other side of the amplification well hydrophobic vent 88, thereby decreasing pressure (P1) over time. FIG. 53 shows a pressure profile in which an aliquot is pushed from the staging well 76 towards the amplification well 70 and comes into contact with the amplification well hydrophobic vent 88 at the end of a limited actuation stroke of the syringe pump 258. Due to the contact, no air flows through the amplification well hydrophobic vent 88 following the end of the limited actuation stroke of the syringe pump 258 so that the pressure (P1) does not change over time.

Figure 54:
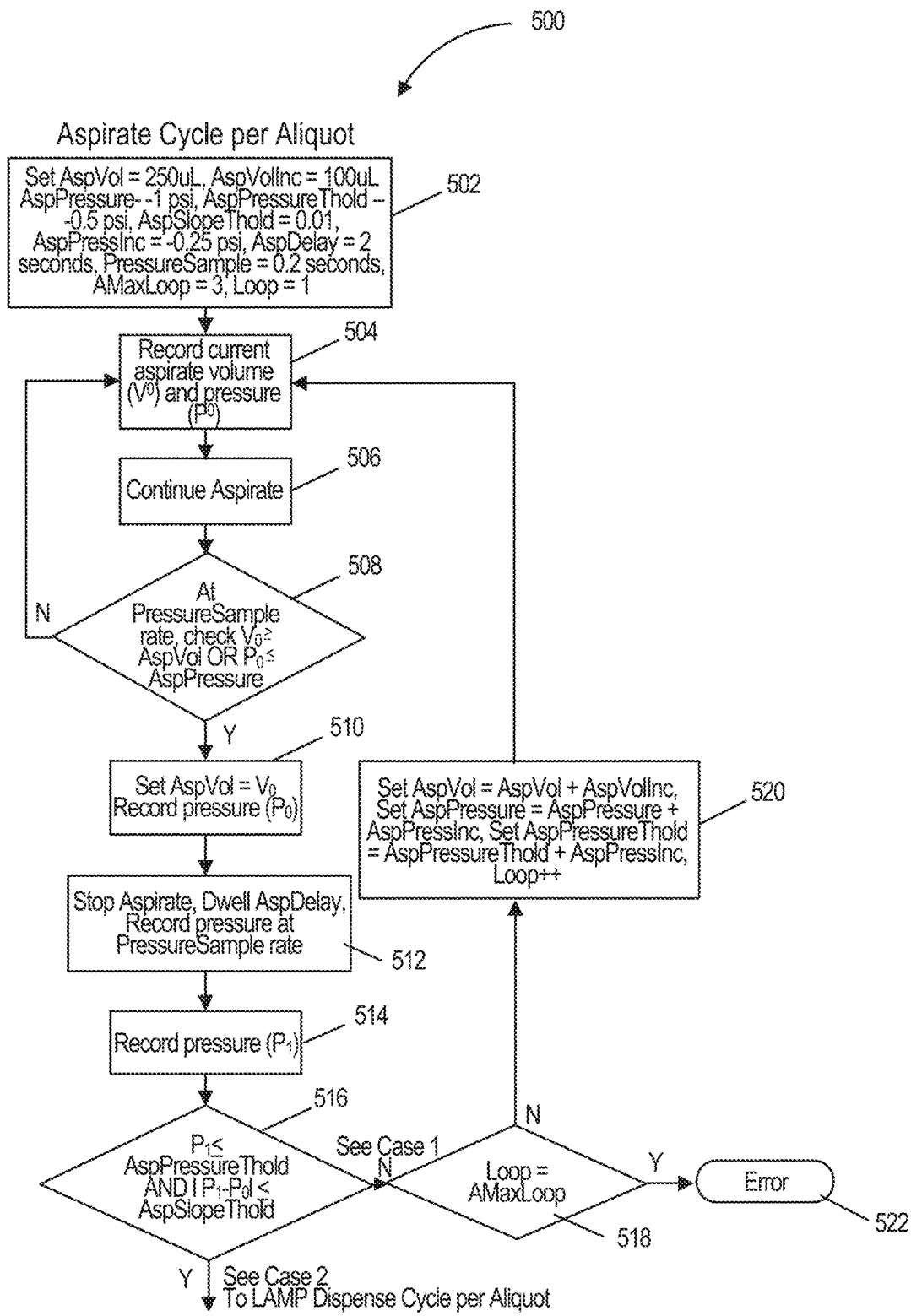
FIG. 54 is a simplified flow chart of an approach for aspirating an aliquot in the cartridge of the diagnostic testing system of FIG. 1.
Figure 55:
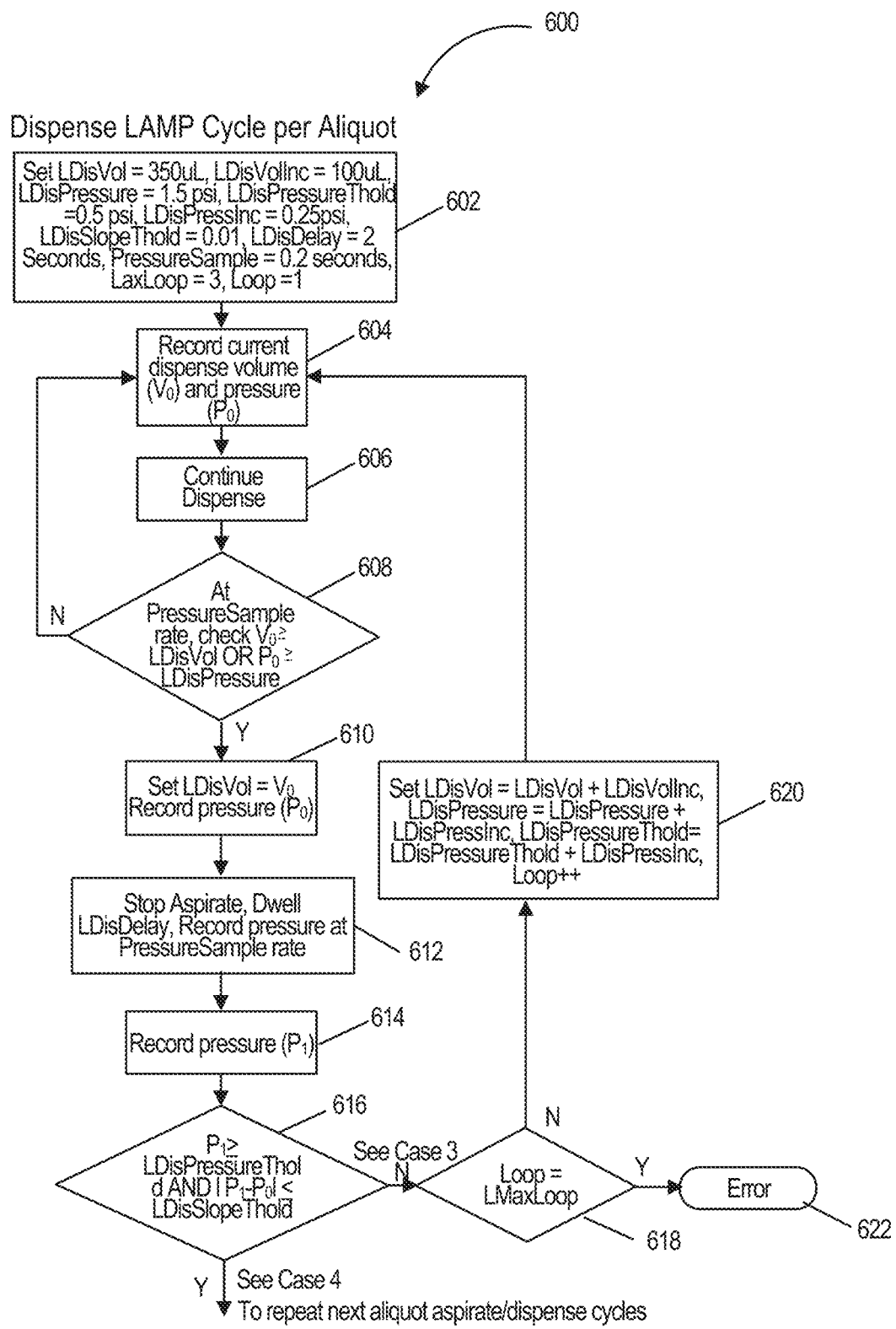
FIG. 55 is a simplified flow chart of an approach for dispensing an aliquot to a LAMP well in the cartridge of the diagnostic testing system of FIG. 1.
Figure 56:
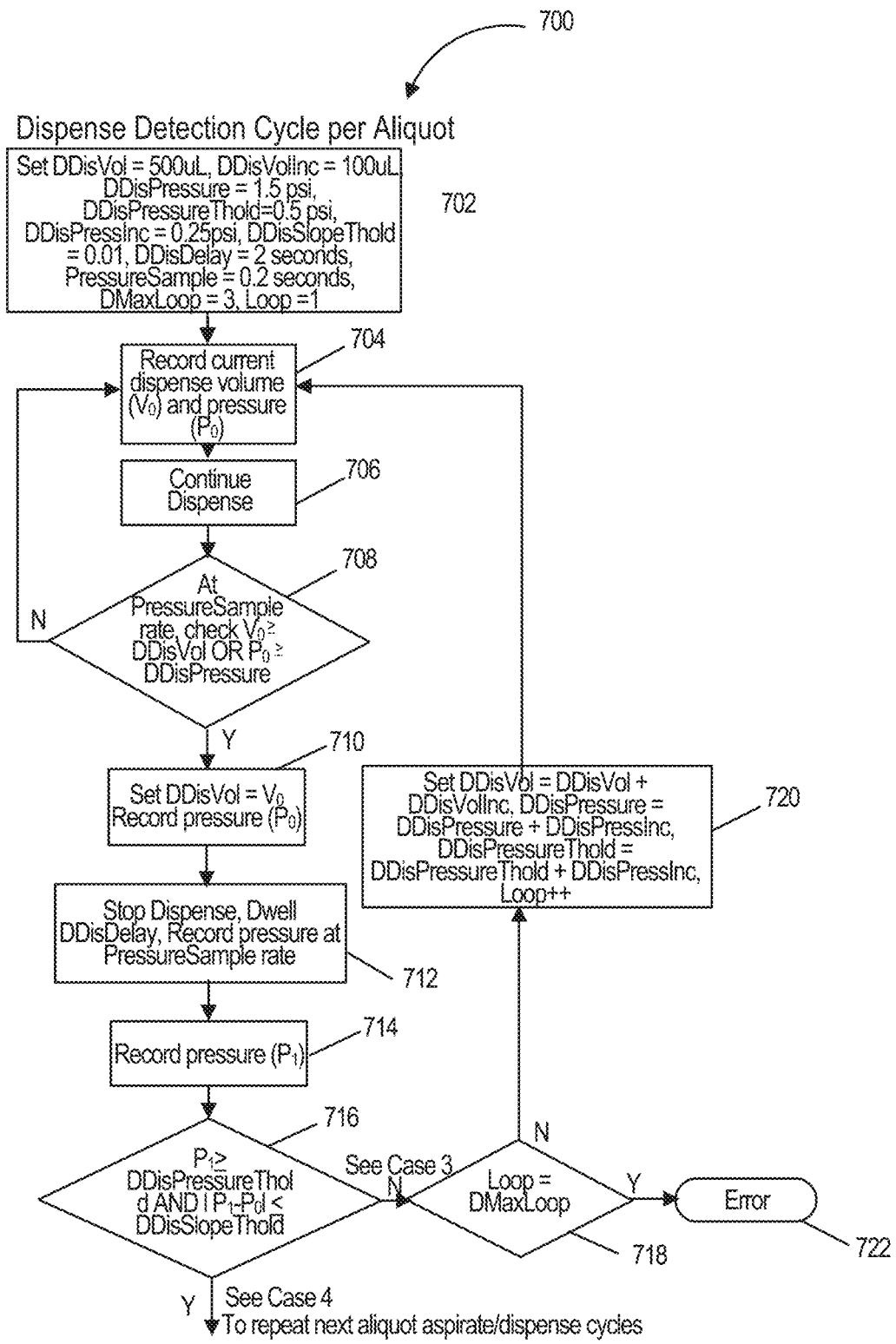
FIG. 56 is a simplified flow chart of an approach for dispensing an aliquot to a detection well in the cartridge of the diagnostic testing system of FIG. 1.

FIG. 54, FIG. 55, and FIG. 56 are simplified flow charts of actuation pressure based approaches for controlling transfer of an aliquot with in the cartridge. FIG. 54 shows an approach 500 for staging an aliquot from the lysis chamber 68 to the staging well 76. FIG. 55 show an approach 600 for transferring an aliquot from the staging well 76 to an amplification well 70. FIG. 56 shows an approach 700 for transferring an aliquot from a CRISPR well 72 to a detection well 74.

The approach 500 for staging an aliquot from the lysis chamber 68 to the staging well 76 begins in act 502 with the setting of first loop aspiration parameters values to suitable respective values. For example, in the illustrated example, aspirate volume is set to 250 uL, aspirate volume increment is set to 100 uL, aspirate pressure is set to −1.0 psi, aspirate pressure threshold is set to −0.5 psi, aspirate slope threshold is set to 0.01, aspirate pressure increment is set to −0.25 psi, aspirate dwell time is set to 2 seconds, pressure sampling frequency is set to 0.2 seconds, aspirate maximum number of loops before error is set to 3, and a loop counter is set to 1. In act 504, the current aspirate volume (Vo) and the current aspirate pressure (Po) is recorded. In act 506, the pump assembly 86 is operated to continue aspiration from the cartridge 12. In act 508, a check is made if the current aspirate volume (Vo) is greater than or equal to the aspirate volume (e.g., 250 uL for the first loop) or if the current aspirate pressure (Po) is less than or equal to the aspirate pressure (e.g., −1.0 psi). If the current aspirate volume (Vo) is not greater than or equal to the aspirate volume (e.g., 250 uL) or if the current aspirate pressure (Po) is not less than or equal to the aspirate pressure (e.g., −1.0 psi), act 504, act 506, and act 508 are repeated until the current aspirate volume (Vo) is greater than or equal to the aspirate volume (e.g., 250 uL) or the current aspirate pressure (Po) is less than or equal to the aspirate pressure (e.g., −1.0 psi). When the check of act 508 indicates that the current aspirate volume (Vo) is greater than or equal to the aspirate volume (e.g., 250 uL) or the current aspirate pressure (Po) is less than or equal to the aspirate pressure (e.g., −1.0 psi), the aspirate volume is set to the current aspirate volume (Vo) and the aspirate pressure is set to the current aspirate pressure (Po) in act 510. In act 512, the operation of the pump assembly 86 is stopped for the aspiration dwell time (e.g., 2 seconds) and the aspiration pressure is monitored at the pressure sampling frequency (e.g., every 0.2 seconds). In act 514 the aspiration pressure ($P_1$) is recorded. In act 516, a check is made if the aspiration pressure (P1) is less than or equal to the aspirate pressure threshold (e.g., −0.5) and the absolute value of the rate of change of the aspirate pressure during the aspiration dwell period is less than the aspirate slope threshold (e.g., 0.01 psi/0.2 second sample interval). If the check of act 516 indicates that the aspirate pressure does not vary more than the checked value and rate, the process 500 ends since the demonstrated pressure stability indicates that the aliquot has been brought into contact with the staging chamber hydrophobic vent 82. If the check of act 516 indicates that the aspirate pressure does vary more than the checked value and rate, the process 500 continues to act 518 in which the loop counter is incremented, act 520 in which aspiration parameters are updated, followed by repetition of acts 504 through 516. In the first loop through acts 504 through 516, the initial aspiration volume can be set to a suitable initial value (e.g., 250 uL). In the subsequent loops of act 504 through act 516, the incremental aspiration volume can be set to a suitable incremental volume (e.g., 100 uL). The loop through acts 504 through 516 can be accomplished any suitable number of times (e.g., 3 times). If the check in act 516 does not indicate contact with the aliquot and the staging chamber hydrophobic vent 82 before the accomplishment of the specified maximum number of repetitions of acts 504 through 506, an error indication can be generated and output in act 522.

The approach 600 for transferring an aliquot from the staging well 76 to an amplification well 70 is similar to the approach 500, but employs positive dispense pressure to push the aliquot as opposed to the vacuum pressure employed in the approach 500. The process 600 begins in act 602 with the setting of first loop LAMP dispense parameters values to suitable respective values. For example, in the illustrated example, LAMP dispense volume is set to 350 uL, LAMP dispense volume increment is set to 100 uL, LAMP dispense pressure is set to 1.5 psi, LAMP dispense pressure threshold is set to 0.5 psi, LAMP dispense pressure increment is set to 0.25 psi, LAMP dispense slope threshold is set to 0.01, LAMP dispense dwell time is set to 2 seconds, pressure sampling frequency is set to 0.2 seconds, LAMP dispense maximum number of loops before error is set to 3, and a loop counter is set to 1. In act 604, the current dispense volume (Vo) and the current dispense pressure (Po) is recorded. In act 606, the pump assembly 86 is operated to continue dispensing air into the cartridge 12. In act 608, a check is made if the current dispense volume (Vo) is greater than or equal to the LAMP dispense volume (e.g., 350 uL for first loop) or if the current dispense pressure (Po) is greater than or equal to the LAMP dispense pressure (e.g., 1.5 psi). If the current dispense volume (Vo) is not greater than or equal to the LAMP dispense volume (e.g., 350 uL) or if the current dispense pressure (Po) is not greater than or equal to the LAMP dispense pressure (e.g., 1.5 psi), act 604, act 606, and act 608 are repeated until the current dispense volume (Vo) is greater than or equal to the LAMP dispense volume (e.g., 350 uL) or the current dispense pressure (Po) is greater than or equal to the LAMP dispense pressure (e.g., 1.5 psi). When the check of act 608 indicates that the current dispense volume (Vo) is greater than or equal to the LAMP dispense volume (e.g., 350 uL) or the current dispense pressure (Po) is greater than or equal to the LAMP dispense pressure (e.g., 1.5 psi), the dispense volume is set to the current dispense volume (Vo) and the dispense pressure is set to the current dispense pressure (Po) in act 610. In act 612, the operation of the pump assembly 86 is stopped for the dispense dwell time (e.g., 2 seconds) and the dispense pressure is monitored at the pressure sampling frequency (e.g., every 0.2 seconds). In act 614 the dispense pressure ($P_1$) is recorded. In act 616, a check is made if the dispense pressure (P1) is greater than or equal to the dispense pressure threshold (e.g., 0.5) and the absolute value of the rate of change of the dispense pressure during the dispense dwell period is less than the dispense slope threshold (e.g., 0.01 psi/0.2 second sample interval). If the check of act 616 indicates that the dispense pressure does not vary more than the checked value and rate, the process 600 ends since the demonstrated pressure stability indicates that the aliquot has been brought into contact with the amplification well hydrophobic vent 88. If the check of act 616 indicates that the dispense pressure does vary more than the checked value and rate, the process 600 continues to act 618 in which the loop counter is incremented, act 620 in which dispense parameters are updated, followed by repetition of acts 604 through 616. In the first loop through acts 604 through 616, the initial dispense volume can be set to a suitable initial value (e.g., 350 uL). In the subsequent loops through acts 604 through 616, the incremental dispense volume can be set to a suitable incremental volume (e.g., 100 uL). The loop through acts 604 through 616 can be accomplished any suitable number of times (e.g., 3 times). If the check in act 616 does not indicate contact with the aliquot and the amplification well hydrophobic vent 88 before the accomplishment of the specified maximum number of repetitions of acts 604 through 606, an error indication can be generated and output in act 622.

The approach 700 for transferring an aliquot from a CRISPR well 72 to a detection well 74 is similar to the approach 600. The process 700 begins in act 702 with the setting of first loop detection cycle dispense parameters values to suitable respective values. For example, in the illustrated example, detection dispense volume is set to 500 uL, detection dispense volume increment is set to 100 uL, detection dispense pressure is set to 1.5 psi, detection dispense pressure threshold is set to 0.5 psi, detection dispense pressure increment is set to 0.25 psi, detection dispense slope threshold is set to 0.01, detection dispense dwell time is set to 2 seconds, pressure sampling frequency is set to 0.2 seconds, detection dispense maximum number of loops before error is set to 3, and a loop counter is set to 1. In act 704, the current dispense volume (Vo) and the current dispense pressure (Po) is recorded. In act 706, the pump assembly 86 is operated to continue dispensing air into the cartridge 12. In act 708, a check is made if the current dispense volume (Vo) is greater than or equal to the detection dispense volume (e.g., 500 uL for first loop) or if the current dispense pressure (Po) is greater than or equal to the detection dispense pressure (e.g., 1.5 psi). If the current dispense volume (Vo) is not greater than or equal to the detection dispense volume (e.g., 500 uL) or if the current dispense pressure (Po) is not greater than or equal to the dispense pressure (e.g., 1.5 psi), act 704, act 706, and act 708 are repeated until the current dispense volume (Vo) is greater than or equal to the dispense volume (e.g., 500 uL) or the current dispense pressure (Po) is greater than or equal to the dispense pressure (e.g., 1.5 psi). When the check of act 708 indicates that the current dispense volume (Vo) is greater than or equal to the detection dispense volume (e.g., 500 uL) or the current dispense pressure (Po) is greater than or equal to the dispense pressure (e.g., 1.5 psi), the dispense volume is set to the current dispense volume (Vo) and the dispense pressure is set to the current dispense pressure (Po) in act 710. In act 712, the operation of the pump assembly 86 is stopped for the dispense dwell time (e.g., 2 seconds) and the dispense pressure is monitored at the pressure sampling frequency (e.g., every 0.2 seconds). In act 714 the dispense pressure ($P_1$) is recorded. In act 716, a check is made if the dispense pressure (P1) is greater than or equal to the dispense pressure threshold (e.g., 0.5) and the absolute value of the rate of change of the dispense pressure during the dispense dwell period is less than the dispense slope threshold (e.g., 0.01 psi/0.2 second sample interval). If the check of act 716 indicates that the dispense pressure does not vary more than the checked value and rate, the process 700 ends since the demonstrated pressure stability indicates that the aliquot has been brought into contact with the detection well hydrophobic vent 98. If the check of act 716 indicates that the dispense pressure does vary more than the checked value and rate, the process 700 continues to act 718 in which the loop counter is incremented, act 720 in which dispense parameters are updated, followed by repetition of acts 704 through 716. In the first loop through acts 704 through 716, the initial dispense volume can be set to a suitable initial value (e.g., 500 uL). In the subsequent loops through acts 704 through 716, the incremental dispense volume can be set to a suitable incremental volume (e.g., 100 uL). The loop through acts 704 through 716 can be accomplished any suitable number of times (e.g., 3 times). If the check in act 716 does not indicate contact with the aliquot and the detection well hydrophobic vent 98 before the accomplishment of the specified maximum number of repetitions of acts 704 through 706, an error indication can be generated and output in act 722.

Figure 57:
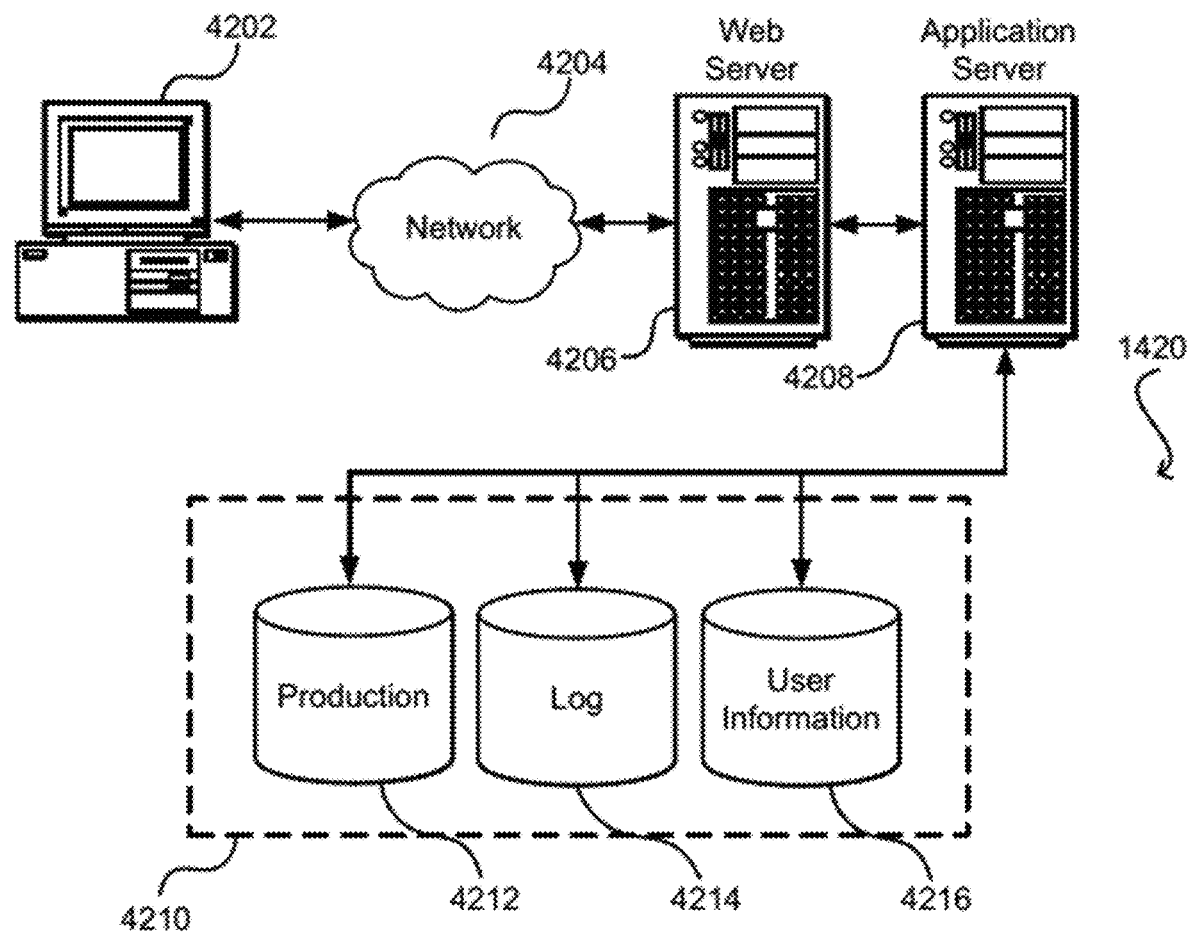
FIG. 57 illustrates an environment in which various embodiments can be implemented.

FIG. 57 illustrates aspects of an example environment 4200 for implementing aspects in accordance with various embodiments. As will be appreciated, although a Web-based environment is used for purposes of explanation, different environments may be used, as appropriate, to implement various embodiments. The environment includes the user device 16, which can include any appropriate device operable to send and receive requests, messages, or information over an appropriate network 4204 and convey information back to a user of the device. Examples of such user devices 16 include personal computers, cell phones, handheld messaging devices, laptop computers, set-top boxes, personal data assistants, electronic book readers, and the like. The network can include any appropriate network, including an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections and combinations thereof. In this example, the network includes the Internet, as the environment includes a Web server 4206 for receiving requests and serving content in response thereto, although for other networks an alternative device serving a similar purpose could be used as would be apparent to one of ordinary skill in the art.

The illustrative environment includes at least one application server 4208 and a data store 4210. It should be understood that there can be several application servers, layers, or other elements, processes, or components, which may be chained or otherwise configured, which can interact to perform tasks such as obtaining data from an appropriate data store. As used herein the term "data store" refers to any device or combination of devices capable of storing, accessing, and retrieving data, which may include any combination and number of data servers, databases, data storage devices, and data storage media, in any standard, distributed, or clustered environment. The application server can include any appropriate hardware and software for integrating with the data store as needed to execute aspects of one or more applications for the client device, handling a majority of the data access and business logic for an application. The application server provides access control services in cooperation with the data store and is able to generate content such as text, graphics, audio, and/or video to be transferred to the user, which may be served to the user by the Web server in the form of HyperText Markup Language ("HTML"), Extensible Markup Language ("XML"), or another appropriate structured language in this example. The handling of all requests and responses, as well as the delivery of content between the user device 16 and the application server 4208, can be handled by the Web server. It should be understood that the Web and application servers are not required and are merely example components, as structured code discussed herein can be executed on any appropriate device or host machine as discussed elsewhere herein.

The data store 4210 can include several separate data tables, databases or other data storage mechanisms and media for storing data relating to a particular aspect. For example, the data store illustrated includes mechanisms for storing production data 4212 and user information 4216, which can be used to serve content for the production side. The data store also is shown to include a mechanism for storing log data 4214, which can be used for reporting, analysis, or other such purposes. It should be understood that there can be many other aspects that may need to be stored in the data store, such as for page image information and to access right information, which can be stored in any of the above listed mechanisms as appropriate or in additional mechanisms in the data store 4210. The data store 4210 is operable, through logic associated therewith, to receive instructions from the application server 4208 and obtain, update or otherwise process data in response thereto. In one example, a user might submit a search request for a certain type of item. In this case, the data store might access the user information to verify the identity of the user and can access the catalog detail information to obtain information about items of that type. The information then can be returned to the user, such as in a results listing on a Web page that the user is able to view via a browser on the user device 16. Information for a particular item of interest can be viewed in a dedicated page or window of the browser.

Each server typically will include an operating system that provides executable program instructions for the general administration and operation of that server and typically will include a computer-readable storage medium (e.g., a hard disk, random access memory, read only memory, etc.) storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 57. Thus, the depiction of the system 4200 in FIG. 57 should be taken as being illustrative in nature and not limiting to the scope of the disclosure.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as Transmission Control Protocol/Internet Protocol ("TCP/IP"), Open System Interconnection ("OSI"), File Transfer Protocol ("FTP"), Universal Plug and Play ("UpnP"), Network File System ("NFS"), Common Internet File System ("CIFS"), and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including Hypertext Transfer Protocol ("HTTP") servers, FTP servers, Common Gateway Interface ("CGI") servers, data servers, Java servers, and business application servers. The server(s) also may be capable of executing programs or scripts in response to requests from user devices, such as by executing one or more Web applications that may be implemented as one or more scripts or programs written in any programming language, such as JavaR, C, C #, or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit ("CPU"), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired)), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory ("EEPROM"), flash memory or other memory technology, Compact Disc Read-Only Memory ("CD-ROM"), digital versatile disk (DVD), or other optical storage, magnetic cassettes, magnetic tape, magnetic disk storage, or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions, and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A cartridge for testing a biological sample, the cartridge comprising:
an aliquot staging well;
an aliquot staging well channel in fluid communication with the aliquot staging well;
a first reaction well;
a first reaction well channel in fluid communication with the first reaction well;
a second reaction well;
a second reaction well channel in fluid communication with the second reaction well;
an actuation port configured for coupling with a pump assembly of an analyzer device configured for operating the cartridge; and
a fluid channel control valve assembly that is reconfigurable between a first fluid channel configuration and a second fluid channel configuration; wherein in the first fluid channel configuration the aliquot staging well channel and the first reaction well channel are in fluid communication through the fluid channel control valve assembly for separately directing a first aliquot of a lysis buffer sample solution from the aliquot staging well to the first reaction well via injection of air into the cartridge through the actuation port by the pump assembly of the analyzer device and the second reaction well channel is fluidly isolated from the aliquot staging well channel via the fluid channel control valve assembly to block flow of any of the first aliquot of the lysis buffer sample solution from being transferred to the second reaction well, and wherein in the second fluid channel configuration the aliquot staging well channel and the second reaction well channel are in fluid communication through the fluid channel control valve assembly for separately directing a second aliquot of the lysis buffer sample solution from the aliquot staging well to the second reaction well via injection of air into the cartridge through the actuation port by the pump assembly of the analyzer device and the first reaction well channel is fluidly isolated from the aliquot staging well channel via the fluid channel control valve assembly to block flow of any of the second aliquot of the lysis buffer sample solution from being transferred to the first reaction well.

2. The cartridge of claim 1, wherein:
the first reaction well containing a first lyophilized amplification compound bead containing first amplification compounds for combination with the first aliquot of the lysis buffer sample solution to form a first amplification sample solution in the first reaction well, wherein the first reaction well is configured for transferring heat to the first amplification sample solution to form a first amplified sample solution in the first reaction well;
the second reaction well containing a second lyophilized amplification compound bead containing second amplification compounds for combination with the second aliquot of the lysis buffer sample solution to form a second amplification sample solution in the second reaction well, wherein the second reaction well is configured for transferring heat to the second amplification sample solution to form a second amplified sample solution in the second reaction well; and
the cartridge further comprises:
a first clustered regularly interspaced short palindromic repeats (CRISPR) well containing a first lyophilized CRISPR compound bead containing first CRISPR compounds for combination with the first amplified sample solution to form a first detection solution in the first CRISPR well;
a first detection well;
a second CRISPR well containing a second lyophilized CRISPR compound bead containing second CRISPR compounds for combination with the second amplified sample solution to form a second detection solution in the second CRISPR well;
a second detection well; and
a staging valve assembly that is reconfigurable between a blocking configuration and a transfer configuration, wherein the staging valve assembly in the blocking configuration blocks flow from the first reaction well to the first CRISPR well and blocks flow from the second reaction well to the second CRISPR well, wherein the staging valve assembly in the transfer configuration fluidly connects the first reaction well to the first CRISPR well for transfer of the first amplified sample solution from the first reaction well to the first CRISPR well and for transfer of the first detection solution from the first CRISPR well to the first detection well via injection of air into the cartridge through the actuation port, and wherein the staging valve assembly in the transfer configuration fluidly connects the second reaction well to the second CRISPR well for transfer of the second amplified sample solution from the second reaction well to the second CRISPR well and for transfer of the second detection solution from the second CRISPR well to the second detection well via injection of air into the cartridge through the actuation port.

3. The cartridge of claim 2, further comprising:
a first detection well hydrophobic vent via which the first detection well is vented, wherein the first detection well hydrophobic vent is configured to inhibit flow of the first detection solution through the first detection well hydrophobic vent;
a second detection well hydrophobic vent via which the second detection well is vented, wherein the second detection well hydrophobic vent is configured to inhibit flow of the second detection solution through the second detection well hydrophobic vent;
a first reaction well hydrophobic vent via which the first reaction well is vented, wherein the first reaction well hydrophobic vent is configured to inhibit flow of the lysis buffer sample solution through the first reaction well hydrophobic vent; and
a second reaction well hydrophobic vent via with the second reaction well is vented, wherein the second reaction well hydrophobic vent is configured to inhibit flow of the lysis buffer sample solution through the second reaction well hydrophobic vent.

4. The cartridge of claim 3, wherein:
the staging valve assembly comprises the first reaction well hydrophobic vent and the second reaction well hydrophobic vent;

the first reaction well is vented by the first reaction well hydrophobic vent while the staging valve assembly is in the blocking configuration; and the second reaction well is vented by the second reaction well hydrophobic vent while the staging valve assembly is in the blocking configuration.

5. The cartridge of claim 2, wherein the staging valve assembly comprises a sliding valve member that is translated to reconfigure the staging valve assembly between the blocking configuration and the transfer configuration.

6. The cartridge of claim 1, wherein the fluid channel control valve assembly comprises a rotor that is rotated around a rotation axis to reconfigure the fluid channel control valve assembly between the first fluid channel configuration and the second fluid channel configuration.

7. The cartridge of claim 1, further comprising an lysis chamber, wherein the fluid channel control valve assembly is reconfigurable to a staging configuration that fluidly connects the aliquot staging well with the lysis chamber for transfer of a first aliquot of the lysis buffer sample solution from the lysis chamber to the aliquot staging well via withdrawal of a first flow of air from the cartridge through the actuation port by the pump assembly of the analyzer device and a second aliquot of the lysis buffer sample solution from the lysis chamber to the aliquot staging well via withdrawal of a second flow of air from the cartridge through the actuation port by the pump assembly of the analyzer device.

8. The cartridge of claim 7, further comprising an aliquot staging well hydrophobic passage through which the actuation port is in fluid communication with the aliquot staging well, wherein the aliquot staging well hydrophobic passage is configured to inhibit flow of the lysis buffer sample solution through the aliquot staging well hydrophobic passage.

9. The cartridge of claim 1, further comprising:
a lysis chamber;
a swab chamber configured to receive a swab having a biological sample disposed on the swab; and
a buffer solution chamber assembly for storing a buffer solution, wherein the buffer solution chamber assembly is configured to interface with an actuation member of an analysis device to displace a quantity of the buffer solution from the buffer solution chamber assembly, displaces a quantity of a sample solution from the swab chamber, and transfers a quantity of the lysis buffer sample solution into the lysis chamber, wherein the sample solution is formed from a quantity of the buffer solution displaced from the buffer solution chamber assembly and a quantity of the biological sample displaced from the swab chamber, and wherein the lysis buffer sample solution is formed from a quantity of the sample solution displaced from the swab chamber and lysis compounds.

10. The cartridge of claim 9, further comprising a lysis bead chamber containing a lyophilized lysis compound bead, wherein the swab chamber and the buffer solution chamber assembly are in fluid communication through the lysis bead chamber so that the lysis bead chamber received the a quantity of the buffer solution displaced from the buffer solution chamber assembly to form a lysis buffer in the lysis bead chamber, and wherein the displacement of the buffer solution from the buffer solution chamber assembly induces transfer of a quantity of the lysis buffer from the lysis bead chamber into the swab chamber.

11. The cartridge of claim 9, further comprising a lysis bead chamber containing a lyophilized lysis compound bead, wherein the swab chamber and the lysis chamber are in fluid communication through the lysis bead chamber so that the lysis bead chamber receives a quantity of a buffer sample solution displaced from the swab chamber to form a lysis sample solution in the lysis bead chamber, and wherein the displacement of the buffer solution from the buffer solution chamber assembly induces transfer of a quantity of the lysis sample solution from the lysis bead chamber into the lysis chamber.

12. The cartridge of claim 9, further comprising a top cover panel having a buffer solution chamber assembly aperture through which the actuation member of the analysis device translates to interface with the buffer solution chamber assembly.

13. The cartridge of claim 12, wherein the buffer solution chamber assembly comprises a piston that is actuated by the actuation member of the analysis device.

14. The cartridge of claim 13, wherein the buffer solution chamber assembly comprises a buffer solution chamber and the piston interfaces with a sidewall of the buffer solution chamber.

15. The cartridge of claim 9, further comprising a lysis chamber hydrophobic vent that vents the lysis chamber during transfer of the lysis buffer sample solution into the lysis chamber, wherein the lysis chamber hydrophobic vent is configured to inhibit flow of the lysis buffer sample solution through the lysis chamber hydrophobic vent.

16. The cartridge of claim 9, configured to be operable to process the biological sample using reverse transcriptase loop-mediated amplification (RT-LAMP) followed by a fluorescence emission triggered by a Clustered Regularly Interspaced Short Palindromic Repeats (CRISPR)-CRISPR associated proteins (CAS) enzyme.

* * * * *